(12) United States Patent
Lucero et al.

(10) Patent No.: US 7,557,092 B2
(45) Date of Patent: Jul. 7, 2009

(54) PURINERGIC MODULATION OF SMELL

(75) Inventors: Mary Lucero, Salt Lake City, UT (US); Colleen Hegg, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 156 days.

(21) Appl. No.: 10/535,774

(22) PCT Filed: Nov. 21, 2003

(86) PCT No.: PCT/US03/37389

§ 371 (c)(1),
(2), (4) Date: Mar. 16, 2006

(87) PCT Pub. No.: WO2004/047749

PCT Pub. Date: Jun. 10, 2004

(65) Prior Publication Data

US 2006/0264398 A1  Nov. 23, 2006

Related U.S. Application Data

(60) Provisional application No. 60/428,140, filed on Nov. 21, 2002.

(51) Int. Cl.
*A01N 43/04* (2006.01)
*A61K 31/70* (2006.01)

(52) U.S. Cl. .............. 514/47; 514/42; 514/43; 514/45; 514/46

(58) Field of Classification Search ............ None
See application file for complete search history.

(56) References Cited

FOREIGN PATENT DOCUMENTS

| EP | 0 389 667 A | 10/1990 |
|---|---|---|
| EP | 1 004 654 A2 | 5/2000 |
| EP | 03 78 9946 | 7/2007 |

OTHER PUBLICATIONS

Zimmer-Faust et al. Biol. Bull. (1988), vol. 175, pp. 167-174.*
Wachowiak et al. J. Comp. Physiol A (1998), vol. 182, pp. 425-434.*
Bobanovic, L.K et al. "P2X Receptor Trafficking in Neurons is Subunit Specific" *J. Neurosci.* 22(12):4814-4824 (Jun. 15, 2002).
Sklar, P.B. et al. "The Odorant-Sensitive Adeenylate Cyclase of Olfactory Receptor Cells" *J Biol Chem* 261(33):15538-15543 (Nov. 25, 1986).
Akbar GKM, Dasari VR, Webb TE, Ayyanathan K, Pillarisetti K, Sandhu AK, Athwal RS, Daniel JL,Ashby B, Barnard EA, Kunapuli SP (1996) Molecular Cloning of a Novel P2 Purinoceptor from Human Erythroleukemia Cells. J Biol Chem 271: 18363-18367.
Ayyanathan K, Webbs TE, Sandhu AK, Athwal RS, Barnard EA and Kunapuli S (1996) Cloning and chromosomal localization of the human P2Y1 purinoceptor. Biochem Biophys Res Commun 218: 783-788.
Bean BP (1992) Pharmacology and electrophysiology of ATP-activated ion channels. Trends Pharmacol Sci 13: 87-90.
Bo X, Zhang Y, Nassar M, Burnstock G and Schöepfer R (1995) A P2X purinoceptor cDNA conferring a novel pharmacological profile. FEBS Lett 375: 129-133.
Bogdanov YD, Wildman SS, Clements MP, King BF and Burnstock G (1998) Molecular cloning and characterisation of rat $P2Y_4$ nucleotide receptor. Br J Pharmacol 124: 428-430.
Bowler WB, Birch MA, Gallagher JA and Bilbe G (1995) Identification and cloning of human $P_{2U}$ purinoceptor present in osteoclastoma, bone, and osteoblasts. J Bone Miner Res 10: 1137-1145.
Brake, A. J., Wagenbach, M. J., and Julius, D. (1994). New structural motif for ligand-gated ion channels defined by an ionotropic ATP receptor. Nature 371, 519-523.
Brandle, U., Spielmanns, P., Osteroth, R., Sim, J., Surprenant, A., Buell, G., Ruppersberg, J. P., Plinkert, P. K., Zenner, H. P., and Glowatzki, E. (1997). Desensitization of the $P2X_2$ receptor controlled by alternative splicing. FEBS Lett. 404, 294-298.
Buck L, Axel R (1991) A novel multigene family may encode odorant receptors: a molecular basis for odor recognition. Cell 65: 175-187.
Buell G, Lewis C, Collo G, North RA and Surprenant A (1996a) An antagonist-insensitive $P_{2X}$ receptor expressed in epithelia and brain. EMBO (Eur Mol Biol Organ) J 15: 55-62.
Buell G, Michel AD, Lewis C, Collo G, Humphrey PP and Surprenant A (1996b) $P2X_1$ receptor activation in HL60 cells. Blood 87: 2659-2664.
Callender, T. J., Morrow, L., Subramanian, K., Duhon, D., and Ristovv, M. (1993). Three-dimensional brain metabolic imaging in patients with toxic encephalopathy. Environ. Res. 60, 295-319.
Carr, V. M., Menco, B. P., Yankova, M. P., Morimoto, R. I., and Farbman, A. I. (2001). Odorants as cell-type specific activators of a heat shock response in the rate olfactory mucosa. J. Comp. Neurol. 432, 425-439.
Carr, W. E., Ache, B. W., and Gleeson, R. A. (1987). Chemoreceptors of crustaceans: similarities to receptors for neuroactive substances in internal tissues. Environ. Health Perspect. 71, 31-46.
Chang K, Hanaoka K, Kumada M and Takuwa Y (1995) Molecular cloning and functional analysis of a novel $P_2$ nucleotide receptor. J Biol Chem (Tokyo) 270: 26152-26158.
Chen C-C, Akopian AN, Sivilotti L, Colquhoun D, Burnstock G and Wood JN (1995a) A P2X purinoceptor expressed by a subset of sensory neurons. Nature (Lond.) 377: 428-431.
Chen ZP, Krull N, Xu S, Levy A and Lightman SL (1996b) Molecular cloning and functional characterization of a rat pituitary G protein-coupled ATP receptor. Endocrinology 137: 1833-1840.
Chiu P, Lynch JW, Barry PH (1997) Odorant-induced currents in intact patches from rat olfactory receptor neurons: theory and experiment. Biophys J 72: 1442-1457.
Collo G, North RA, Kawashima E, Merlo-Pich E, Neidhart S, Surprenant A and Buell G (1996) Cloning of $P2X_5$ and $P2X_6$ receptors and the distribution and properties of an extended family of ATP-gated ion channels. J Neurosci 16: 2495-2507.

(Continued)

Primary Examiner—Patrick T Lewis
(74) Attorney, Agent, or Firm—Ballard Spahr Andrews & Ingersoll LLP

(57) ABSTRACT

Disclosed are compositions and methods for modulating odor sensitivity, as well as screening methods for detecting compounds that modulate odor sensitivity.

13 Claims, 23 Drawing Sheets

OTHER PUBLICATIONS

Figure 1A:
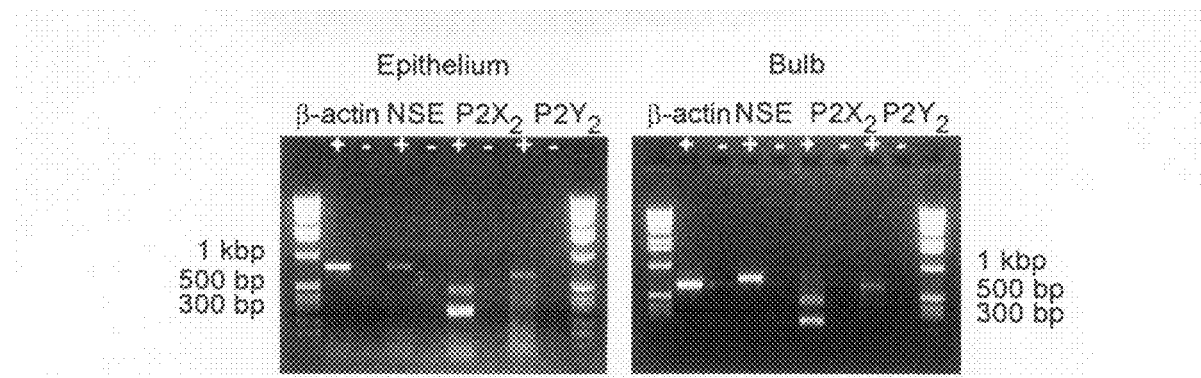
Figure 1B:
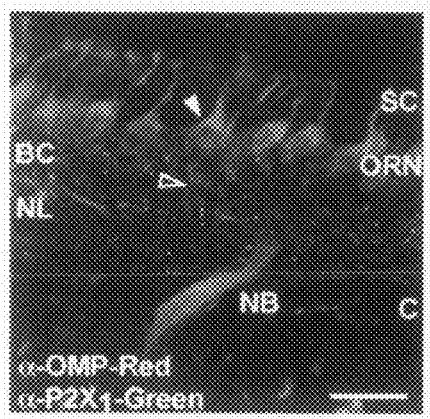
Figure 1C:
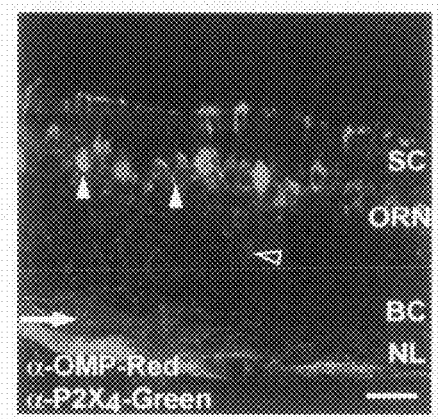

Communi D, Parmentier M and Boeynaems J-M (1996b) Cloning, functional expression and tissue distribution of the human $P2Y_6$ receptor. Biochem Biophys Res Commun 222: 303-308.

Communi D, Govaerts C, Parmentier M and Boeynaems JM (1997) Cloning of human purinergic P2Y receptor coupled to phospholipase C and adenylyl cyclase. J Biol Chem 272: 31969-31973.

Danaceau, J. P. and Lucero, M. T. (1998). Betaine activates a hyperpolarizing chloride conductance in squid olfactory receptor neurons. J. Comp. Physiol. [A] 183, 225-235.

Dubyak, G. R. and el-Moatassim, C. (1993). Signal transduction via P2-purinergic receptors for extracellular ATP and other nucleotides. Am. J. Physiol. 265, C577-C606.

Eisthen, H. L., Delay, R. J., Wirsig-Wiechmann, C. R., and Dionne, V. E. (2000). Neuromodulatory effects of gonadotropin releasing hormone on olfactory receptor neurons. J. Neurosci. 20, 3947-3955.

Erb L, Garrad R, Wang Y, Quinn T, Turner JT and Weisman GA (1995) Site-directed mutagenesis of $P_{2U}$ purinoceptors: Positively charged amino acids in transmembrane helices 6 and 7 affect agonist potency and specificity. J Biol Chem 270: 4185-4188.

Evans RJ and Kennedy C (1994) Characterization of $P_2$ purinoceptors in the smooth muscle of the rat tail artery: A comparison between contractile and electrophysiological responses. Br J Pharmacol 113: 853-860.

Fitz JG and Sostman AH (1994) Nucleotide receptors activate cation, potassium, and chloride currents in a liver cell line. Am J Physiol 266: G544-G553.

Finger, T. E., St.Jeor, V. L., Kinnamon, J. C., and Silver, W. L. (1990). Ultrastructure of substance P- and CGRP-immunoreactive nerve fibers in the nasal epithelium of rodents. J Comp. Neurol. 294, 293-305.

Frings, S. (1993). Protein kinase C sensitizes olfactory adenylate cyclase. J Gen. Physiol. 101, 183-205.

Garcia-Guzman M, Soto F, Gomez-Hernandez JM, Lund P-E and Stühmer W (1997a) Characterization of recombinant human $P2X_4$ receptor reveals pharmacological differences to the rat homologue. Mol Pharmacol 51: 109-118.

Garcia-Guzman M, Stühmer W and Soto F (1997b) Molecular characterization and pharmacological properties of the human $P2X^3$ purinoceptor. Mol Brain Res 47: 59-66.

GenBank Accession #M11931.
GenBank Accession #U09402.
GenBank Accession #U14414.
GenBank Accession #U56839.
GenBank Accession #X84896.

Getchell, M. L. and Getchell, T. V. (1992). Fine structural aspects of secretion and extrinsic innervation in the olfactory mucosa. Microsc. Res. Tech. 23, 111-127.

Getchell, T. V. (1986). Functional properties of vertebrate olfactory receptor neurons. Physiol. Rev. 66, 772-818.

Gödecke S, Decking UKM, Gödecke A and Schrader J (1996) Cloning of the rat $P_{2U}$ receptor and its potential role in coronary vasodilation. Am J Physiol 270: C570-C577.

Graziadei, P. P. C. (1971). The Olfactory Mucosa of Vertebrates. In Handbook of Sensory Physiology, L. M. Beidler, ed. (Berlin: Springer-Verlag), vol. IV, pp. 27-58.

Graziadei, P. P. C. and Monti-Graziadei, G. A. (1978). Continuous nerve cell nrenewal in the olfactory system. In Handbook of Sensory Physiology, M. Jacobson, ed. (New York: Springer), vol. IX, pp. 55-83.

Hegg CC, Lucero MT. (2002) Dopamine inhibits odor responsiveness and excitability in mouse oms. Abstract. Assoc. Chemo. Receptor Sci.

Henderson DJ, Elliot DG, Smith GM, Webb TE and Dainty IA (1995) Cloning and characterisation of a bovine $P_{2Y}$ receptor. Biochem Biophys Res Commun 212: 648-656.

Hoffmann C, Moro S, Nicholas RA, Harden TK, Jacobson KA. The role of amino acids in extracellular loops of the human $P2Y_1$ receptor in surface expression and activation processes. J Biol Chem. 1999 May 21;274(21):14639-47.

Hong K, Driscoll M. A transmembrane domain of the putative channel subunit MEC-4 influences mechanotransduction and neurodegeneration in *C. elegans*. Nature. Feb. 3, 1994;367(6462):470-3.

Honore, E., Martin, C., Mironneau, C., and Mironneau, J. (1989). An ATP-sensitive conductance in cultured smooth muscle cells from pregnant rat myometrium. Am. J. Physiol. 257, C297-C305.

Horn, R. and Marty, A. (1988). Muscarinic activation of ionic currents measured by a new whole-cell recording method. J. Gen. Physiol. 92, 145-159.

Illes, P., Klotz, K. N., and Lohse, M. J. (2000). Signaling by extracellular nucleotides and nucleosides. Naunyn Schmiedebergs Arch. Pharmacol. 362, 295-298.

Janssens R, Communi D, Pirotton S, Samson M, Parmentier M and Boeynaems J-M (1996) Cloning and tissue distribution of the human $P2Y_1$ receptor. Biochem Biophys Res Commun 221: 588-593.

Jiang Q, Guo D, Lee BX, Van Rhee Am, Kim Y-C, Nicholas RA, Schachter JB, Harden TK and Jacobson KA (1997) A mutational analysis of residues essential for ligand recognition at the human $P2Y_1$ receptor. Mol Pharmacol 52: 499-507.

Kang, J. and Caprio, J. (1995). In vivo responses of single olfactory receptor neurons in the channel catfish, *Ictalurus punctatus*. J. Neurophysiol. 73, 172-177.

Kilgour, J. D., Simpson, S. A., Alexander, D. J., and Reed, C. J. (2000). A rat nasal epithelial model for predicting upper respiratory tract toxicity: in vivo-in vitro correlations. Toxicology 145, 39-49.

Koshimizu, T. A., Van Goor, F., Tomic, M., Wong, A. O., Tanoue, A., Tsujimoto, G., and Stojikovic, S. S. (2000). Characterization of calcium signaling by purinergic receptor-channels expressed in excitable cells. Mol. Pharmacol. 58, 936-945.

Léon C, Vial C, Cazenave J-P and Gachet C (1996) Cloning and sequencing of a human cDNA encoding endothelial P2Y1 purinoceptor. Gene 171: 295-297.

Léon C, Hechler B, Vial C, Leray C, Cazenave J-P and Gachet C (1997) The $P2Y_1$ receptor is an ADP receptor antagonized by ATP and expressed in platelets and megakaryoblastic cells. FEBS Lett 403: 26-30.

Lewis C, Neidhart S, Holy C, North RA, Buell G and Surprenant A (1995) Coexpression of $P2X_2$ and $P2X_3$ receptor subunits can account for ATP-gated currents in sensory neurons. Nature (Lond.) 377: 432-435.

Longhurst PA, Schwegel T, Folander K and Swanson R (1996) The human $P_{2X1}$ receptor: Molecular cloning, tissue distribution, and localization to chromosome 17. Biochim Biophys Acta 1308: 185-188.

Lopez-Candales, A., Scott, M. J., and Wickline, S. A. (1995). Cholesterol feeding modulates spatial expression of TGF-$\beta$ 1 and $\beta$ 2 in aortas of Watanabe rabbits. Cytokine 7, 554-561.

Lowe, G. and Gold, G. H. (1993). Nonlinear amplification by calcium-dependent chloride channels in olfactory receptor cells. Nature 366, 283-286.

Lucero M, Piper D, Danaceau J, Squires A. Dopamine modulates odor responses in rat olfactory receptor neurons. Abstract. AChemS XVIII. 636-7.

Lustig KD, Shiau AK, Brake AJ and Julius D (1993) Expression cloning of an ATP receptor from mouse neuroblastoma cells. Proc Natl Acad Sci USA 90: 5113-5117.

Moro S, Guo D, Camaioni E, Boyer JL, Harden TK, Jacobson KA. Human $P2Y_1$ receptor: molecular modeling and site-directed mutagenesis as tools to identify agonist and antagonist recognition sites. J Med Chem. 1998 Apr. 23;41(9):1456-66.

Moro S, Hoffmann C, Jacobson KA. Role of the extracellular loops of G protein-coupled receptors in ligand recognition: a molecular modeling study of the human $P2Y_1$ receptor. Biochemistry. Mar. 23, 1999;38(12):3498-507.

Neary JT (1996) Trophic actions of extracellular ATP on astrocytes, synergistic interactions with fibroblast growth factors and underlying signal transduction mechanisms, in P2 Purinoceptors: Localization, Function and Transduction Mechanisms (Chadwick DJ and Goode JA eds) pp. 130-139, John Wiley & Sons, Chichester.

Neary, J. T., Rathbone, M. P., Cattabeni, F., Abbracchio, M. P., and Burnstock, G. (1996). Trophic actions of extracellular necleotides and nucleosides on glial and neuronal cells. Trends Neurosci. 19, 13-18.

Nguyen T, Erb L, Weisman GA, Marchese A, Heng HHQ, Garrad RC, George SR, Turner JT and O'Dowd BF (1996) Cloning, expression and chromosomal localization of the uridine nucleotide receptor gene. J Biol Chem (Tokyo) 270: 30845-30848.

Nicke A, Baumert HG, Rettinger J, Eichele A, Lambrecht G, Mutschier E and Schmalzing G (1998) $P2X_1$ and $P2X_3$ receptors form stable trimers: a novel structural motif of ligand-gated ion channels. EMBO Journal 17: 3016-3028.

North, R. A. and Barnard, E. A. (1997). Nucleotide receptors. Curr. Opin. Neurobiol. 7, 346-357.

North, R. A. and Surprenant, A. (2000). Pharmacology of cloned P2X receptors. Annu. Rev. Pharmacol. Toxicol. 40, 563-580.

Nuttle LC, el-Moatassim C and Dubyak GR (1993) Expression of the pore-forming $P_{2Z}$ purinoreceptor in Xenopus oocytes injected with poly(A)+ RNA from murine macrophages. Mol. Pharmacol 44: 93-101.

Pacaud P, Feolde E, Frelin C and Loirand G (1996) Characterization of the $P_{2Y}$-purinoceptor involved in the ATP-induced rise in cytosolic $Ca^{2+}$ concentration in rat ileal myocytes. Br J Pharmacol 118: 2213-2219.

Parr CE, Sullivan DM, Paradiso AM, Lazarowski ER, Burch LH, Olsen JC, Erb L, Weisman GA, Boucher RC and Turner JT (1995) Cloning and expression of a human $P_{2U}$ nucleotide receptor, a target for cystic fibrosis pharmacology. Proc Natl Acad Sci USA 91: 3275-3279.

Ralevic, V. and Burnstock, G. (1998). Receptors for purines and pyrimidines. Pharmacol. Rev. 50, 413-492.

Rassendren F, Buell GN, Virginio Co, Collo G, North RA and Surprenant A (1997) The permeabilizing ATP receptor, P2X7. J Biol Chem 272: 5482-5486.

Rice WR, Burton FM and Fiedeldey DT (1995) Cloning and expression of the alveolar Type II cell $P_{2U}$- purinergic receptor. Am J Respir Cell Mol Biol 12: 27-32.

Roman, R. M., Wang, Y., Lidofsky, S. D., Feranchak, A. P., Lomri, N., Scharschmidt, B. F., and Fitz, J. G. (1997). Hepatocellular ATP-binding cassette protein expression enhances ATP release and autocrine regulation of cell volume. J. Biol. Chem. 272, 21970-21976.

Schachter JB, Li Q, Boyer JL, Nicholas RA and Harden TK (1996) Second messenger cascade specificity and pharmacological selectivity of the human $P_{2Y1}$-purinoceptor. Br J Pharmacol 118: 167-173.

Schild D, Restrepo D. Transduction mechanisms in vertebrate olfactory receptor cells. Physiol Rev. Apr. 1998;78(2):429-66.

Schwiebert, E. M. and Kishore, B. K. (2001). Extracellular nucleotide signaling along the renal epithelium. Am. J. Physiol. Renal Physiol. 280, F945-F963.

Séguéla P, Haghighi A, Soghomonian J-J and Cooper E (1996) A novel neuronal $P_{2X}$ ATP receptor ion channel with widespread distribution in the brain. J Neurosci 16: 448-455.

Simon J, Kidd EJ, Smith FM, Chessell IP, Murrell-Lagnado R, Humphrey PPA and Barnard EA (1997) Localization and functional expression of splice variants of the $P2X_2$ receptor. Mol Pharmacol 52: 237-248.

Soto F, Garcia-Guzman M, Gomez-Hernandez JM, Hollmann M, Karschin C and Stühmer P (1996a) $P2X_4$: An ATP-activated ionotropic receptor cloned from rat brain. Proc Natl Acad Sci USA 93: 3684-3688.

Soto F, Garcia-Guzman M, Karschin C and Stühmer W (1996b) Cloning and tissue distribution of a novel $P2_X$ receptor from rat brain. Biochem Biophys Res Commun 223: 456-460.

Southey MC, Hammet F, Hutchins AM, Paidhungat M, Somers GR and Venter DJ (1996) Molecular cloning and sequencing of a novel human P2 nucleotide receptor. Biochim Biophys Acta 1309: 77-80.

Surprenant A, Rassendren FA, Kawashima E, North RA and Buell G (1996) The cytolytic $P_{2Z}$ receptor for extracellular ATP identified as a $P_{2X}$ receptor ($P2X_7$). Science (Wash. DC) 272: 735-738.

Stam NJ, Klomp J, Van De Heuvel M and Olijve W (1996) Molecular cloning and characterization of a novel orphan receptor ($P_{2P}$) expressed in human pancreas that shows high structural homology to the $P_{2U}$ purinoceptor. Febs Lett 384: 260-264.

Thorne, P. R. and Housley, G. D. (1996). Purinergic signalling in sensory systems. Seminars Neurosci. 8 , 233-246.

Tokuyama Y, Hara M, Jones EMC, Fan Z and Bell GI (1995) Cloning of rat and mouse $P_{2Y}$ purinoceptors. Biochem Biophys Res Commun 211: 211-218.

Valera S, Hussy N, Evans RJ, Adami N, North RA, Surprenant A and Buell G (1994) A new class of ligand-gated ion channel defined by $P_{2X}$ receptor for extracellular ATP. Nature (Lond.) 371: 516-519.

Valera S, Talbot F, Evans RJ, Gos A, Antonarakis SE, Morris MA and Buell GN (1995) Characterization and chromosomal localization of a human $P_{2X}$ receptor from the urinary bladder. Receptors Channels 3: 283-289.

Van Rhee AM, Fischer B, Van Galen PJM and Jacobson KA (1995) Modelling the $P_{2Y}$ purinoceptor using rhodopsin as template. Drug Des Discov 13: 133-154.

Vargas, G. and Lucero, M. T. (1999a). A method for maintaining odor-responsive adult rat olfactory receptor neurons in short-term culture. Chem. Senses 24, 211-216.

Vargas, G. and Lucero, M. T. (1999b). Dopamine modulates inwardly rectifying hyperpolarization-activated current ($Ih$) in cultured rat olfactory receptor neurons. J. Neurophysiol. 81, 149-158.

Wang C-Z, Namba N, Gonoi T, Inagaki N and Seino S (1996) Cloning and pharmacological characterization of a fourth P2X receptor subtype widely expressed in brain and peripheral tissues including various endocrine tissues. Biochem Biophys Res Commun 220: 196-202.

Webb TE, Simon J, Krishek BJ, Bateson AN, Smart TG, King BF, Burnstock G and Barnard EA (1993b) Cloning and functional expression of a brain G-protein-coupled ATP receptor. FEBS Lett 324: 219-225.

Webb TE, Henderson D, King BF, Wang S, Simon J, Bateson AN, Burnstock G and Barnard EA (1996a) A novel G protein-coupled $P_2$ purinoceptor ($P_{2Y3}$) activated preferentially by nucleoside diphosphates. Mol Pharmacol 50: 258-265.

Wetzel, C. H., Spehr, M., and Hatt, H. (2001). Phosphorylation of voltage-gated ion channels in rat olfactory receptor neurons. Eur. J. Neurosci. 14, 1056-1064.

Windscheif U (1996) Purinoceptors: From history to recent progress: A review. J Pharm Pharmacol 48: 993-1011.

Zufall, F., Shepherd, G. M., and Firestein, S. (1991). Inhibition of the olfactory cyclic nucleotide gated ion channel by intracellular calcium. Proc. R. Soc. Lond. B Biol. Sci. 246, 225-230.

* cited by examiner

FIG.7A

```
P2X1  VRESGQDFRSLAEKGGVVGITIDWKCDLDWHVRHCKPIYQFHGLYG---EKNLSPGFNFR      292
P2X2  VEKAGENFTELAHKGGVIGVIINWNCDLDLSESECNPKYSFRRLDP--KYDPASSGYNFR     290
P2X3  VKFAGQDFAKLARTGGVLGIKIGWVCDLGWCDLDKAWDQCIPKYSFSRLDGVSEKSSVSPGYNFR 281
P2X4  VEDAGHSFQEMAVEGGIMGIQIKWDCNLDRAASLCLPRYSFRRLDTRDLEHNVSPGYNFR    295
P2X5  VRWAGADFQDIALKGGVIGIYIEWDCDLDKAASKCNPHYFNRLDN-KHTHSISSGYNFR      296
P2X6  VAMTGDEEDEDLALLGGAVGINIHMDCNLDTKGSDCSPQYSF-QLQE---------RGYNFR   289
              (H5)                                    M2
P2X1  FARHFVQ-NGTNRHLFKVFGIHFDILVDGKAGKFDITPTMTTIGSGIGIFGVATVLCDL      351
P2X2  FAKYYKINGTTTTRILLKAYGIRIDVIVHGQAGKFSLIPTIINLATALTSIGVGSFLCDW      350
P2X3  FAKYYKMENGSEYRTILLKAFGIRFDVLVYGNAGKFNIIPTIISSVAAFTSVGVGTVLCDI     341
P2X4  FAKYYRDLAGKEQRTLIKAYGIRFDIIVFGKAGKFDIITPTMINVGSGLALLGVATVLCDV    355
P2X5  FARYYRDPNGVEFRDLMKAYGIRFDVIVNGKAGKFSIIPTVINIGSGLALMCAGAFFCDL     356
P2X6  TANYMWAASGVESRSLLKLYGIRFDILVTGQAGKFALIPTAITVGTGAAMLGWVTFLCDL     349
P2X1  LLLHILPKRHYNQKQKF-KYAEDMGPGEGEHDPVATSSTLGLQENMRTS---------      399
P2X2  ILLTFMNKNKLYSHKKFDKVRTPKHPSSRWPVTLALVGQIPPPPHSYSDQPPSPPSGE        410
P2X3  ILLNFLKGADHYKARKFEEVTETTLKGTASTNPVFASDQATVEKQSTDSGAYSIGH------    397
P2X4  IVLYCMKKKYYYRDKKY-KYVEDYEQGLSGEMNQ-----------------                388
P2X5  VLIYLIRKSEFYRDKKFEKVRGQKEDANVEVEANEMEQERPEDEPLERVRQDEQSQELAQ     416
P2X6  LLLYVDREAGFWRTKYEEARAPKATTNSA----------------                    379
P2X1  ---------------------------------------                         399
P2X2  GPTLGEGAELPLAVQSPRPCSISALTEQVVDTLGQHMGQRPPVPEPSQQDSTSTDPKGLAQL   472
P2X3  ---------------------------------------                         397
P2X4  ---------------------------------------                         388
P2X5  SGRKQNSNCQVLLEPARFGLRENAIVNVKQSQILHPVKT--                        455
P2X6  ---------------------------------------                         379
```

FIG. 7B

TM 3
P2Y1  (ADP) 125    KLQRFIFHVNLYGSILFLTCISAHR   149
P2Y2  (UTP) 107    KLVRFLFYTNLYCSILFLTCISVHR   131
P2Y4  (UTP) 109    KFVRFLFYWNLYCSVLFLTCISVHR   133
P2Y6  (UDP) 100    RLVRFLFYANLAGSILFLTCISFQR   124
P2Y11 (ATP) 100    RLERFLFTCNLLCSVIFITCISLNR   124

TM 5
P2Y1  (ADP) 215    FIYSMCTTVAMECVFLVLILGCYGLIV  241
P2Y2  (UTP) 196    VAYSSVNLGLLFAVFFAVILVCYVLMA  222
P2Y4  (UTP) 198    VKFSSAVMGLLFGVFCLVTLVCYGLMA  224
P2Y6  (UDP) 190    MPYGMALTVICFLLFFAALLACYCLLA  215
P2Y11 (ATP) 200    RAYSLVLAGLGCGLFLLLTLAAYGALG  226

TM 6
P2Y1  (ADP) 260    YLVIIVLTVFAVSYIPPHVMKTMNLR   285
P2Y2  (UTP) 245    RTIAVVLAVFALCFLPFHVTRTLYYS   270
P2Y4  (UTP) 245    RTIAVVLTVFAVCFVPFHITRTIYYL   270
P2Y6  (UDP) 239    RMAVVVAAAFAISFLPFHITKTAYLA   264
P2Y11 (ATP) 245    ALVASGVALYASSYVPYHIMRVINVD   270

TM7
P2Y1  (ADP) 303    YATYQVTRGLASLNSCVDPILYPLAGDT  330
P2Y2  (UTP) 285    NMAYKVTRFLASANSCLDPVLYFLAGQR  312
P2Y4  (UTP) 285    NVVYKVTRFLASANSCLDPVLYLLTGDK  312
P2Y6  (UDP) 280    AAAYKGTRFFASANSVLDPILFYFTQKK  307
P2Y11 (ATP) 297    YVGYQVMRGLMPLASCVHPLLYMAAUPS 324

FIG.10

Figure 11B:
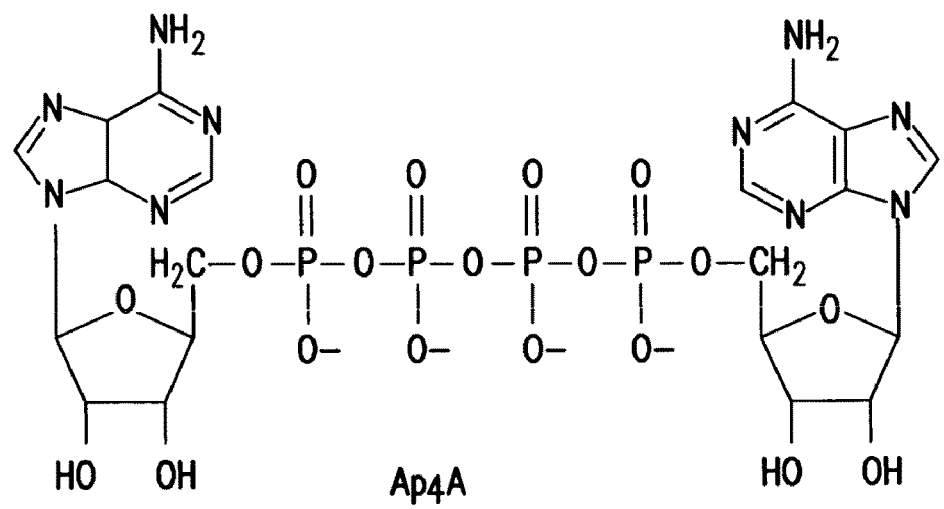

AGONISTS
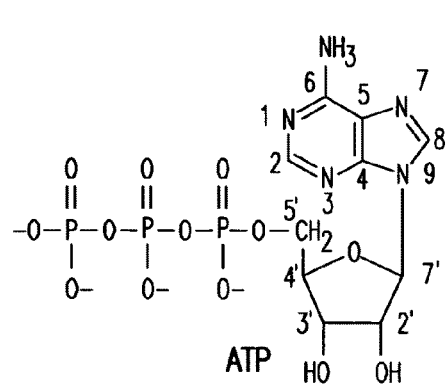
ATP
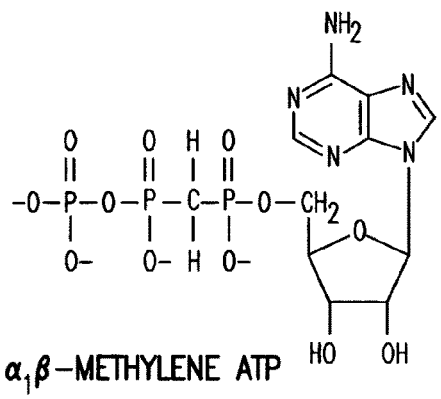
α,β-METHYLENE ATP
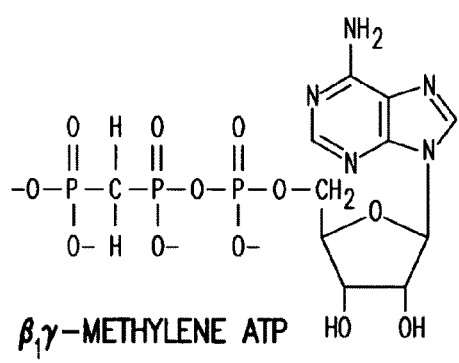
β,γ-METHYLENE ATP
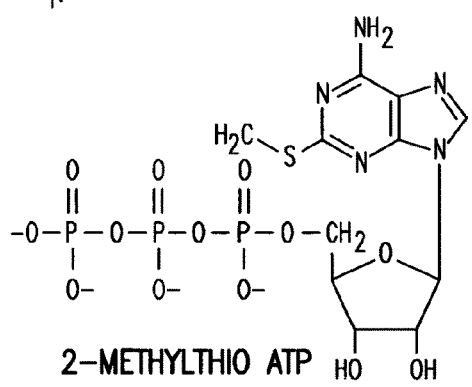
2-METHYLTHIO ATP
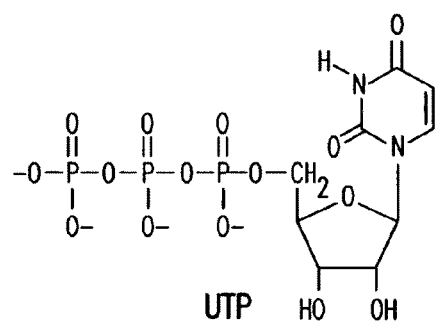
UTP
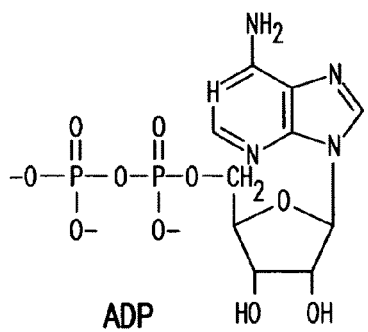
ADP
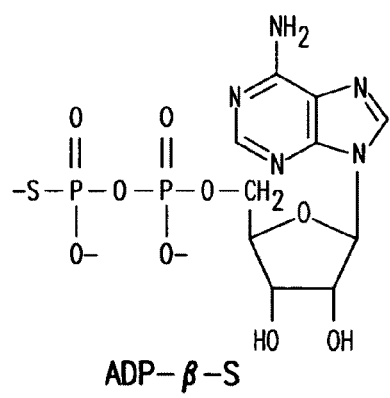
ADP-β-S
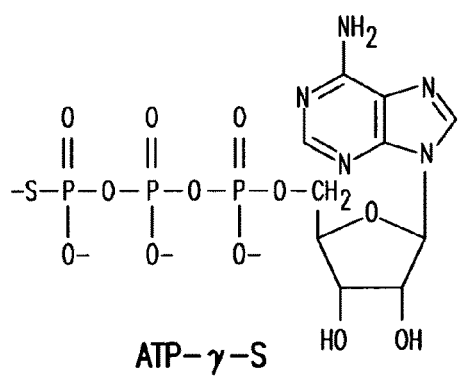
ATP-γ-S
FIG. 11A

AGONISTS (CONT'D)

Ap4A

SEQUENCE LISTING

<160> NUMBER OF SEQ ID NOS: 26

<210> SEQ ID NO 1
<211> LENGTH: 1452
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 1

```
gaattcggct gatcccgcgg caggtgctag caggagctgg cagcatgggc tccccagggg      60
ctacgacagg ctgggggctt ctggattata agacggagaa gtatgtgatg accaggaact     120
ggcgggtggg cgccctgcag aggctgctgc agtttgggat cgtggtctat gtggtagggt     180
gggctctcct cgccaaaaaa ggctaccagg agcgggacct ggaacccag ttttccatca     240
tcaccaaact caaagggggtt ccgtcactc agatcaagga gcttggaaac cggctgtggg     300
atgtggccga cttcgtgaag ccacctcagg agagaacgt gttcttcttg gtgaccaact     360
tccttgtgac gccagcccaa gttcagggca gatgcccaga gcacccgtcc gtcccactgg     420
ctaactgctg ggtcgacgaa gactgccccg aaggggaggg aggcacacac agccacggtg     480
taaaaacagg ccagtgtgtg gtgttcaatg ggacccacag gacctgtgag atctggagtt     540
ggtgcccagt ggagagtggc gttgtgccct cgaggcccct gctggcccag cccagaact     600
tcacactgtt catcaaaaac acagtcacct tcagcaagtt caacttctct aagtccaatg     660
ccttggagac ctgggacccc acctatttta agcactgccg ctatgaacca caattcagcc     720
cctactgtcc cgtgttccgc attggggacc tcgtggccaa ggctggaggg accttcgagg     780
acctggcgtt gctgggtggc tctgtaggca tcagagttca ctgggattgt gacctggaca     840
ccggggactc tggctgctgg cctcactact ccttccagct gcaggagaag agctacaact     900
tcaggacagc cactcactgg tgggagcaac cgggtgtgga ggcccgcacc ctgctcaagc     960
tctatggaat ccgcttcgac atcctcgtca ccgggcaggc agggaagttc gggctcatcc    1020
ccacggccgt cacactgggc accggggcag cttggctggg cgtggtcacc ttttttctgtg    1080
acctgctact gctgtatgtg gatagagaag cccatttcta ctggaggaca agtatgagg    1140
aggccaaggc cccgaaagca accgccaact ctgtgtggag ggagctggcc tttgcatccc    1200
aagcccgact ggccgagtgc ctcagacgga gctcagcacc tgcacccacg gccactgctg    1260
ctgggagtca gacacagaca ccaggatggc cctgtccaag ttctgacacc cacttgccaa    1320
cccattccgg gagcctgtag ccgtttccct gctggttgag aagagagagg ggctgggcaa    1380
ggaaggaccc ctgccctgcc gagcgaaagc aaggatgagg caacagcaat gaaagaagat    1440
```
caagccgaat tc                                                        1452

<210> SEQ ID NO 2
<211> LENGTH: 399
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 2

```
Met Ala Arg Arg Phe Gln Glu Glu Leu Ala Ala Phe Leu Phe Glu Tyr
 1               5                  10                  15

Asp Thr Pro Arg Met Val Leu Val Arg Asn Lys Lys Val Gly Val Ile
            20                  25                  30

Phe Arg Leu Ile Gln Leu Val Val Leu Val Tyr Val Ile Gly Trp Val
        35                  40                  45

Phe Leu Tyr Glu Lys Gly Tyr Gln Thr Ser Ser Gly Leu Ile Ser Ser
    50                  55                  60

Val Ser Val Lys Leu Lys Gly Leu Ala Val Thr Gln Leu Pro Gly Leu
65                  70                  75                  80

Gly Pro Gln Val Trp Asp Val Ala Asp Tyr Val Phe Pro Ala Gln Gly
                85                  90                  95

Asp Asn Ser Phe Val Val Met Thr Asn Phe Ile Val Thr Pro Lys Gln
            100                 105                 110

Thr Gln Gly Tyr Cys Ala Glu His Pro Glu Gly Gly Ile Cys Lys Glu
        115                 120                 125

Asp Ser Gly Cys Thr Pro Gly Lys Ala Lys Arg Lys Ala Gln Gly Ile
    130                 135                 140

Arg Thr Gly Lys Cys Val Ala Phe Asn Asp Thr Val Lys Thr Cys Glu
145                 150                 155                 160

Ile Phe Gly Trp Cys Pro Val Glu Val Asp Asp Ile Pro Arg Pro
                165                 170                 175

Ala Leu Leu Arg Glu Ala Glu Asn Phe Thr Leu Phe Ile Lys Asn Ser
            180                 185                 190

Ile Ser Phe Pro Arg Phe Lys Val Asn Arg Arg Asn Leu Val Glu Glu
        195                 200                 205

Val Asn Ala Ala His Met Lys Thr Cys Leu Phe His Lys Thr Leu His
    210                 215                 220

Pro Leu Cys Pro Val Phe Gln Leu Gly Tyr Val Val Gln Glu Ser Gly
225                 230                 235                 240

Gln Asn Phe Ser Thr Leu Ala Glu Lys Gly Gly Val Val Gly Ile Thr
                245                 250                 255

Ile Asp Trp His Cys Asp Leu Asp Trp His Val Arg His Cys Arg Pro
            260                 265                 270

Ile Tyr Glu Phe His Gly Leu Tyr Glu Glu Lys Asn Leu Ser Pro Gly
        275                 280                 285

Phe Asn Phe Arg Phe Ala Arg His Phe Val Glu Asn Gly Thr Asn Tyr
    290                 295                 300

Arg His Leu Phe Lys Val Phe Gly Ile Arg Phe Asp Ile Leu Val Asp
305                 310                 315                 320

Gly Lys Ala Gly Lys Phe Asp Ile Ile Pro Thr Met Thr Thr Ile Gly
                325                 330                 335

Ser Gly Ile Gly Ile Phe Gly Val Ala Thr Val Leu Cys Asp Leu Leu
            340                 345                 350
```

| Leu | Leu | His | Ile | Leu | Pro | Lys | Arg | His | Tyr | Tyr | Lys | Gln | Lys | Lys | Phe |
|---|---|---|---|---|---|---|---|---|---|---|---|---|---|---|---|
| | | | | 355 | | | | | 360 | | | | | 365 | |

| Lys | Tyr | Ala | Glu | Asp | Met | Gly | Pro | Gly | Ala | Ala | Glu | Arg | Asp | Leu | Ala |
|---|---|---|---|---|---|---|---|---|---|---|---|---|---|---|---|
| 370 | | | | | 375 | | | | | 380 | | | | | |

| Ala | Thr | Ser | Ser | Thr | Leu | Gly | Leu | Gln | Glu | Asn | Met | Arg | Thr | Ser |
|---|---|---|---|---|---|---|---|---|---|---|---|---|---|---|
| 385 | | | | | 390 | | | | | 395 | | | | |

<210> SEQ ID NO 3
<211> LENGTH: 1452
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 3

| | | | | | |
|---|---|---|---|---|---|
| gaattcggct | gatcccgcgg | caggtgctag | caggagctgg | cagcatgggc | tccccagggg | 60 |
| ctacgacagg | ctgggggctt | ctggattata | agacggagaa | gtatgtgatg | accaggaact | 120 |
| ggcgggtggg | cgccctgcag | aggctgctgc | agtttgggat | cgtggtctat | gtggtagggt | 180 |
| gggctctcct | cgccaaaaaa | ggctaccagg | agcgggacct | ggaaccccag | ttttccatca | 240 |
| tcaccaaact | caaaggggtt | tccgtcactc | agatcaagga | gcttggaaac | cggctgtggg | 300 |
| atgtggccga | cttcgtgaag | ccacctcagg | agagaacgt | gttcttcttg | gtgaccaact | 360 |
| tccttgtgac | gccagcccaa | gttcagggca | gatgcccaga | gcacccgtcc | gtcccactgg | 420 |
| ctaactgctg | ggtcgacgaa | gactgccccg | aaggggaggg | aggcacacac | agccacggtg | 480 |
| taaaaacagg | ccagtgtgtg | gtgttcaatg | gacccacag | gacctgtgag | atctggagtt | 540 |
| ggtgcccagt | ggagagtggc | gttgtgccct | cgaggcccct | gctggcccag | gcccagaact | 600 |
| tcacactgtt | catcaaaaac | acagtcacct | tcagcaagtt | caacttctct | aagtccaatg | 660 |
| ccttggagac | ctgggacccc | acctatttta | agcactgccg | ctatgaacca | caattcagcc | 720 |
| cctactgtcc | cgtgttccgc | attggggacc | tcgtggccaa | ggctggaggg | accttcgagg | 780 |
| acctggcgtt | gctgggtggc | tctgtaggca | tcagagttca | ctgggattgt | gacctggaca | 840 |
| ccggggactc | tggctgctgg | cctcactact | ccttccagct | gcaggagaag | agctacaact | 900 |
| tcaggacagc | cactcactgg | tgggagcaac | cgggtgtgga | ggcccgcacc | ctgctcaagc | 960 |
| tctatggaat | ccgcttcgac | atcctcgtca | ccgggcaggc | agggaagttc | gggctcatcc | 1020 |
| ccacggccgt | cacactgggc | accggggcag | cttggctggg | cgtggtcacc | tttttctgtg | 1080 |
| acctgctact | gctgtatgtg | gatagagaag | cccatttcta | ctggaggaca | agtatgagg | 1140 |
| aggccaaggc | cccgaaagca | accgccaact | ctgtgtggag | ggagctggcc | tttgcatccc | 1200 |
| aagcccgact | ggccgagtgc | ctcagacgga | gctcagcacc | tgcacccacg | gccactgctg | 1260 |
| ctgggagtca | gacacagaca | ccaggatggc | cctgtccaag | ttctgacacc | cacttgccaa | 1320 |
| cccattccgg | gagcctgtag | ccgtttccct | gctggttgag | aagagagagg | ggctgggcaa | 1380 |
| ggaaggaccc | ctgccctgcc | gagcgaaagc | aaggatgagg | caacagcaat | gaaagaagat | 1440 |
| caagccgaat | tc | | | | | 1452 |

<210> SEQ ID NO 4
<211> LENGTH: 472
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 4

```
Met Val Arg Arg Leu Ala Arg Gly Cys Trp Ser Ala Phe Trp Asp Tyr
1               5                   10                  15
Glu Thr Pro Lys Val Ile Val Arg Asn Arg Arg Leu Gly Phe Val
            20                  25                  30
His Arg Met Val Gln Leu Leu Ile Leu Leu Tyr Phe Val Trp Tyr Val
            35                  40                  45
Phe Ile Val Gln Lys Ser Tyr Gln Asp Ser Glu Thr Gly Pro Glu Ser
50                  55                  60
Ser Ile Ile Thr Lys Val Lys Gly Ile Thr Met Ser Glu Asp Lys Val
65                  70                  75                  80
Trp Asp Val Glu Glu Tyr Val Lys Pro Pro Glu Gly Gly Ser Val Val
                85                  90                  95
Ser Ile Ile Thr Arg Ile Glu Val Thr Pro Ser Gln Thr Leu Gly Thr
                100                 105                 110
Cys Pro Glu Ser Met Arg Val His Ser Ser Thr Cys His Ser Asp Asp
            115                 120                 125
Asp Cys Ile Ala Gly Gln Leu Asp Met Gln Gly Asn Gly Ile Arg Thr
130                 135                 140
Gly His Cys Val Pro Tyr Tyr His Gly Asp Ser Lys Thr Cys Glu Val
145                 150                 155                 160
Ser Ala Trp Cys Pro Val Glu Asp Gly Thr Ser Asp Asn His Phe Leu
                165                 170                 175
Gly Lys Met Ala Pro Asn Phe Thr Ile Leu Ile Lys Asn Ser Ile His
            180                 185                 190
Tyr Pro Lys Phe Lys Phe Ser Lys Gly Asn Ile Ala Ser Gln Lys Ser
            195                 200                 205
Asp Tyr Leu Lys His Cys Thr Phe Asp Gln Asp Ser Asp Pro Tyr Cys
210                 215                 220
Pro Ile Phe Arg Leu Gly Phe Ile Val Glu Lys Ala Gly Glu Asn Phe
225                 230                 235                 240
Thr Glu Leu Ala His Lys Gly Gly Val Ile Gly Val Ile Ile Asn Trp
                245                 250                 255
Asn Cys Asp Leu Asp Leu Ser Glu Ser Glu Cys Asn Pro Lys Tyr Ser
            260                 265                 270
Phe Arg Arg Leu Asp Pro Lys Tyr Asp Pro Ala Ser Ser Gly Tyr Asn
            275                 280                 285
Phe Arg Phe Ala Lys Tyr Tyr Lys Ile Asn Gly Thr Thr Thr Arg
290                 295                 300
Thr Leu Ile Lys Ala Tyr Gly Ile Arg Ile Asp Val Ile Val His Gly
305                 310                 315                 320
Gln Ala Gly Lys Phe Ser Leu Ile Pro Thr Ile Ile Asn Leu Ala Thr
                325                 330                 335
Ala Leu Thr Ser Ile Gly Val Gly Ser Phe Leu Cys Asp Trp Ile Leu
            340                 345                 350
Leu Thr Phe Met Asn Lys Asn Lys Leu Tyr Ser His Lys Lys Phe Asp
            355                 360                 365
Lys Val Arg Thr Pro Lys His Pro Ser Ser Arg Trp Pro Val Thr Leu
    370                 375                 380
Ala Leu Val Leu Gly Gln Ile Pro Pro Pro Ser His Tyr Ser Gln
385                 390                 395                 400
Asp Gln Pro Pro Ser Pro Pro Ser Gly Glu Gly Pro Thr Leu Gly Glu
```

```
                        405                 410                 415
Gly Ala Glu Leu Pro Leu Ala Val Gln Ser Pro Arg Pro Cys Ser Ile
            420                 425                 430

Ser Ala Leu Thr Glu Gln Val Val Asp Thr Leu Gly Gln His Met Gly
        435                 440                 445

Gln Arg Pro Pro Val Pro Glu Pro Ser Gln Gln Asp Ser Thr Ser Thr
    450                 455                 460

Asp Pro Lys Gly Leu Ala Gln Leu
465                 470

<210> SEQ ID NO 5
<211> LENGTH: 1452
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 5
gaattcggct gatcccgcgg caggtgctag caggagctgg cagcatgggc tccccagggg      60
ctacgacagg ctgggggctt ctggattata agacggagaa gtatgtgatg accaggaact     120
ggcgggtggg cgccctgcag aggctgctgc agtttgggat cgtggtctat gtggtagggt     180
gggctctcct cgccaaaaaa ggctaccagg agcgggacct ggaaccccag ttttccatca     240
tcaccaaact caaaggggtt ccgtcactc agatcaagga gcttggaaac cggctgtggg     300
atgtggccga cttcgtgaag ccacctcagg agagaacgt gttcttcttg gtgaccaact     360
tccttgtgac gccagcccaa gttcagggca gatgcccaga gcacccgtcc gtcccactgg     420
ctaactgctg ggtcgacgaa gactgccccg aaggggaggg aggcacacac agccacggtg     480
taaaaacagg ccagtgtgtg gtgttcaatg ggacccacag gacctgtgag atctggagtt     540
ggtgcccagt ggagagtggc gttgtgccct cgaggcccct gctggcccag gcccagaact     600
tcacactgtt catcaaaaac acagtcacct tcagcaagtt caacttctct aagtccaatg     660
ccttggagac ctgggacccc acctatttta agcactgccg ctatgaacca caattcagcc     720
cctactgtcc cgtgttccgc attggggacc tcgtggccaa ggctggaggg accttcgagg     780
acctggcgtt gctgggtggc tctgtaggca tcagagttca ctgggattgt gacctggaca     840
ccggggactc tggctgctgg cctcactact ccttccagct gcaggagaag agctacaact     900
tcaggacagc cactcactgg tgggagcaac cgggtgtgga ggcccgcacc ctgctcaagc     960
tctatggaat ccgcttcgac atcctcgtca ccgggcaggc agggaagttc gggctcatcc    1020
ccacggccgt cacactgggc accggggcag cttggctggg cgtggtcacc tttttctgtg    1080
acctgctact gctgtatgtg gatagagaag cccatttcta ctggaggaca agtatgagg    1140 aggccaaggc cccgaaagca accgccaact ctgtgtggag ggagctggcc tttgcatccc    1200
aagcccgact ggccgagtgc ctcagacgga gctcagcacc tgcacccacg ccactgctg    1260 ctgggagtca gacacagaca ccaggatggc cctgtccaag ttctgacacc cacttgccaa    1320
cccattccgg gagcctgtag ccgtttccct gctggttgag aagagagagg ggctgggcaa    1380
ggaaggaccc ctgccctgcc gagcgaaagc aaggatgagg caacagcaat gaaagaagat    1440
caagccgaat tc                                                        1452

<210> SEQ ID NO 6
<211> LENGTH: 397
<212> TYPE: PRT
```

<213> ORGANISM: Artificial Sequence
<220> FEATURE:
<223> OTHER INFORMATION: Description of Artificial Sequence:/note = synthetic construct

<400> SEQUENCE: 6

```
Met Asn Cys Ile Ser Asp Phe Phe Thr Tyr Glu Thr Thr Lys Ser Val
 1               5                  10                  15

Val Val Lys Ser Trp Thr Ile Gly Ile Ile Asn Arg Val Val Gln Leu
                20                  25                  30

Leu Ile Ile Ser Tyr Phe Val Gly Trp Val Phe Leu His Glu Lys Ala
            35                  40                  45

Tyr Gln Val Arg Asp Thr Ala Ile Glu Ser Ser Val Val Thr Lys Val
 50                  55                  60

Lys Gly Ser Gly Leu Tyr Ala Asn Arg Val Met Asp Val Ser Asp Tyr
 65                  70                  75                  80

Val Thr Pro Pro Gln Gly Thr Ser Val Phe Val Ile Ile Thr Lys Met
                85                  90                  95

Ile Val Thr Glu Asn Gln Met Gln Gly Phe Cys Pro Glu Ser Glu Glu
            100                 105                 110

Lys Tyr Arg Cys Val Ser Asp Ser Gln Cys Gly Pro Glu Pro Leu Pro
        115                 120                 125

Gly Gly Gly Ile Leu Thr Gly Arg Cys Val Asn Tyr Ser Ser Val Leu
    130                 135                 140

Arg Thr Cys Glu Ile Gln Gly Trp Cys Pro Thr Glu Val Asp Thr Val
145                 150                 155                 160

Glu Thr Pro Ile Met Met Glu Ala Glu Asn Phe Thr Ile Phe Ile Lys
                165                 170                 175

Asn Ser Ile Arg Phe Pro Leu Phe Asn Phe Glu Lys Gly Asn Leu Leu
            180                 185                 190

Pro Asn Leu Thr Ala Arg Asp Met Lys Thr Cys Arg Phe His Pro Asp
        195                 200                 205

Lys Asp Pro Phe Cys Pro Ile Leu Arg Val Gly Asp Val Val Lys Phe
    210                 215                 220

Ala Gly Gln Asp Phe Ala Lys Leu Ala Arg Thr Gly Gly Val Leu Gly
225                 230                 235                 240

Ile Lys Ile Gly Trp Val Cys Asp Leu Asp Lys Ala Trp Asp Gln Cys
                245                 250                 255

Ile Pro Lys Tyr Ser Phe Thr Arg Leu Asp Ser Val Ser Glu Lys Ser
            260                 265                 270

Ser Val Ser Pro Gly Tyr Asn Phe Arg Phe Ala Lys Tyr Tyr Lys Met
        275                 280                 285

Glu Asn Gly Ser Glu Tyr Arg Thr Leu Leu Lys Ala Phe Gly Ile Arg
    290                 295                 300

Phe Asp Val Leu Val Tyr Gly Asn Ala Gly Lys Phe Asn Ile Ile Pro
305                 310                 315                 320

Thr Ile Ile Ser Ser Val Ala Ala Phe Thr Ser Val Gly Val Gly Thr
                325                 330                 335

Val Leu Cys Asp Ile Ile Leu Leu Asn Phe Leu Lys Gly Ala Asp Gln
            340                 345                 350

Tyr Lys Ala Lys Lys Phe Glu Glu Val Asn Glu Thr Thr Leu Lys Ile
        355                 360                 365

Ala Ala Leu Thr Asn Pro Val Tyr Pro Ser Asp Gln Thr Thr Ala Glu
    370                 375                 380
```

Lys Gln Ser Thr Asp Ser Gly Ala Phe Ser Ile Gly His
385                 390                 395

<210> SEQ ID NO 7
<211> LENGTH: 1452
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 7

| | |
|---|---:|
| gaattcggct gatcccgcgg caggtgctag caggagctgg cagcatgggc tccccagggg | 60 |
| ctacgacagg ctgggggctt ctggattata agacggagaa gtatgtgatg accaggaact | 120 |
| ggcgggtggg cgcccctgcag aggctgctgc agtttgggat cgtggtctat gtggtagggt | 180 |
| gggctctcct cgccaaaaaa ggctaccagg agcgggacct ggaaccccag ttttccatca | 240 |
| tcaccaaact caaaggggtt tccgtcactc agatcaagga gcttggaaac cggctgtggg | 300 |
| atgtggccga cttcgtgaag ccacctcagg agagaacgt gttcttcttg gtgaccaact | 360 |
| tccttgtgac gccagcccaa gttcagggca gatgcccaga gcacccgtcc gtcccactgg | 420 |
| ctaactgctg ggtcgacgaa gactgccccg aaggggaggg aggcacacac agccacggtg | 480 |
| taaaaacagg ccagtgtgtg tgttcaatg ggacccacag gacctgtgag atctggagtt | 540 |
| ggtgcccagt ggagagtggc gttgtgccct cgaggcccct gctggcccag cccagaact | 600 |
| tcacactgtt catcaaaaac acagtcacct tcagcaagtt caacttctct aagtccaatg | 660 |
| ccttggagac ctgggacccc acctatttta agcactgccg ctatgaacca caattcagcc | 720 |
| cctactgtcc cgtgttccgc attggggacc tcgtggccaa ggctggaggg accttcgagg | 780 |
| acctggcgtt gctgggtggc tctgtaggca tcagagttca ctgggattgt gacctggaca | 840 |
| ccggggactc tggctgctgg cctcactact ccttccagct gcaggagaag agctacaact | 900 |
| tcaggacagc cactcactgg tgggagcaac cgggtgtgga ggcccgcacc ctgctcaagc | 960 |
| tctatggaat ccgcttcgac atcctcgtca ccgggcaggc agggaagttc gggctcatcc | 1020 |
| ccacggccgt cacactgggc accggggcag cttggctggg cgtggtcacc tttttctgtg | 1080 |
| acctgctact gctgtatgtg gatagagaag cccatttcta ctggaggaca aagtatgagg | 1140 |
| aggccaaggc cccgaaagca accgccaact ctgtgtggag ggagctggcc tttgcatccc | 1200 |
| aagcccgact ggccgagtgc ctcagacgga gctcagcacc tgcacccacg gccactgctg | 1260 |
| ctgggagtca gacacagaca ccaggatggc cctgtccaag ttctgacacc cacttgccaa | 1320 |
| cccattccgg gagcctgtag ccgtttccct gctggttgag aagagagagg ggctgggcaa | 1380 |
| ggaaggaccc ctgccctgcc gagcgaaagc aaggatgagg caacagcaat gaaagaagat | 1440 |
| caagccgaat tc | 1452 |

<210> SEQ ID NO 8
<211> LENGTH: 388
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 8

Met Ala Gly Cys Cys Ser Ala Leu Ala Ala Phe Leu Phe Glu Tyr Asp
1               5                   10                  15

Thr Pro Arg Ile Val Leu Ile Arg Ser Arg Lys Val Gly Leu Met Asn

-continued

```
                20                  25                  30
Arg Ala Val Gln Leu Leu Ile Leu Ala Tyr Val Ile Gly Trp Val Phe
            35                  40                  45
Val Trp Glu Lys Gly Tyr Gln Glu Thr Asp Ser Val Val Ser Ser Val
     50                   55                  60
Thr Thr Lys Val Lys Gly Val Ala Val Thr Asn Thr Ser Lys Leu Gly
 65                  70                  75                  80
Phe Arg Ile Trp Asp Val Ala Asp Tyr Val Ile Pro Ala Gln Glu Glu
                 85                  90                  95
Asn Ser Leu Phe Val Met Thr Asn Val Ile Leu Thr Met Asn Gln Thr
            100                 105                 110
Gln Gly Leu Cys Pro Glu Ile Pro Asp Ala Thr Thr Val Cys Lys Ser
            115                 120                 125
Asp Ala Ser Cys Thr Ala Gly Ser Ala Gly Thr His Ser Asn Gly Val
            130                 135                 140
Ser Thr Gly Arg Cys Val Ala Phe Asn Gly Ser Val Lys Thr Cys Glu
145                 150                 155                 160
Val Ala Ala Trp Cys Pro Val Glu Asp Asp Thr His Val Pro Gln Pro
                165                 170                 175
Ala Phe Leu Lys Ala Ala Glu Asn Phe Thr Leu Leu Val Lys Asn Asn
            180                 185                 190
Ile Trp Tyr Pro Lys Phe Asn Phe Ser Lys Arg Asn Ile Leu Pro Asn
            195                 200                 205
Ile Thr Thr Thr Tyr Leu Lys Ser Cys Ile Tyr Asp Ala Lys Thr Asp
            210                 215                 220
Pro Phe Cys Pro Ile Phe Arg Leu Gly Lys Ile Val Glu Asn Ala Gly
225                 230                 235                 240
His Ser Phe Gln Asp Met Ala Val Glu Gly Gly Ile Met Gly Ile Gln
                245                 250                 255
Val Asn Trp Asp Cys Asn Leu Asp Arg Ala Ala Ser Leu Cys Leu Pro
            260                 265                 270
Arg Tyr Ser Phe Arg Arg Leu Asp Thr Arg Asp Val Glu His Asn Val
            275                 280                 285
Ser Pro Gly Tyr Asn Phe Arg Phe Ala Lys Tyr Tyr Arg Asp Leu Ala
            290                 295                 300
Gly Asn Glu Gln Arg Thr Leu Ile Lys Ala Tyr Gly Ile Arg Phe Asp
305                 310                 315                 320
Ile Ile Val Phe Gly Lys Ala Gly Lys Phe Asp Ile Ile Pro Thr Met
                325                 330                 335
Ile Asn Ile Gly Ser Gly Leu Ala Leu Leu Gly Met Ala Thr Val Leu
            340                 345                 350
Cys Asp Ile Ile Val Leu Tyr Cys Met Lys Lys Arg Leu Tyr Tyr Arg
            355                 360                 365
Glu Lys Lys Tyr Lys Tyr Val Glu Asp Tyr Glu Gln Gly Leu Ala Ser
            370                 375                 380
Glu Leu Asp Gln
385

<210> SEQ ID NO 9
<211> LENGTH: 1978
<212> TYPE: DNA
<213> ORGANISM: Artificial Sequence
<220> FEATURE:
<223> OTHER INFORMATION: Description of Artificial Sequence:/note =
      synthetic construct
```

<400> SEQUENCE: 9

```
ggcacgaggg tccgcaagcc cggctgagag cgcgccatgg ggcaggcggg ctgcaagggg      60
ctctgcctgt cgctgttcga ctacaagacc gagaagtatg tcatcgccaa gaacaagaag     120
gtgggcctgc tgtaccggct gctgcaggcc tccatcctgg cgtacctggt cgtatgggtg     180
ttcctgataa agaagggtta ccaagacgtc gacacctccc tgcagagtgc tgtcatcacc     240
aaagtcaagg gcgtggcctt caccaacacc tcggatcttg ggcagcggat ctgggatgtc     300
gccgactacg tcattccagc ccagggagag aacgtctttt tgtggtcac caacctgatt      360
gtgaccccca ccagcggca gaacgtctgt gctgagaatg aaggcattcc tgatggcgcg     420
tgctccaagg acagcgactg ccacgctggg gaagcggtta cagctggaaa cggagtgaag     480
accggccgct gcctgcggag agggaacttg gccaggggca cctgtgagat ctttgcctgg    540
tgcccgttgg agacaagctc caggccgag gagccattcc tgaaggaggc cgaagacttc     600
accattttca taaagaacca catccgtttc cccaaattca acttctccaa aaacaatgtg     660
atggacgtca aggacagatc tttcctgaaa tcatgccact ttggccccaa gaaccactac     720
tgccccatct tccgactggg ctccatcgtc cgctgggccg ggagcgactt ccaggatata     780
gccctgcgag gtggcgtgat aggaattaat attgaatgga actgtgatct tgataaagct     840
gcctctgagt gccaccctca ctattctttt agccgtctgg acaataaact ttcaaagtct     900
gtctcctccg gtacaacttc cagatttgcc agatattacc gagacgcagc cggggtggag     960
ttccgcaccc tgatgaaagc ctacgggatc cgctttgacg tgatggtgaa cggcaagggt    1020
gctttcttct gcgacctggt actcatctac ctcatcaaaa agagagagtt ttaccgtgac    1080
aagaagtacg aggaagtgag gggcctagaa gacagttccc aggaggccga ggacgaggca    1140
tcggggctgg ggctatctga gcagctcaca tctgggccag ggctgctggg gatgccggag    1200
cagcaggagc tgcaggagcc acccgaggcg aagcgtggaa gcagcagtca gaaggggaac    1260
ggatctgtgt gcccacagct cctggagccc acaggagca cgtgaattgc ctctgcttac    1320
gttcaggccc tgtcctaaac ccagccgtct agcacccagt gatcccatgc ctttgggaat    1380
cccaggatgc tgcccaacgg gaaatttgta cattgggtgc tatcaatgcc acatcacagg    1440
gaccagccat cacagagcaa agtgacctcc acgtctgatg ctggggtcat caggacggac    1500
ccatcatggc tgtcttttg ccccacccc tgccgtcagt tcttcctttc tccgtggctg    1560
gcttcccgca ctagggaacg ggttgtaaat ggggaacatg acttccttcc ggagtccttg    1620
agcacctcag ctaaggaccg cagtgccctg tagagttcct agattacctc actgggaata    1680
gcattgtgcg tgtccggaaa agggctccat ttggttccag cccactcccc tctgcaagtg    1740
ccacagcttc cctcagagca tactctccag tggatccaag tactctctct cctaaagaca    1800
ccaccttcct gccagctgtt tgcccttagg ccagtacaca gaattaaagt ggggagatg    1860
gcagacgctt tctgggacct gcccaagata tgtattctct gacactctta tttggtcata    1920
aaacaataaa tggtgtcaat ttcaaaaaaa aaaaaaaaa aaaaaaaaa aaaaaaa       1978
```

<210> SEQ ID NO 10
<211> LENGTH: 422
<212> TYPE: PRT
<213> ORGANISM: Artificial Sequence
<220> FEATURE:
<223> OTHER INFORMATION: Description of Artificial Sequence:/note = synthetic construct

```
<400> SEQUENCE: 10

Met Gly Gln Ala Gly Cys Lys Gly Leu Cys Leu Ser Leu Phe Asp Tyr
 1               5                  10                  15

Lys Thr Glu Lys Tyr Val Ile Ala Lys Asn Lys Lys Val Gly Leu Leu
             20                  25                  30

Tyr Arg Leu Leu Gln Ala Ser Ile Leu Ala Tyr Leu Val Val Trp Val
         35                  40                  45

Phe Leu Ile Lys Lys Gly Tyr Gln Asp Val Asp Thr Ser Leu Gln Ser
     50                  55                  60

Ala Val Ile Thr Lys Val Lys Gly Val Ala Phe Thr Asn Thr Ser Asp
 65                  70                  75                  80

Leu Gly Gln Arg Ile Trp Asp Val Ala Asp Tyr Val Ile Pro Ala Gln
                 85                  90                  95

Gly Glu Asn Val Phe Val Val Thr Asn Leu Ile Val Thr Pro Asn
            100                 105                 110

Gln Arg Gln Asn Val Cys Ala Glu Asn Glu Gly Ile Pro Asp Gly Ala
            115                 120                 125

Cys Ser Lys Asp Ser Asp Cys His Ala Gly Glu Ala Val Thr Ala Gly
    130                 135                 140

Asn Gly Val Lys Thr Gly Arg Cys Leu Arg Arg Gly Asn Leu Ala Arg
145                 150                 155                 160

Gly Thr Cys Glu Ile Phe Ala Trp Cys Pro Leu Glu Thr Ser Ser Arg
                165                 170                 175

Pro Glu Glu Pro Phe Leu Lys Glu Ala Glu Asp Phe Thr Ile Phe Ile
            180                 185                 190

Lys Asn His Ile Arg Phe Pro Lys Phe Asn Phe Ser Lys Asn Asn Val
            195                 200                 205

Met Asp Val Lys Asp Arg Ser Phe Leu Lys Ser Cys His Phe Gly Pro
    210                 215                 220

Lys Asn His Tyr Cys Pro Ile Phe Arg Leu Gly Ser Ile Val Arg Trp
225                 230                 235                 240

Ala Gly Ser Asp Phe Gln Asp Ile Ala Leu Arg Gly Gly Val Ile Gly
                245                 250                 255

Ile Asn Ile Glu Trp Asn Cys Asp Leu Asp Lys Ala Ala Ser Glu Cys
            260                 265                 270

His Pro His Tyr Ser Phe Ser Arg Leu Asp Asn Lys Leu Ser Lys Ser
            275                 280                 285

Val Ser Ser Gly Tyr Asn Phe Arg Phe Ala Arg Tyr Tyr Arg Asp Ala
    290                 295                 300

Ala Gly Val Glu Phe Arg Thr Leu Met Lys Ala Tyr Gly Ile Arg Phe
305                 310                 315                 320

Asp Val Met Val Asn Gly Lys Gly Ala Phe Phe Cys Asp Leu Val Leu
                325                 330                 335

Ile Tyr Leu Ile Lys Lys Arg Glu Phe Tyr Arg Asp Lys Lys Tyr Glu
            340                 345                 350

Glu Val Arg Gly Leu Glu Asp Ser Ser Gln Glu Ala Glu Asp Glu Ala
            355                 360                 365

Ser Gly Leu Gly Leu Ser Glu Gln Leu Thr Ser Gly Pro Gly Leu Leu
    370                 375                 380

Gly Met Pro Glu Gln Gln Glu Leu Gln Glu Pro Pro Glu Ala Lys Arg
385                 390                 395                 400

Gly Ser Ser Ser Gln Lys Gly Asn Gly Ser Val Cys Pro Gln Leu Leu
                405                 410                 415
```

Glu Pro His Arg Ser Thr
            420

<210> SEQ ID NO 11
<211> LENGTH: 1452
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 11

| | | | | | |
|---|---|---|---|---|---|
| gaattcggct | gatcccgcgg | caggtgctag | caggagctgg | cagcatgggc | tccccagggg | 60 |
| ctacgacagg | ctgggggctt | ctggattata | agacggagaa | gtatgtgatg | accaggaact | 120 |
| ggcgggtggg | cgccctgcag | aggctgctgc | agtttgggat | cgtggtctat | gtggtagggt | 180 |
| gggctctcct | cgccaaaaaa | ggctaccagg | agcgggacct | ggaacccag | ttttccatca | 240 |
| tcaccaaact | caaaggggtt | tccgtcactc | agatcaagga | gcttggaaac | cggctgtggg | 300 |
| atgtggccga | cttcgtgaag | ccacctcagg | agagaacgg | gttcttcttg | gtgaccaact | 360 |
| tccttgtgac | gccagcccaa | gttcagggca | gatgcccaga | gcacccgtcc | gtcccactgg | 420 |
| ctaactgctg | ggtcgacgaa | gactgccccg | aaggggaggg | aggcacacac | agccacggtg | 480 |
| taaaaacagg | ccagtgtgtg | gtgttcaatg | gacccacag | gacctgtgag | atctggagtt | 540 |
| ggtgcccagt | ggagagtggc | gttgtgccct | cgaggcccct | gctggcccag | gcccagaact | 600 |
| tcacactgtt | catcaaaaac | acagtcacct | tcagcaagtt | caacttctct | aagtccaatg | 660 |
| ccttggagac | ctgggacccc | acctatttta | agcactgccg | ctatgaacca | caattcagcc | 720 |
| cctactgtcc | cgtgttccgc | attggggacc | tcgtggccaa | ggctggaggg | accttcgagg | 780 |
| acctggcgtt | gctgggtggc | tctgtaggca | tcagagttca | ctgggattgt | gacctggaca | 840 |
| ccggggactc | tggctgctgg | cctcactact | ccttccagct | gcaggagaag | agctacaact | 900 |
| tcaggacagc | cactcactgg | tgggagcaac | cgggtgtgga | ggcccgcacc | ctgctcaagc | 960 |
| tctatggaat | ccgcttcgac | atcctcgtca | ccgggcaggc | agggaagttc | gggctcatcc | 1020 |
| ccacggccgt | cacactgggc | accggggcag | cttggctggg | cgtggtcacc | ttttctctgtg | 1080 |
| acctgctact | gctgtatgtg | gatagagaag | cccatttcta | ctggaggaca | agtatgagg | 1140 |
| aggccaaggc | cccgaaagca | accgccaact | ctgtgtggag | ggagctggcc | tttgcatccc | 1200 |
| aagcccgact | ggccgagtgc | ctcagacgga | gctcagcacc | tgcacccacg | gccactgctg | 1260 |
| ctgggagtca | gacacagaca | ccaggatggc | cctgtccaag | ttctgacacc | cacttgccaa | 1320 |
| cccattccgg | gagcctgtag | ccgtttccct | gctggttgag | aagagagagg | ggctgggcaa | 1380 |
| ggaaggaccc | ctgccctgcc | gagcgaaagc | aaggatgagg | caacagcaat | gaaagaagat | 1440 |
| caagccgaat | tc | | | | | 1452 |

<210> SEQ ID NO 12
<211> LENGTH: 431
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 12

Met Gly Ser Pro Gly Ala Thr Thr Gly Trp Gly Leu Leu Asp Tyr Lys
1               5                   10                  15

-continued

```
Thr Glu Lys Tyr Val Met Thr Arg Asn Trp Arg Val Gly Ala Leu Gln
        20                  25                  30
Arg Leu Leu Gln Phe Gly Ile Val Tyr Val Gly Trp Ala Leu
        35                  40                  45
Leu Ala Lys Lys Gly Tyr Gln Glu Arg Asp Leu Glu Pro Gln Phe Ser
 50                  55                  60
Ile Ile Thr Lys Leu Lys Gly Val Ser Val Thr Gln Ile Lys Glu Leu
 65                  70                  75                  80
Gly Asn Arg Leu Trp Asp Val Ala Asp Phe Val Lys Pro Pro Gln Gly
                85                  90                  95
Glu Asn Val Phe Phe Leu Val Thr Asn Phe Leu Val Thr Pro Ala Gln
                100                 105                 110
Val Gln Gly Arg Cys Pro Glu His Pro Ser Val Pro Leu Ala Asn Cys
                115                 120                 125
Trp Val Asp Glu Asp Cys Pro Glu Gly Glu Gly Thr His Ser His
130                 135                 140
Gly Val Lys Thr Gly Gln Cys Val Val Phe Asn Gly Thr His Arg Thr
145                 150                 155                 160
Cys Glu Ile Trp Ser Trp Cys Pro Val Glu Ser Gly Val Val Pro Ser
                165                 170                 175
Arg Pro Leu Leu Ala Gln Ala Gln Asn Phe Thr Leu Phe Ile Lys Asn
                180                 185                 190
Thr Val Thr Phe Ser Lys Phe Asn Phe Ser Lys Ser Asn Ala Leu Glu
                195                 200                 205
Thr Trp Asp Pro Thr Tyr Phe Lys His Cys Arg Tyr Glu Pro Gln Phe
210                 215                 220
Ser Pro Tyr Cys Pro Val Phe Arg Ile Gly Asp Leu Val Ala Lys Ala
225                 230                 235                 240
Gly Gly Thr Phe Glu Asp Leu Ala Leu Leu Gly Gly Ser Val Gly Ile
                245                 250                 255
Arg Val His Trp Asp Cys Asp Leu Asp Thr Gly Asp Ser Gly Cys Trp
                260                 265                 270
Pro His Tyr Ser Phe Gln Leu Gln Glu Lys Ser Tyr Asn Phe Arg Thr
                275                 280                 285
Ala Thr His Trp Trp Glu Gln Pro Gly Val Glu Ala Arg Thr Leu Leu
                290                 295                 300
Lys Leu Tyr Gly Ile Arg Phe Asp Ile Leu Val Thr Gly Gln Ala Gly
305                 310                 315                 320
Lys Phe Gly Leu Ile Pro Thr Ala Val Thr Leu Gly Thr Gly Ala Ala
                325                 330                 335
Trp Leu Gly Val Val Thr Phe Phe Cys Asp Leu Leu Leu Tyr Val
                340                 345                 350
Asp Arg Glu Ala His Phe Tyr Trp Arg Thr Lys Tyr Glu Glu Ala Lys
                355                 360                 365
Ala Pro Lys Ala Thr Ala Asn Ser Val Trp Arg Glu Leu Ala Phe Ala
                370                 375                 380
Ser Gln Ala Arg Leu Ala Glu Cys Leu Arg Arg Ser Ser Ala Pro Ala
385                 390                 395                 400
Pro Thr Ala Thr Ala Ala Gly Ser Gln Thr Gln Thr Pro Gly Trp Pro
                405                 410                 415
Cys Pro Ser Ser Asp Thr His Leu Pro Thr His Ser Gly Ser Leu
                420                 425                 430
```

<210> SEQ ID NO 13
<211> LENGTH: 1853
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 13

```
aaaacgcagg gagggaggct gtcaccatgc cggcctgctg cagctgcagt gatgttttcc      60
agtatgagac gaacaaagtc actcggatcc agagcatgaa ttatggcacc attaagtggt     120
tcttccacgt gatcatcttt tcctacgttt gctttgctct ggtgagtgac aagctgtacc     180
agcggaaaga gcctgtcatc agttctgtgc acaccaaggt gaaggggata gcagaggtga     240
aagaggagat cgtggagaat ggagtgaaga agttggtgca cagtgtcttt gacaccgcag     300
actacacctt cccttttgcag gggaactctt tcttcgtgat gacaaacttt ctcaaaacag     360
aaggccaaga gcagcggttg tgtcccgagt atcccacccg caggacgctc tgttcctctg     420
accgaggttg taaaaaggga tggatggacc cgcagagcaa aggaattcag accggaaggt     480
gtgtagtgca tgaagggaac cagaagacct gtgaagtctc tgcctggtgc ccatcgagg      540
cagtggaaga ggccccccgg cctgctctct tgaacagtgc cgaaaacttc actgtgctca     600
tcaagaacaa tatcgacttc cccggccaca actacaccac gagaaacatc ctgccaggtt     660
taaacatcac ttgtaccttc cacaagactc agaatccaca gtgtcccatt ttccgactag     720
gagacatctt ccgagaaaca ggcgataatt tttcagatgt ggcaattcag ggcggaataa     780
tgggcattga gatctactgg gactgcaacc tagaccgttg gttccatcac tgccatccca     840
aatacagttt ccgtcgcctt gacgacaaga ccaccaacgt gtccttgtac cctggctaca     900
acttcagata cgccaagtac tacaaggaaa acaatgttga gaacggact ctgataaaag       960
tcttcgggat ccgttttgac atcctggttt ttggcaccgg aggaaaattt gacattatcc    1020
agctggttgt gtacatcggc tcaaccctct cctacttcgg tctggccgct gtgttcatcg    1080
acttcctcat cgacacttac tccagtaact gctgtcgctc ccatatttat ccctggtgca    1140
agtgctgtca gccctgtgtg gtcaacgaat actactacag gaagaagtgc gagtccattg    1200
tggagccaaa gccgacatta agtatgtgt cctttgtgga tgaatcccac attaggatgg     1260
tgaaccagca gctactaggg agaagtctgc aagatgtcaa gggccaagaa gtcccaagac    1320
ctgcgatgga cttcacagat ttgtccaggc tgccctggc cctccatgac acaccccga     1380
ttcctggaca accagaggag atacagctgc ttagaaagga ggcgactcct agatccaggg    1440
atagccccgt ctggtgccag tgtggaagct gcctcccatc tcaactccct gagagccaca    1500
ggtgcctgga ggagctgtgc tgccggaaaa agccgggggc ctgcatcacc acctcagagc    1560
tgttcaggaa gctggtcctg tccagacacg tcctgcagtt cctcctgctc taccaggagc    1620
ccttgctggc gctggatgtg gattccacca acagccggct gcggcactgt gcctacaggt    1680
gctacgccac ctggcgcttc ggctcccagg acatggctga ctttgccatc ctgcccagct    1740
gctgccgctg gaggatccgg aaagagttc cgaagagtga agggcagtac agtggcttca    1800
agagtcctta ctgaagccag gcaccgtggc tcacgtctgt aatcccacct ttt           1853
```

<210> SEQ ID NO 14
<211> LENGTH: 595
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 14

```
Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys His Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
            340                 345                 350

Phe Leu Ile Asp Thr Tyr Ser Ser Asn Cys Cys Arg Ser His Ile Tyr
        355                 360                 365

Pro Trp Cys Lys Cys Cys Gln Pro Cys Val Val Asn Glu Tyr Tyr Tyr
    370                 375                 380

Arg Lys Lys Cys Glu Ser Ile Val Glu Pro Lys Pro Thr Leu Lys Tyr
385                 390                 395                 400
```

-continued

```
Val Ser Phe Val Asp Glu Ser His Ile Arg Met Val Asn Gln Gln Leu
                405                 410                 415
Leu Gly Arg Ser Leu Gln Asp Val Lys Gly Gln Glu Val Pro Arg Pro
            420                 425                 430
Ala Met Asp Phe Thr Asp Leu Ser Arg Leu Pro Leu Ala Leu His Asp
        435                 440                 445
Thr Pro Pro Ile Pro Gly Gln Pro Glu Glu Ile Gln Leu Leu Arg Lys
    450                 455                 460
Glu Ala Thr Pro Arg Ser Arg Asp Ser Pro Val Trp Cys Gln Cys Gly
465                 470                 475                 480
Ser Cys Leu Pro Ser Gln Leu Pro Glu Ser His Arg Cys Leu Glu Glu
                485                 490                 495
Leu Cys Cys Arg Lys Lys Pro Gly Ala Cys Ile Thr Thr Ser Glu Leu
            500                 505                 510
Phe Arg Lys Leu Val Leu Ser Arg His Val Leu Gln Phe Leu Leu Leu
        515                 520                 525
Tyr Gln Glu Pro Leu Leu Ala Leu Asp Val Asp Ser Thr Asn Ser Arg
    530                 535                 540
Leu Arg His Cys Ala Tyr Arg Cys Tyr Ala Thr Trp Arg Phe Gly Ser
545                 550                 555                 560
Gln Asp Met Ala Asp Phe Ala Ile Leu Pro Ser Cys Cys Arg Trp Arg
                565                 570                 575
Ile Arg Lys Glu Phe Pro Lys Ser Glu Gly Gln Tyr Ser Gly Phe Lys
            580                 585                 590
Ser Pro Tyr
        595
```

<210> SEQ ID NO 15
<211> LENGTH: 1312
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 15

```
ggatccagtt cgcctgctcc cttccgctcg ctggcttttc cgatgcttgc tgcgcccctg      60
gccgccgctg ccctctcgcc gcctcctacc cctcggagcc gccgcctaag tcgaggagga     120
gagaatgacc gaggtgctgt ggccggctgt ccccaacggg acggacgctg ccttcctggc     180
cggtccgggt tcgtcctggg ggaacagcac ggtcgcctcc actgccgccg tctcctcgtc     240
gttcaaatgc gccttgacca agacgggctt ccagttttac tacctgccgg ctgtctacat     300
cttggtattc atcatcggct tcctgggcaa cagcgtggcc atctggatgt tcgtcttcca     360
catgaagccc tggagcggca tctccgtgta catgttcaat ttggctctgg ccgacttctt     420
gtacgtgctg actctgccag ccctgatctt ctactacttc aataaaacag actggatctt     480
cgggatgcc atgtgtaaac tgcagaggtt catctttcat gtgaacctct atggcagcat     540
cttgtttctg acatgcatca gtgcccaccg gtacagcggt gtggtgtacc ccctcaagtc     600
cctgggccgg ctcaaaaaga gaatgcgat ctgtatcagc gtgctggtgt ggctcattgt     660
ggtggtggcg atctccccca tcctcttcta ctcaggtacc ggggtccgca aaacaaaaac     720
catcacctgt tacgacacca cctcagacga gtacctgcga agttatttca tctacagcat     780
gtgcacgacc gtggccatgt tctgtgtccc cttggtgctg attctgggct gttacggatt     840
aattgtgaga gctttgattt acaaagatct ggacaactct cctctgagga gaaaatcgat     900
```

-continued

```
ttacctggta atcattgtac tgactgtttt tgctgtgtct tacatcccctt tccatgtgat    960 gaaaacgatg aacttgaggg cccggcttga ttttcagacc ccagcaatgt gtgctttcaa   1020
tgacagggtt tatgccacgt atcaggtgac aagaggtcta gcaagtctca acagttgtgt   1080
ggaccccatt ctctatttct tggcgggaga tactttcaga aggagactct cccgagccac   1140
aaggaaagct tctagaagaa gtgaggcaaa tttgcaatcc aagagtgaag acatgaccct   1200
caatatttta cctgagttca agcagaatgg agatacaagc ctgtgaaggc acaagaatct   1260
ccaaacacct ctctgttgta atatggtagg atgcttaaca gaatcaagta ct           1312
```

<210> SEQ ID NO 16
<211> LENGTH: 373
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 16

```
Met Thr Glu Val Leu Trp Pro Ala Val Pro Asn Gly Thr Asp Ala Ala
 1               5                  10                  15

Phe Leu Ala Gly Pro Gly Ser Ser Trp Gly Asn Ser Thr Val Ala Ser
            20                  25                  30

Thr Ala Ala Val Ser Ser Ser Phe Lys Cys Ala Leu Thr Lys Thr Gly
        35                  40                  45

Phe Gln Phe Tyr Tyr Leu Pro Ala Val Tyr Ile Leu Val Phe Ile Ile
    50                  55                  60

Gly Phe Leu Gly Asn Ser Val Ala Ile Trp Met Phe Val Phe His Met
65                  70                  75                  80

Lys Pro Trp Ser Gly Ile Ser Val Tyr Met Phe Asn Leu Ala Leu Ala
                85                  90                  95

Asp Phe Leu Tyr Val Leu Thr Leu Pro Ala Leu Ile Phe Tyr Tyr Phe
            100                 105                 110

Asn Lys Thr Asp Trp Ile Phe Gly Asp Ala Met Cys Lys Leu Gln Arg
        115                 120                 125

Phe Ile Phe His Val Asn Leu Tyr Gly Ser Ile Leu Phe Leu Thr Cys
    130                 135                 140

Ile Ser Ala His Arg Tyr Ser Gly Val Val Tyr Pro Leu Lys Ser Leu
145                 150                 155                 160

Gly Arg Leu Lys Lys Lys Asn Ala Ile Cys Ile Ser Val Leu Val Trp
                165                 170                 175

Leu Ile Val Val Val Ala Ile Ser Pro Ile Leu Phe Tyr Ser Gly Thr
            180                 185                 190

Gly Val Arg Lys Asn Lys Thr Ile Thr Cys Tyr Asp Thr Thr Ser Asp
        195                 200                 205

Glu Tyr Leu Arg Ser Tyr Phe Ile Tyr Ser Met Cys Thr Thr Val Ala
    210                 215                 220

Met Phe Cys Val Pro Leu Val Leu Ile Leu Gly Cys Tyr Gly Leu Ile
225                 230                 235                 240

Val Arg Ala Leu Ile Tyr Lys Asp Leu Asp Asn Ser Pro Leu Arg Arg
                245                 250                 255

Lys Ser Ile Tyr Leu Val Ile Ile Val Leu Thr Val Phe Ala Val Ser
            260                 265                 270

Tyr Ile Pro Phe His Val Met Lys Thr Met Asn Leu Arg Ala Arg Leu
        275                 280                 285
```

```
Asp Phe Gln Thr Pro Ala Met Cys Ala Phe Asn Asp Arg Val Tyr Ala
    290                 295                 300

Thr Tyr Gln Val Thr Arg Gly Leu Ala Ser Leu Asn Ser Cys Val Asp
305                 310                 315                 320

Pro Ile Leu Tyr Phe Leu Ala Gly Asp Thr Phe Arg Arg Leu Ser
                325                 330                 335

Arg Ala Thr Arg Lys Ala Ser Arg Arg Ser Glu Ala Asn Leu Gln Ser
            340                 345                 350

Lys Ser Glu Asp Met Thr Leu Asn Ile Leu Pro Glu Phe Lys Gln Asn
        355                 360                 365

Gly Asp Thr Ser Leu
        370

<210> SEQ ID NO 17
<211> LENGTH: 2025
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 17
```

| | | | | | |
|---|---|---|---|---|---|
| cggcacgagg | caccccgaga | ggagaagcgc | agcgcagtgg | cgagaggagc | cccttgtggc | 60 |
| agcagcacta | cctgcccaga | aaaatgctgg | aggctgggcg | tggccccagg | cctggggacc | 120 |
| tgttttttcct | gtttcccgca | gagttccctg | cagcccggtc | caggtccagg | cgtgtgcatt | 180 |
| catgagtgag | gaacccgtgc | aggcgctgag | catcctgacc | tggagagcag | ggctggtca | 240 |
| gggcgatggc | agcagacctg | gcccctggaa | tgacaccat | caatggcacc | tgggatgggg | 300 |
| atgagctggg | ctacaggtgc | cgcttcaacg | aggacttcaa | gtacgtgctg | ctgcctgtgt | 360 |
| cctacggcgt | ggtgtgcgtg | cttgggctgt | gtctgaacgc | cgtggcgctc | tacatcttct | 420 |
| tgtgccgcct | caagacctgg | aatgcgtcca | ccacatatat | gttccacctg | gctgtgtctg | 480 |
| atgcactgta | tgcggcctcc | ctgccgctgc | tggtctatta | ctacgcccgc | ggcgaccact | 540 |
| ggccttcag | cacggtgctc | tgcaagctgg | tgcgcttcct | cttctacacc | aacctttact | 600 |
| gcagcatcct | cttcctcacc | tgcatcagcg | tgcaccggtg | tctgggcgtc | ttacgacctc | 660 |
| tgcgctccct | gcgctggggc | cgggcccgct | acgctcgccg | ggtggccggg | gccgtgtggg | 720 |
| tgttggtgct | ggcctgccag | gccccgtgc | tctactttgt | caccaccagc | gcgcgcgggg | 780 |
| gccgcgtaac | ctgccacgac | acctcggcac | ccgagctctt | cagccgcttc | gtggcctaca | 840 |
| gctcagtcat | gctgggcctg | ctcttcgcgg | tgccctttgc | cgtcatcctt | gtctgttacg | 900 |
| tgctcatggc | tcggcgactg | ctaaagccag | cctacggac | ctcgggcggc | ctccctaggg | 960 |
| ccaagcgcaa | gtccgtgcgc | accatcgccg | tggtgctggc | tgtcttcgcc | ctctgcttcc | 1020 |
| tgccattcca | cgtcacccgc | accctctact | actccttccg | ctcgctggac | tcagctgcc | 1080 |
| acaccctcaa | cgccatcaac | atggcctaca | aggttacccg | gccgctggcc | agtgctaaca | 1140 |
| gttgcctga | cccgtgctc | tacttcctgg | ctgggcagag | gctcgtacgc | tttgcccgag | 1200 |
| atgccaagcc | acccactggc | cccagccctg | ccaccccggc | tcgccgcagg | ctgggcctgc | 1260 |
| gcagatccga | cagaactgac | atgcagagga | taggagatgt | gttgggcagc | agtgaggact | 1320 |
| tcaggcggac | agagtccacg | ccggctggta | gcagaacac | taaggacatt | cggctgtagg | 1380 |
| agcagaaacac | ttcagcctgt | gcaggtttat | attgggaagc | tgtagaggac | caggacttgt | 1440 |
| gcagacgcca | cagtctcccc | agatatggac | catcagtgac | tcatgctgga | tgaccccatg | 1500 |

-continued

```
ctccgtcatt tgacaggggc tcaggatatt cactctgtgg tccagagtca actgttccca      1560 taaccccctag tcatcgtttg tgtgtataag ttgggggaat taagtttcaa gaaaggcaag     1620
agctcaaggt caatgacacc cctggcctga ctcccatgca agtagctggc tgtactgcca      1680
aggtacctag gttggagtcc agcctaatca agtcaaatgg agaaacaggc ccagagagga      1740
aggtggctta ccaagatcac ataccagagt ctggagctga gctacctggg gtgggggcca     1800
agtcacaggt tggccagaaa accctggtaa gtaatgaggg ctgagtttgc acagtggtct      1860
ggaatggact gggtgccacg gtggacttag ctctgaggag tacccccagc caagagatg       1920 aacatctggg gactaatatc atagacccat ctggaggctc ccatgggcta ggagcagtgt      1980
gaggctgtaa cttatactaa aggttgtgtt gcctgctaaa aaaaa                      2025
```

<210> SEQ ID NO 18
<211> LENGTH: 377
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 18

```
Met Ala Ala Asp Leu Gly Pro Trp Asn Asp Thr Ile Asn Gly Thr Trp
 1               5                  10                  15

Asp Gly Asp Glu Leu Gly Tyr Arg Cys Arg Phe Asn Glu Asp Phe Lys
            20                  25                  30

Tyr Val Leu Leu Pro Val Ser Tyr Gly Val Val Cys Val Leu Gly Leu
        35                  40                  45

Cys Leu Asn Ala Val Ala Leu Tyr Ile Phe Leu Cys Arg Leu Lys Thr
    50                  55                  60

Trp Asn Ala Ser Thr Thr Tyr Met Phe His Leu Ala Val Ser Asp Ala
65                  70                  75                  80

Leu Tyr Ala Ala Ser Leu Pro Leu Leu Val Tyr Tyr Ala Arg Gly
            85                  90                  95

Asp His Trp Pro Phe Ser Thr Val Leu Cys Lys Leu Val Arg Phe Leu
        100                 105                 110

Phe Tyr Thr Asn Leu Tyr Cys Ser Ile Leu Phe Leu Thr Cys Ile Ser
        115                 120                 125

Val His Arg Cys Leu Gly Val Leu Arg Pro Leu Arg Ser Leu Arg Trp
    130                 135                 140

Gly Arg Ala Arg Tyr Ala Arg Arg Val Ala Gly Ala Val Trp Val Leu
145                 150                 155                 160

Val Leu Ala Cys Gln Ala Pro Val Leu Tyr Phe Val Thr Thr Ser Ala
            165                 170                 175

Arg Gly Gly Arg Val Thr Cys His Asp Thr Ser Ala Pro Glu Leu Phe
        180                 185                 190

Ser Arg Phe Val Ala Tyr Ser Ser Val Met Leu Gly Leu Leu Phe Ala
        195                 200                 205

Val Pro Phe Ala Val Ile Leu Val Cys Tyr Val Leu Met Ala Arg Arg
    210                 215                 220

Leu Leu Lys Pro Ala Tyr Gly Thr Ser Gly Gly Leu Pro Arg Ala Lys
225                 230                 235                 240

Arg Lys Ser Val Arg Thr Ile Ala Val Val Leu Ala Val Phe Ala Leu
            245                 250                 255

Cys Phe Leu Pro Phe His Val Thr Arg Thr Leu Tyr Tyr Ser Phe Arg
```

-continued

```
                  260                 265                 270
Ser Leu Asp Leu Ser Cys His Thr Leu Asn Ala Ile Asn Met Ala Tyr
            275                 280                 285
Lys Val Thr Arg Pro Leu Ala Ser Ala Asn Ser Cys Leu Asp Pro Val
        290                 295                 300
Leu Tyr Phe Leu Ala Gly Gln Arg Leu Val Arg Phe Ala Arg Asp Ala
305                 310                 315                 320
Lys Pro Pro Thr Gly Pro Ser Pro Ala Thr Pro Ala Arg Arg Arg Leu
                325                 330                 335
Gly Leu Arg Arg Ser Asp Arg Thr Asp Met Gln Arg Ile Gly Asp Val
            340                 345                 350
Leu Gly Ser Ser Glu Asp Phe Arg Arg Thr Glu Ser Thr Pro Ala Gly
        355                 360                 365
Ser Glu Asn Thr Lys Asp Ile Arg Leu
    370                 375

<210> SEQ ID NO 19
<211> LENGTH: 1163
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 19
ggcgcttcac ccagtaaaga gggaccatga gcatggccaa cttcacgggg gggaggaact      60
cgtgcacctt ccatgaggaa ttcaagcagg tcctgctgcc cctggtctac tcagtggtgt     120
tcctactggg gctgccactc aatgccgttg tcattgggca gatctggctg ccccgcaagg     180
cgttgacccg caccaccatc tacatgctga acctggccat ggccgacctg ctttatgtct     240
gctcccctcc tctcctcatc tacaaactac cccagaagga ttactggccc tttggggact     300
tcacctgcaa attcgtccgc ttccagttct acaccaacct gcacggcagc atcctcttcc     360
tcacctgcat cagcgtccag cgctacatgg ggatctgcca ccccttggcc tcgtggcaca     420
aaaagaaggg aaagaagctg acgtggctgg tgtgtgctgc cgtgtggttc atcgtcatcg     480
cccagtgcct gccccacctt tgtcttcgcct ccaccggcac gcagaggaat cgcactgtct     540
gctatgacct gagccccccg gaccgctcca catcctactt ccccctatgg catcacgttga     600 ccatcactgg cttcctgctg cccttcgcag ccatcctggc ctgctactgc agcatggccc     660
gcatcctgtg ccagaaagac gagctgattg gcttggcggt gcacaagaag aaggacaagg     720
ccgtgcgcat gatcatcatc gttgtcatcg tcttctccat cagcttcttc cccttccacc     780
tcaccaagac catctacctg atcgtccgct cctcagccag cttgccctgc ctaccctgc      840 aggcttttgc cattgcctac aagtgcacgc ggccctttgc cagcatgaac agcgtcctcg     900
accccatcct cttctacttc acccagcgca agtttcgtga agcacccgc tatctcctgg      960 acaagatgag ctccaagtgg cggcaagacc actgcatcag ctacggctcc taggtggacg    1020
aggccacctc ggtgtcaccg gggctgggca tggagcaatt tgggttgaag ctgcatggtg    1080
cggagatggg gatgagccca gagtgctgcg ggtgccccat ctctggaggt gttggagatt    1140
agattggatg gggctctggg ccc                                            1163

<210> SEQ ID NO 20
<211> LENGTH: 328
<212> TYPE: PRT
<213> ORGANISM: Artificial Sequence
```

```
<220> FEATURE:
<223> OTHER INFORMATION: Description of Artificial Sequence:/note =
      synthetic construct

<400> SEQUENCE: 20

Met Ser Met Ala Asn Phe Thr Gly Gly Arg Asn Ser Cys Thr Phe His
1               5                   10                  15

Glu Glu Phe Lys Gln Val Leu Leu Pro Leu Val Tyr Ser Val Val Phe
                20                  25                  30

Leu Leu Gly Leu Pro Leu Asn Ala Val Val Ile Gly Gln Ile Trp Leu
            35                  40                  45

Ala Arg Lys Ala Leu Thr Arg Thr Thr Ile Tyr Met Leu Asn Leu Ala
    50                  55                  60

Met Ala Asp Leu Leu Tyr Val Cys Ser Leu Pro Leu Leu Ile Tyr Asn
65                  70                  75                  80

Tyr Thr Gln Lys Asp Tyr Trp Pro Phe Gly Asp Phe Thr Cys Lys Phe
                85                  90                  95

Val Arg Phe Gln Phe Tyr Thr Asn Leu His Gly Ser Ile Leu Phe Leu
                100                 105                 110

Thr Cys Ile Ser Val Gln Arg Tyr Met Gly Ile Cys His Pro Leu Ala
            115                 120                 125

Ser Trp His Lys Lys Gly Lys Lys Leu Thr Trp Leu Val Cys Ala
130                 135                 140

Ala Val Trp Phe Ile Val Ile Ala Gln Cys Leu Pro Thr Phe Val Phe
145                 150                 155                 160

Ala Ser Thr Gly Thr Gln Arg Asn Arg Thr Val Cys Tyr Asp Leu Ser
                165                 170                 175

Pro Pro Asp Arg Ser Thr Ser Tyr Phe Pro Tyr Gly Ile Thr Leu Thr
            180                 185                 190

Ile Thr Gly Phe Leu Leu Pro Phe Ala Ala Ile Leu Ala Cys Tyr Cys
        195                 200                 205

Ser Met Ala Arg Ile Leu Cys Gln Lys Asp Glu Leu Ile Gly Leu Ala
210                 215                 220

Val His Lys Lys Lys Asp Lys Ala Val Arg Met Ile Ile Ile Val Val
225                 230                 235                 240

Ile Val Phe Ser Ile Ser Phe Phe Pro Phe His Leu Thr Lys Thr Ile
                245                 250                 255

Tyr Leu Ile Val Arg Ser Ser Ala Ser Leu Pro Cys Pro Thr Leu Gln
            260                 265                 270

Ala Phe Ala Ile Ala Tyr Lys Cys Thr Arg Pro Phe Ala Ser Met Asn
        275                 280                 285

Ser Val Leu Asp Pro Ile Leu Phe Tyr Phe Thr Gln Arg Lys Phe Arg
    290                 295                 300

Glu Ser Thr Arg Tyr Leu Leu Asp Lys Met Ser Ser Lys Trp Arg Gln
305                 310                 315                 320

Asp His Cys Ile Ser Tyr Gly Ser
                325

<210> SEQ ID NO 21
<211> LENGTH: 1429
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 21
```

```
aagggagctt gggtaggggc caggctagcc tgagtgcacc cagatgcgct tctgtcagct    60
ctccctagtg cttcaaccac tgctctccct gctctacttt ttttgctcca gctcagggat   120
gggggtgggc agggaaatcc tgccaccctc acttctcccc ttcccatctc caggggggcc   180
atggccagta cagagtcctc cctgttgaga tccctaggcc tcagcccagg tcctggcagc   240
agtgaggtgg agctggactg ttggtttgat gaggatttca agttcatcct gctgcctgtg   300
agctatgcag ttgtctttgt gctgggcttg ggccttaacg ccccaaccct atggctcttc   360
atcttccgcc tccgaccctg ggatgcaacg gccacctaca tgttccacct ggcattgtca   420
gacaccttgt atgtgctgtc gctgcccacc ctcatctact attatgcagc ccacaaccac   480
tggcccttg gcactgagat ctgcaagttc gtccgctttc ttttctattg gaacctctac   540
tgcagtgtcc ttttcctcac ctgcatcagc gtgcaccgct acctgggcat ctgccaccca   600
cttcgggcac tacgctgggg ccgccctcgc ctcgcaggcc ttctctgcct ggcagtttgg   660
ttggtcgtag ccggctgcct cgtgcccaac ctgttctttg tcacaaccag caacaaaggg   720
accaccgtcc tgtgccatga caccactcgg cctgaagagt ttgaccacta tgtgcacttc   780
agctcggcgg tcatggggct gctctttggc gtgccctgcc tggtcactct tgtttgctat   840
ggactcatgg ctcgtcgcct gtatcagccc ttgccaggct ctgcacagtc gtcttctcgc   900
ctccgctctc tccgcaccat agctgtggtg ctgactgtct ttgctgtctg cttcgtgcct   960
ttccacatca cccgcaccat ttactacctg ccaggctgt tggaagctga ctgccgagta  1020
ctgaacattg tcaacgtggt ctataaagtg actcggcccc tggccagtgc caacagctgc  1080
ctggatcctg tgctctactt gctcactggg gacaaatatc gacgtcagct ccgtcagctc  1140
tgtggtggtg gcaagcccca gccccgcacg gctgcctctt ccctggcact agtgtccctg  1200
cctgaggata gcagctgcag gtgggcggcc accccccagg acagtagctg ctctactcct  1260
agggcagata gattgtaaca cgggaagccg ggaagtgaga gaaaagggga tgagtgcagg  1320
gcagaggtga gggaacccaa tagtgatacc tggtaaggtg cttcttcctc ttttccaggc  1380
tctggagaga agccctcacc ctgagggttg ccagggaggc agggatatc                1429
```

<210> SEQ ID NO 22
<211> LENGTH: 365
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 22

```
Met Ala Ser Thr Glu Ser Ser Leu Leu Arg Ser Leu Gly Leu Ser Pro
 1               5                  10                  15

Gly Pro Gly Ser Ser Glu Val Glu Leu Asp Cys Trp Phe Asp Glu Asp
            20                  25                  30

Phe Lys Phe Ile Leu Leu Pro Val Ser Tyr Ala Val Phe Val Leu
        35                  40                  45

Gly Leu Gly Leu Asn Ala Pro Thr Leu Trp Leu Phe Ile Phe Arg Leu
    50                  55                  60

Arg Pro Trp Asp Ala Thr Ala Thr Tyr Met Phe His Leu Ala Leu Ser
65                  70                  75                  80

Asp Thr Leu Tyr Val Leu Ser Leu Pro Thr Leu Ile Tyr Tyr Tyr Ala
                85                  90                  95

Ala His Asn His Trp Pro Phe Gly Thr Glu Ile Cys Lys Phe Val Arg
```

```
                100                 105                 110
Phe Leu Phe Tyr Trp Asn Leu Tyr Cys Ser Val Leu Phe Leu Thr Cys
        115                 120                 125
Ile Ser Val His Arg Tyr Leu Gly Ile Cys His Pro Leu Arg Ala Leu
    130                 135                 140
Arg Trp Gly Arg Pro Arg Leu Ala Gly Leu Leu Cys Leu Ala Val Trp
145                 150                 155                 160
Leu Val Val Ala Gly Cys Leu Val Pro Asn Leu Phe Phe Val Thr Thr
                165                 170                 175
Ser Asn Lys Gly Thr Thr Val Leu Cys His Asp Thr Thr Arg Pro Glu
            180                 185                 190
Glu Phe Asp His Tyr Val His Phe Ser Ser Ala Val Met Gly Leu Leu
        195                 200                 205
Phe Gly Val Pro Cys Leu Val Thr Leu Val Cys Tyr Gly Leu Met Ala
    210                 215                 220
Arg Arg Leu Tyr Gln Pro Leu Pro Gly Ser Ala Gln Ser Ser Ser Arg
225                 230                 235                 240
Leu Arg Ser Leu Arg Thr Ile Ala Val Val Leu Thr Val Phe Ala Val
                245                 250                 255
Cys Phe Val Pro Phe His Ile Thr Arg Thr Ile Tyr Tyr Leu Ala Arg
            260                 265                 270
Leu Leu Glu Ala Asp Cys Arg Val Leu Asn Ile Val Asn Val Val Tyr
        275                 280                 285
Lys Val Thr Arg Pro Leu Ala Ser Ala Asn Ser Cys Leu Asp Pro Val
    290                 295                 300
Leu Tyr Leu Leu Thr Gly Asp Lys Tyr Arg Arg Gln Leu Arg Gln Leu
305                 310                 315                 320
Cys Gly Gly Gly Lys Pro Gln Pro Arg Thr Ala Ala Ser Ser Leu Ala
                325                 330                 335
Leu Val Ser Leu Pro Glu Asp Ser Ser Cys Arg Trp Ala Ala Thr Pro
            340                 345                 350
Gln Asp Ser Ser Cys Ser Thr Pro Arg Ala Asp Arg Leu
        355                 360                 365

<210> SEQ ID NO 23
<211> LENGTH: 1571
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 23
ctcagtttcc tcatctgctg cctctccaga cttctgccag aacattgcac gcgacagttt      60
caggcacaga actgactggc agcaggggct gctccacgag tgggaatttg ctccagcact     120
tcacggactg caagcgaggc acttgctaac tcttggataa caagacctct gccagaagaa     180
ccatggcttt ggaaggcgga gttcaggctg aggagatggg tgcggtcctc agtgagcccc     240
tgcctccctg aacataggaa acccacctgg gcagccatgg aatgggacaa tggcacaggc     300
caggctctgg gcttgccacc caccacctgt gtctaccgcg agaacttcaa gcaactgctg     360
ctgccacctg tgtattcggc ggtgctggcg gctggcctgc cgctgaacat ctgtgtcatt     420
acccagatct gcacgtcccg ccgggccctg acccgcacgg ccgtgtacac cctaaaacctt     480 gctctggctg acctgctata tgcctgctcc ctgccctgc tcatctacaa ctatgcccaa     540
```

```
ggtgatcact ggcccttggg cgacttcgcc tgccgcctgg tccgcttcct cttctatgcc    600
aacctgcacg gcagcatcct cttcctcacc tgcatcagct ccagcgcta cctgggcatc    660
tgccacccgc tggcccctg gcacaaacgt gggggccgcc gggctgcctg gctagtgtgt    720
gtagccgtgt ggctggccgt gacaacccag tgcctgccca cagccatctt cgctgccaca    780
ggcatccagc gtaaccgcac tgtctgctat gacctcagcc cgcctgccct ggccacccac    840
tatatgccct atggcatggc tctcactgtc atcggcttcc tgctgccctt tgctgccctg    900
ctggcctgct actgtctcct ggcctgccgc ctgtgccgcc aggatgggcc ggcagagcct    960
gtgggcccagg agcggcgtgg caaggcggcc cgcatggccg tggtggtggc tgctgccttt   1020
gccatcagct tcctgccttt tcacatcacc aagacagcct acctggcagt gcgctcgacg   1080
ccgggcgtcc cctgcactgt attggaggcc tttgcagcgg cctacaaagg cacgcggccg   1140
tttgccagtg ccaacagcgt gctggacccc atcctcttct acttcaccca gaagaagttc   1200
cgccggcgac acatgagct cctacagaaa ctcacagcca atggcagag caggtcgc       1260
tgagtcctcc aggtcctggg cagccttcat atttgccatt gtgtccgggg caccaggagc   1320
cccaccaacc ccaaaccatg cggagaatta gagttcagct cagctgggca tggagttaag   1380
atccctcaca ggacccagaa gctcaccaaa aactatttct tcagcccctt ctctggccca   1440
gaccctgtgg gcatggagat ggacagacct gggcctggcc cttgagaggt cccagtcagc   1500
catggagagc tggggaaacc acattaaggt gctcacaaaa atacagtgtg acgtgtactg   1560
tcaaaaaaaa a                                                        1571
```

<210> SEQ ID NO 24
<211> LENGTH: 328
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 24

```
Met Glu Trp Asp Asn Gly Thr Gly Gln Ala Leu Gly Leu Pro Pro Thr
  1               5                  10                  15

Thr Cys Val Tyr Arg Glu Asn Phe Lys Gln Leu Leu Leu Pro Pro Val
                 20                  25                  30

Tyr Ser Ala Val Leu Ala Ala Gly Leu Pro Leu Asn Ile Cys Val Ile
             35                  40                  45

Thr Gln Ile Cys Thr Ser Arg Arg Ala Leu Thr Arg Thr Ala Val Tyr
         50                  55                  60

Thr Leu Asn Leu Ala Leu Ala Asp Leu Leu Tyr Ala Cys Ser Leu Pro
 65                  70                  75                  80

Leu Leu Ile Tyr Asn Tyr Ala Gln Gly Asp His Trp Pro Phe Gly Asp
                 85                  90                  95

Phe Ala Cys Arg Leu Val Arg Phe Leu Phe Tyr Ala Asn Leu His Gly
            100                 105                 110

Ser Ile Leu Phe Leu Thr Cys Ile Ser Phe Gln Arg Tyr Leu Gly Ile
        115                 120                 125

Cys His Pro Leu Ala Pro Trp His Lys Arg Gly Gly Arg Arg Ala Ala
    130                 135                 140

Trp Leu Val Cys Val Ala Val Trp Leu Ala Val Thr Thr Gln Cys Leu
145                 150                 155                 160

Pro Thr Ala Ile Phe Ala Ala Thr Gly Ile Gln Arg Asn Arg Thr Val
                165                 170                 175
```

| | | | | | | | | | | | | |
|---|---|---|---|---|---|---|---|---|---|---|---|---|
| Cys | Tyr | Asp | Leu | Ser | Pro | Pro | Ala | Leu | Ala | Thr | His | Tyr | Met | Pro | Tyr |
| | | | 180 | | | | | 185 | | | | | 190 | | |

Cys Tyr Asp Leu Ser Pro Pro Ala Leu Ala Thr His Tyr Met Pro Tyr
            180                 185                 190

Gly Met Ala Leu Thr Val Ile Gly Phe Leu Leu Pro Phe Ala Ala Leu
        195                 200                 205

Leu Ala Cys Tyr Cys Leu Leu Ala Cys Arg Leu Cys Arg Gln Asp Gly
    210                 215                 220

Pro Ala Glu Pro Val Ala Gln Glu Arg Arg Gly Lys Ala Ala Arg Met
225                 230                 235                 240

Ala Val Val Val Ala Ala Phe Ala Ile Ser Phe Leu Pro Phe His
                245                 250                 255

Ile Thr Lys Thr Ala Tyr Leu Ala Val Arg Ser Thr Pro Gly Val Pro
            260                 265                 270

Cys Thr Val Leu Glu Ala Phe Ala Ala Tyr Lys Gly Thr Arg Pro
        275                 280                 285

Phe Ala Ser Ala Asn Ser Val Leu Asp Pro Ile Leu Phe Tyr Phe Thr
    290                 295                 300

Gln Lys Lys Phe Arg Arg Arg Pro His Glu Leu Leu Gln Lys Leu Thr
305                 310                 315                 320

Ala Lys Trp Gln Arg Gln Gly Arg
                325

<210> SEQ ID NO 25
<211> LENGTH: 1116
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 25

```
atggatcgag gtgccaagtc ctgccctgcc aacttcttgg cagctgccga cgacaaactc      60
agtgggttcc aggggactt cctgtggccc atactggtgg ttgagttcct ggtggccgtg     120
gccagcaatg gcctggccct gtaccgcttc agcatccgga agcagcgccc atggcacccc     180
gccgtggtct ctctctgtcca gctggcagtc agcgacctgc tctgcgctct gacgctgccc     240
cgctggccg cctacctcta tccccccaag cactggcgct atggggaggc cgcgtgccgc     300
ctggagcgct tcctcttcac ctgcaacctg ctgggcagcg tcatcttcat cacctgcatc     360
agcctcaacc gctacctggg catcgtgcac cccttcttcg cccgaagcca cctgcgaccc     420
aagcacgcct gggccgtgag cgctgccggc tgggtcctgg ccgccctgct ggccatgccc     480
acactcagct tctcccacct gaagaggccg cagcagggg cgggcaactg cagcgtggcc     540
aggcccgagg cctgcatcaa gtgtctgggg acagcagacc acgggctggc ggcctacaga     600
gcgtatagcc tggtgctggc ggggttgggc tgcggcctgc cgctgctgct cacgctggca     660
gcctacggcg ccctcgggcg ggccgtgcta cgcagcccag gcatgactgt ggccgagaag     720
ctgcgtgtgg cagcgttggt ggccagtggt gtggccctct acgccagctc ctatgtgccc     780
taccacatca tgcgggtgct caacgtggat gctcggcggc gctggagcac cgctgcccg     840
agctttgcag acatagccca ggccacagca gccctggagc tggggcccta cgtgggctac     900
caggtgatgc ggggcctcat gcccctggcc ttctgtgtcc accctctact ctacatggcc     960
gcagtgccca gctgggctg ctgctgccga cactgcccg gctacaggga cagctggaac    1020
ccagaggacg ccaagagcac tggccaagcc ctgcccctca tgccacagc cgcccctaaa    1080
ccgtcagagc cccagtcccg tgagctgagc caatga                              1116
```

<210> SEQ ID NO 26
<211> LENGTH: 371
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 26

```
Met Asp Arg Gly Ala Lys Ser Cys Pro Ala Asn Phe Leu Ala Ala Ala
 1               5                  10                  15

Asp Asp Lys Leu Ser Gly Phe Gln Gly Asp Phe Leu Trp Pro Ile Leu
             20                  25                  30

Val Val Glu Phe Leu Val Ala Val Ala Ser Asn Gly Leu Ala Leu Tyr
         35                  40                  45

Arg Phe Ser Ile Arg Lys Gln Arg Pro Trp His Pro Ala Val Val Phe
     50                  55                  60

Ser Val Gln Leu Ala Val Ser Asp Leu Leu Cys Ala Leu Thr Leu Pro
 65                  70                  75                  80

Pro Leu Ala Ala Tyr Leu Tyr Pro Pro Lys His Trp Arg Tyr Gly Glu
                 85                  90                  95

Ala Ala Cys Arg Leu Glu Arg Phe Leu Phe Thr Cys Asn Leu Leu Gly
            100                 105                 110

Ser Val Ile Phe Ile Thr Cys Ile Ser Leu Asn Arg Tyr Leu Gly Ile
        115                 120                 125

Val His Pro Phe Phe Ala Arg Ser His Leu Arg Pro Lys His Ala Trp
    130                 135                 140

Ala Val Ser Ala Ala Gly Trp Val Leu Ala Ala Leu Leu Ala Met Pro
145                 150                 155                 160

Thr Leu Ser Phe Ser His Leu Lys Arg Pro Gln Gln Gly Ala Gly Asn
                165                 170                 175

Cys Ser Val Ala Arg Pro Glu Ala Cys Ile Lys Cys Leu Gly Thr Ala
            180                 185                 190

Asp His Gly Leu Ala Ala Tyr Arg Ala Tyr Ser Leu Val Leu Ala Gly
        195                 200                 205

Leu Gly Cys Gly Leu Pro Leu Leu Leu Thr Leu Ala Ala Tyr Gly Ala
    210                 215                 220

Leu Gly Arg Ala Val Leu Arg Ser Pro Gly Met Thr Val Ala Glu Lys
225                 230                 235                 240

Leu Arg Val Ala Ala Leu Val Ala Ser Gly Val Ala Leu Tyr Ala Ser
                245                 250                 255

Ser Tyr Val Pro Tyr His Ile Met Arg Val Leu Asn Val Asp Ala Arg
            260                 265                 270

Arg Arg Trp Ser Thr Arg Cys Pro Ser Phe Ala Asp Ile Ala Gln Ala
        275                 280                 285

Thr Ala Ala Leu Glu Leu Gly Pro Tyr Val Gly Tyr Gln Val Met Arg
    290                 295                 300

Gly Leu Met Pro Leu Ala Phe Cys Val His Pro Leu Leu Tyr Met Ala
305                 310                 315                 320

Ala Val Pro Ser Leu Gly Cys Cys Cys Arg His Cys Pro Gly Tyr Arg
                325                 330                 335

Asp Ser Trp Asn Pro Glu Asp Ala Lys Ser Thr Gly Gln Ala Leu Pro
            340                 345                 350
```

-continued

```
Leu Asn Ala Thr Ala Ala Pro Lys Pro Ser Glu Pro Gln Ser Arg Glu
        355                 360                 365
Leu Ser Gln
    370
```

PURINERGIC MODULATION OF SMELL

I. CROSS-REFERENCE TO RELATED APPLICATIONS

This application claims the benefit of U.S. provisional application Ser. No. 60/428,140, filed Nov. 21, 2002. This application is hereby incorporated by this reference in its entirety for all of its teachings.

II. ACKNOWLEDGEMENTS

This invention was made with government support under federal grants DC04953 and DC02994 awarded by the NIH and NIDCD. The Government has certain rights to this invention.

III. BACKGROUND

A longstanding dogma, based on lack of efferent synapses, is that odor sensitivity is not modulated at the level of the olfactory receptor neurons (ORNs). The sensation of smell occurs in part by the activation of smell receptors present on the ORNs. This activation begins through contact of the chemical signature responsible for the odor with a smell receptor on the ORN. There is a need to be able to modulate sensitivity to smell, to for example, decrease sensitivity to smell in noxious environments and increase sensitivity to smell for environments in which it is desirable to smell the odors. Disclosed are methods and compositions which modulate the sensitivity to odor responsiveness.

IV. SUMMARY

As embodied and broadly described herein, the disclosed compositions and methods, in one aspect, relate to the modulation of smell. It is to be understood that both the foregoing general description and the following detailed description are exemplary and explanatory only and are not restrictive.

V. BRIEF DESCRIPTION OF THE DRAWINGS

The accompanying drawings, which are incorporated in and constitute a part of this specification, illustrate several embodiments of the compositions and methods and together with the description, serve to explain the principles of the compositions and methods.

FIG. 1 shows the identification of purinergic receptors in the olfactory epithelium (OE). FIG. 1(A) shows RT-PCR analysis of $P2X_2$ and $P2Y_2$ mRNA in rat OE and bulb. The 643-bp product represents the $P2Y_2$ isoform; the 499-bp product represents the $P2X_{2-1}$ isoform, and the 292-bp product is the $P2X_{2-2}$ isoform. Control β-actin (867 bp) and neuron specific enolase (NSE; 753 bp) RT-PCR reactions are shown. +, Indicates reverse transcribed mRNA; –, indicates omission of reverse transcriptase. FIGS. 1(B, C) show neonatal mouse OE showing punctate $P2X_1$- and $P2X_4$-IR (green) in olfactory marker protein (OMP)-positive (red) axons and olfactory receptor neurons (ORNs; closed arrowheads) and in OMP-negative ORNs and basal cells (open arrowheads). SC, sustentacular cell layer; BC, basal cell layer; NL, nerve layer; C, cribriform plate; NB, nerve bundle. FIG. 1(D) shows neonatal mouse P2Y2 receptor-IR (green) occurs in ORNs (closed arrowheads), in the sustentacular cell layer (open arrowheads), and in a Bowman's gland (BG, *). FIG. 1(E) shows P2X1 receptor antibody preabsorption. (LP, lamina propria) All scale bars, 20 μM.

FIG. 2 shows ATP evokes inward currents and increases intracellular $Ca^{2+}$ in cultured mouse olfactory receptor neurons (ORNs). (A) Current responses to 10 μM ATP in two nystatin-patched ORNs held at −110 mV. Lower trace shows the ATP stimulus profile recorded separately with an open electrode. Inset, enlarged, compressed view of current from cell 1. (B) Confocal images from fluo-4 AM loaded ORNs taken before (left), and during (right) superfusion of 5 μM ATP. Scale bar, 50 μm. (C) Representative fluorescence (F) increases from cells a and b in (B) in response to ATP (1-10 μM). (D) Dose-response relation for maximum % ΔF/F increases, relative to 10 μM ATP (mean±S.E.M.; n=58 ORNs for each concentration; $EC_{50}$=1.6 μM). (E) Representative traces from 2 ORNs that responded to ATP (10 μM; arrowhead) in normal $Ca^{2+}$ and in 0 $Ca^{2+}$+EGTA (open bar).

Figure 3:
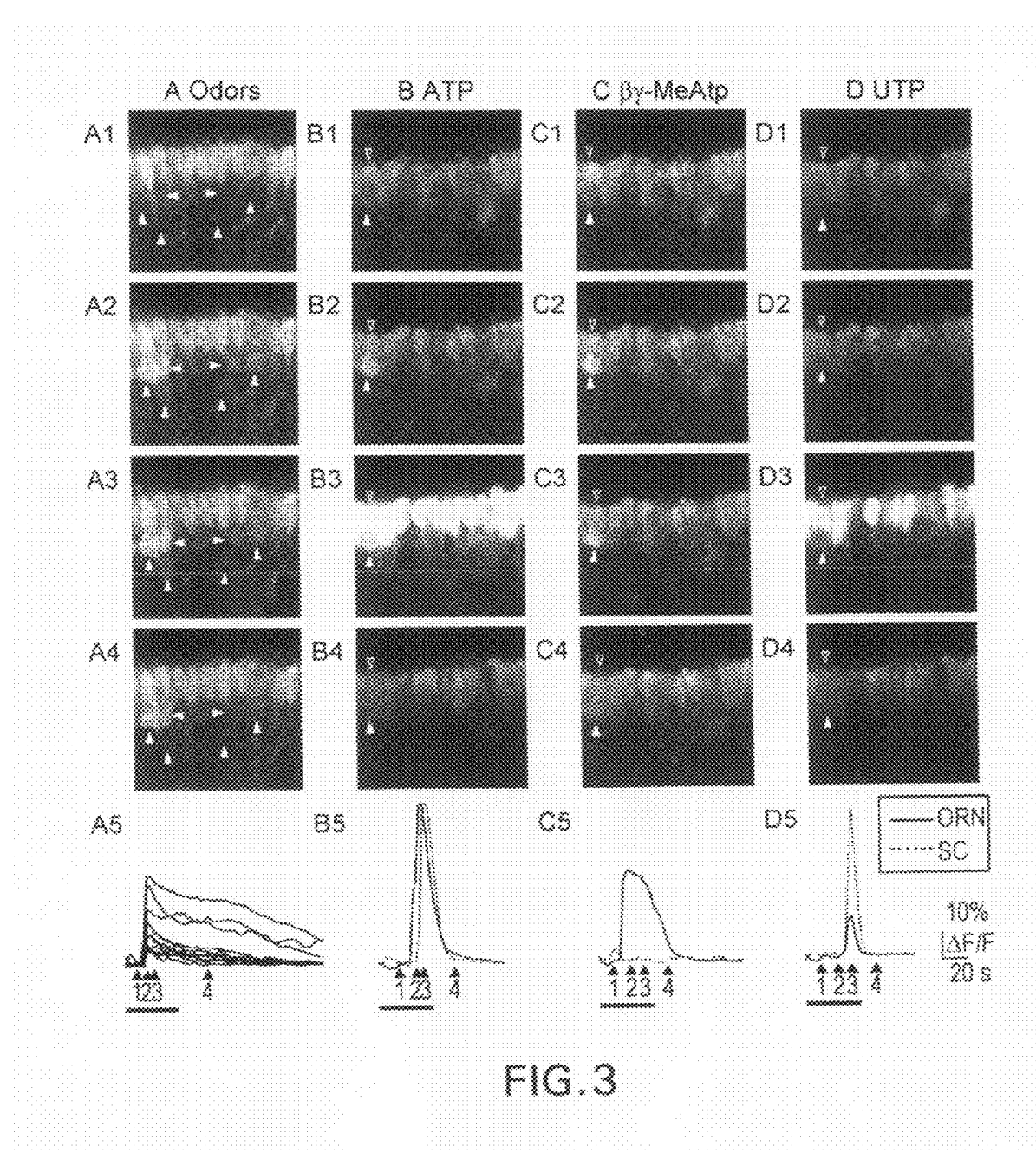

FIG. 3 shows that odor and purinergic receptor (P2R) agonists evoke increases in $[Ca^{2+}]_i$. See also Supplementary Information. FIGS. 3(A1-D4) show confocal images from a fluo4 AM-loaded mouse olfactory epithelium (OE) slice during application of (A) odors (10 μM n-amyl acetate+10 μM R-carvone), (B) 10 μM ATP, (C) 10 μM βγ-methylene ATP (βγ-MeATP), or (D) 10 μM UTP. FIGS. (A5-D5) show time course of odor- and P2R-agonist-evoked $Ca^{2+}$ transients. Time points indicated by black triangles correspond to frame numbers in A1-D4. Representative odor-responsive olfactory receptor neurons RNs) are indicated by solid white triangles (a1-a4; 6/11 ORNs marked) and as solid lines in a5. One odor-responsive ORN (solid triangle in b1-d4) and one sustentacular cell (SC, open triangle in B1-D4) are shown in the time course (B5-D5).

Figure 4A:
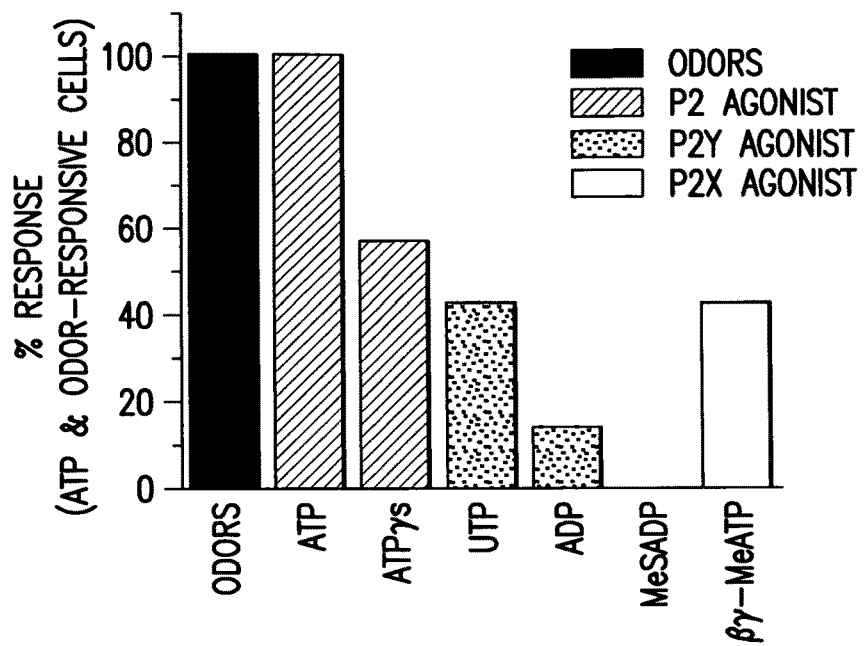
Figure 4B:
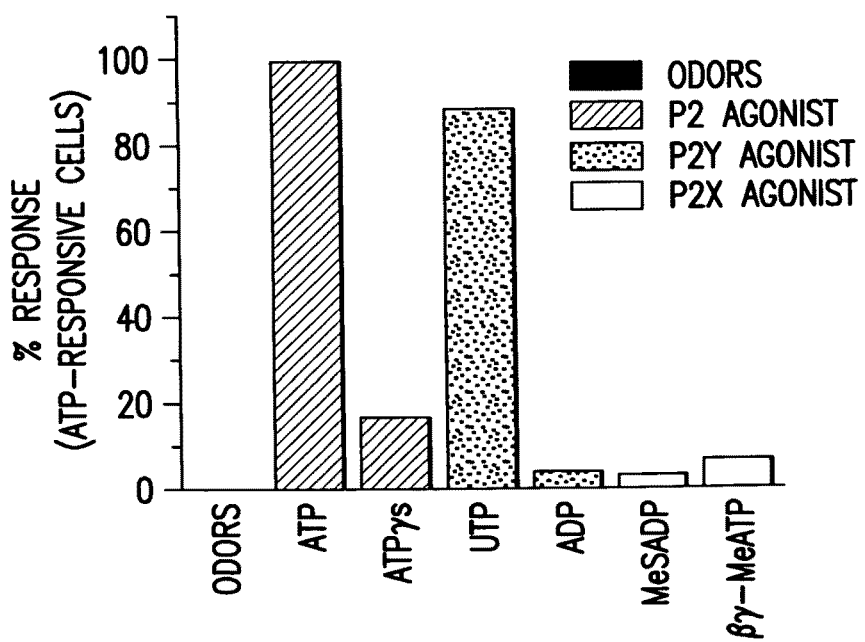

FIG. 4 shows a frequency of response to purinergics in ORNs and sustentacular cells. Shown are the percentages of ATP sensitive ORNs, FIG. 4(A); identified by odor responsiveness; n=14), and SCs, FIG. 4(B); identified by location and lack of odor response; n=122), that had increases in $[Ca^{2+}]_i$ evoked by non-selective purinergic receptor agonists (ATP, ATPγS), P2Y-selective agonists (UTP, ADP, MeSADP) and P2X-selective agonists (βγ-MeATP).

Figure 5A:
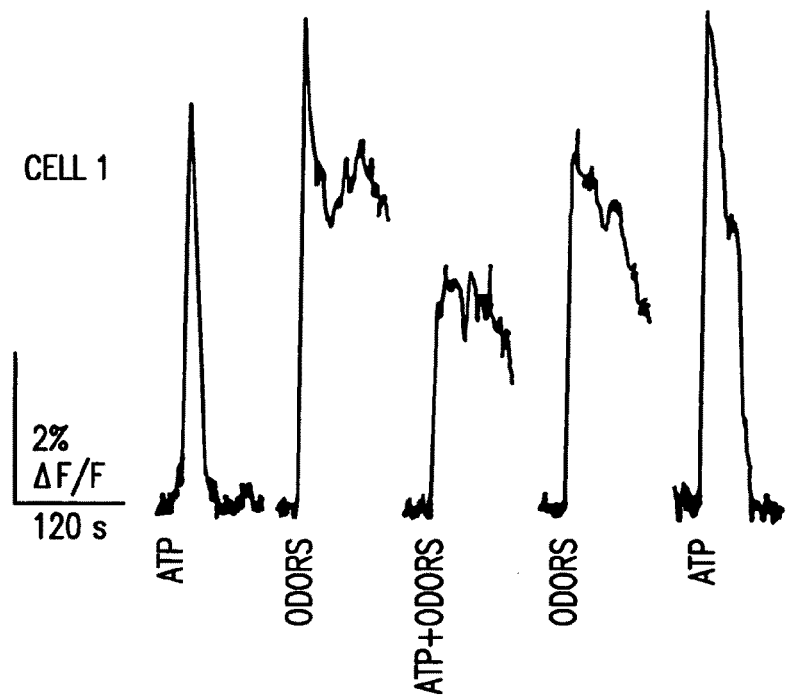
Figure 5B:
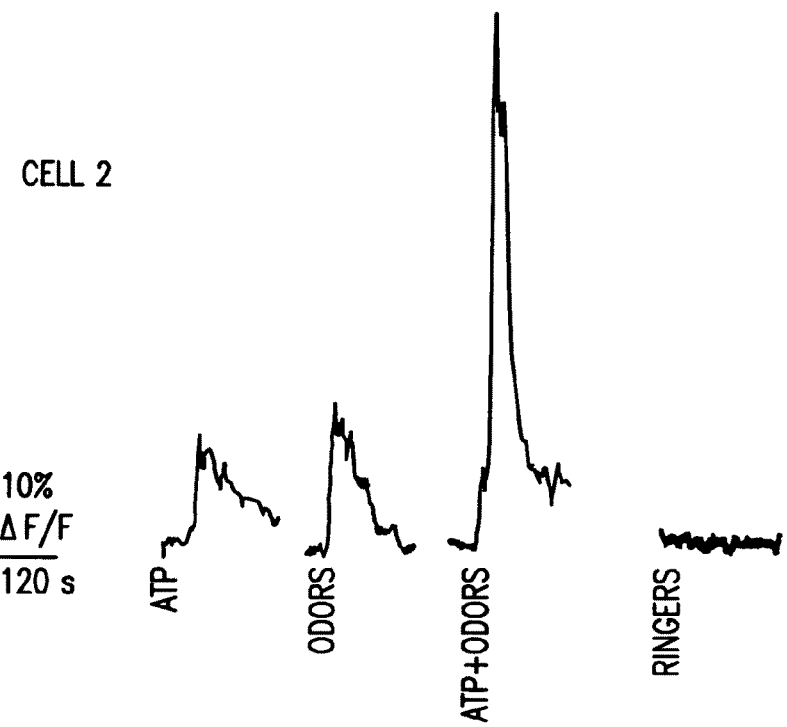
Figure 5C:
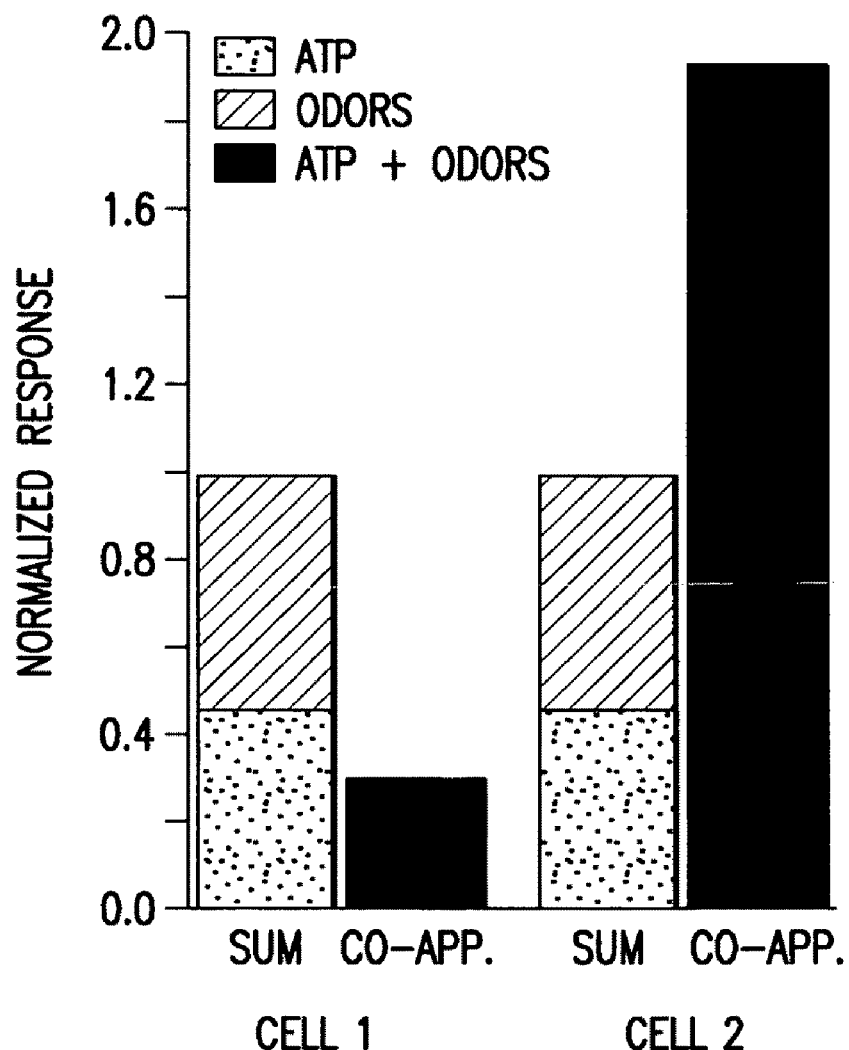

FIG. 5 shows that ATP modulates odor responses. FIG. 5(A) Suppression or FIG. 5(B) enhancement of $[Ca^{2+}]_i$ due to co-application (Co-App.) compared to the summed response of ATP and odor. Shown are responses to odor (10 μM n-amyl acetate+10 μM R-carvone), 10 μM ATP, control Ringers solution, or co-application of odor+ATP from individual mouse ORNs in olfactory epithelium slices. FIG. 5(C) Bar graph showing suppression and enhancement from the 2 individual ORNs shown in A and B. The sum of the responses to individual application of ATP and odor were normalized to 1.0 (stacked bars) and the response to co-application of ATP and odor were normalized to the summed response (black bars).

FIG. 6 shows the activation of specific purinergic receptor subtypes modulates odor responses. FIGS. 6 (A, C, E) Representative calcium transients in response to odor (10 μM n-amyl acetate+10 μM R-carvone), 10 μM purinergic receptor (P2) agonists, or co-application of odor+P2 agonists from individual mouse ORNs in Fluo4 AM loaded olfactory epithelium slices. Black triangles correspond to the time of loop injection of the odors or P2 agonists. Black circles correspond to the predicted peak amplitude of co-application (obtained by adding the estimated odor and P2 agonist values; refer to data analysis section for details). (B, D, F) Responses to individual application of P2 agonists and odor were normalized to the sum of each response and averaged (stacked bars). The responses to co-application of P2 agonists and odor were normalized to the summed individual responses and averaged (black bars). The recoveries, obtained after co-application, were also normalized to the initial summed response. Bar graphs depict normalized peak Ca$^{2+}$ transient amplitudes (mean+s.e.m.). (A-B) Co-application of 10 μM βγ-methylene ATP (βγ-MeATP) and odors enhanced the calcium transient amplitude in 2/16 ORNs from 2 slices. (C-D) Co-application of 10 μM βγ-MeATP suppressed the calcium transient amplitude in 12/16 ORNs from 6 slices. (E-F) Co-application of 10 μM ADPβS and odors reduced the calcium transient amplitude. N=15 ORNs from 5 slices.

Figure 7A:
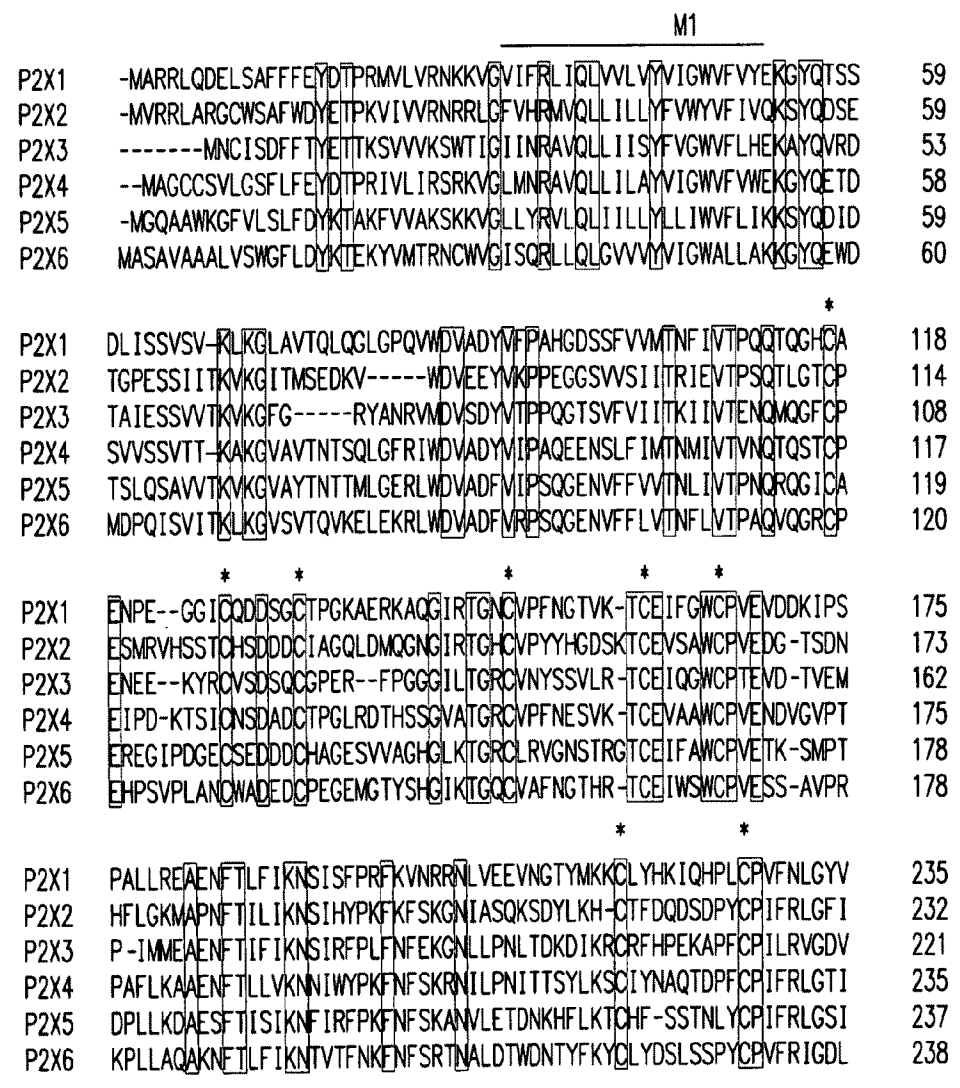

FIG. 7 shows examples of the growing family of ATP-gated ion channels. The predicted primary amino acid sequences of cloned P2X$_1$-P2X$_6$ receptor subtypes show that these proteins share approximately 40% sequence identity (gray shading) overall. Ten invariant cysteine residues (*) located within the presumptive extracellular loop may be essential for stabilizing a ligand-binding pocket through the formation of specific disulfide bonds. Putative transmembrane-helices are delimited with black bars labeled M1 and M2. A potential pore loop region akin to that found in potassium channels corresponds to the portion of M2 denoted as (H5).

Figure 8:
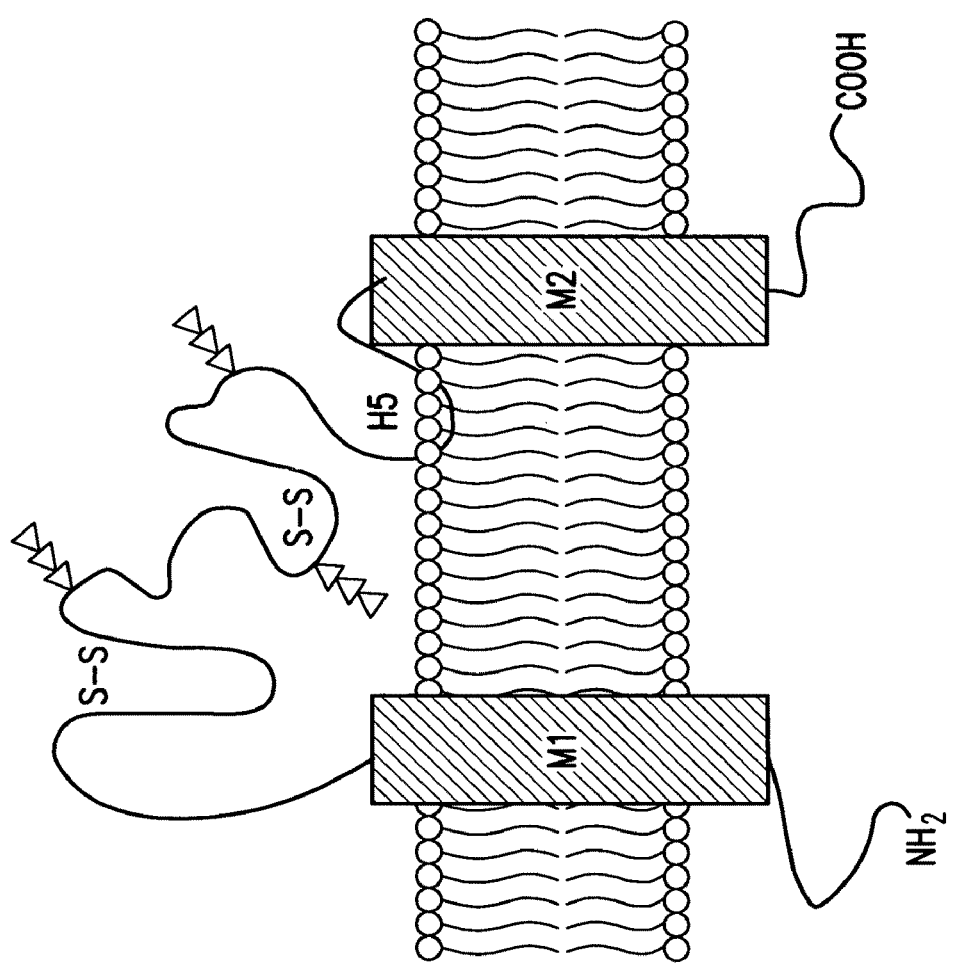

FIG. 8 shows a diagram depicting a proposed transmembrane topology for P2X2 protein showing both N- and C-terminals in the cytoplasm. Two putative membrane spanning segments (M1 and M2) traverse the lipid bilayer of the plasma membrane and are connected by a hydrophilic segment of 270 amino acids. This putative extracellular domain is shown containing two disulfide-bonded loops (S—S) and three N-linked glycosyl chains (triangles). The P2X2 cDNA was sequenced on both strands using Sequanase. (From Brake et al., 1994).

Figure 9:
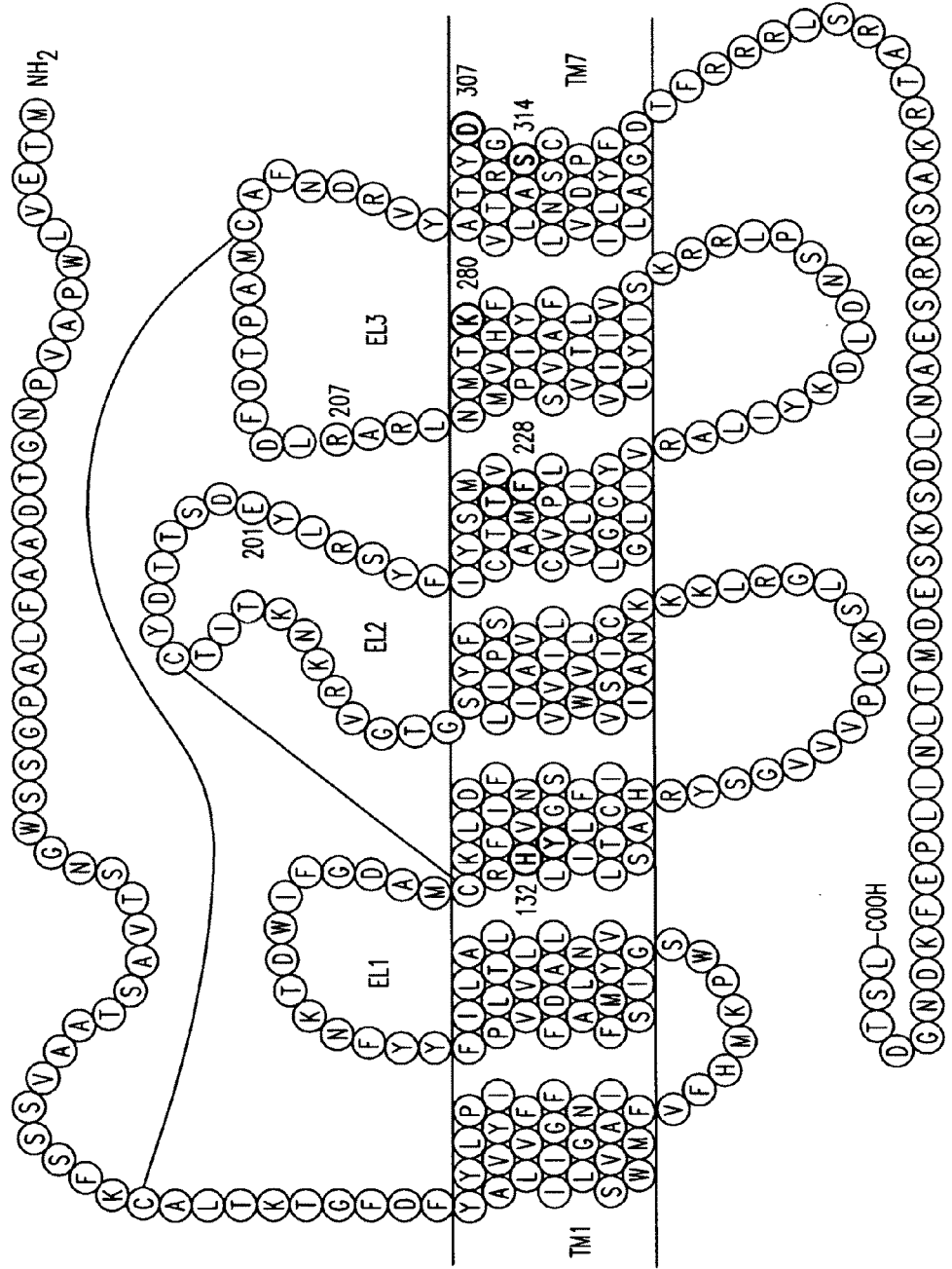

FIG. 9 shows a predicted secondary structure of the human P2Y1-receptor. Bold circles and letters highlight amino acids that most likely contribute to the nucleotide binding site within the transmembrane regions. A change of these residues by site-directed mutagenesis caused both an increase in half-maximal concentrations of agonists such as 2-methylthio-ADP activating phospholipase C (Jiang et al. 1997) and a reduction of the antagonistic potency of the nucleotide antagonist MRS 2179 (Moro et al. 1998). The dashed lines show predicted disulphide bridges (Hoffmann et al. 1999). Glu at the position 209 and Arg at the position 287 may form additional (probably low affinity) binding sites ("meta-binding sites"; see Moro et al. 1999). Potential sites for N-linked glycosylation are not indicated (TM transmembrane region, EL extracellular loop).

FIG. 10 shows the alignment of the amino acid composition of the predicted transmembrane regions (TMs) 3, 5, 6 and 7 of the human P2Y$_1$-, P2Y$_2$-, P2Y$_4$-, P2Y$_6$- and P2Y$_{11}$-receptors (for each subtype, the principal physiological agonist is shown in parentheses; please note that the human P2Y$_2$-receptor is activated by both UTP and ATP). Bold letters show a pattern of similarity in amino acid composition, which may be responsible for the pharmacological properties of the subtype. The respective residues are conserved within species. Underlined letters indicate a reduction or loss in functional responses of the (human) P2Y$_1$- or (murine) P2Y$_2$- receptor after replacement of that residue by site-directed mutagenesis. Italic letters indicate that a replacement had failed to change the responses (see Erb et al. 1995; Jiang et al. 1997).

Figure 11C:
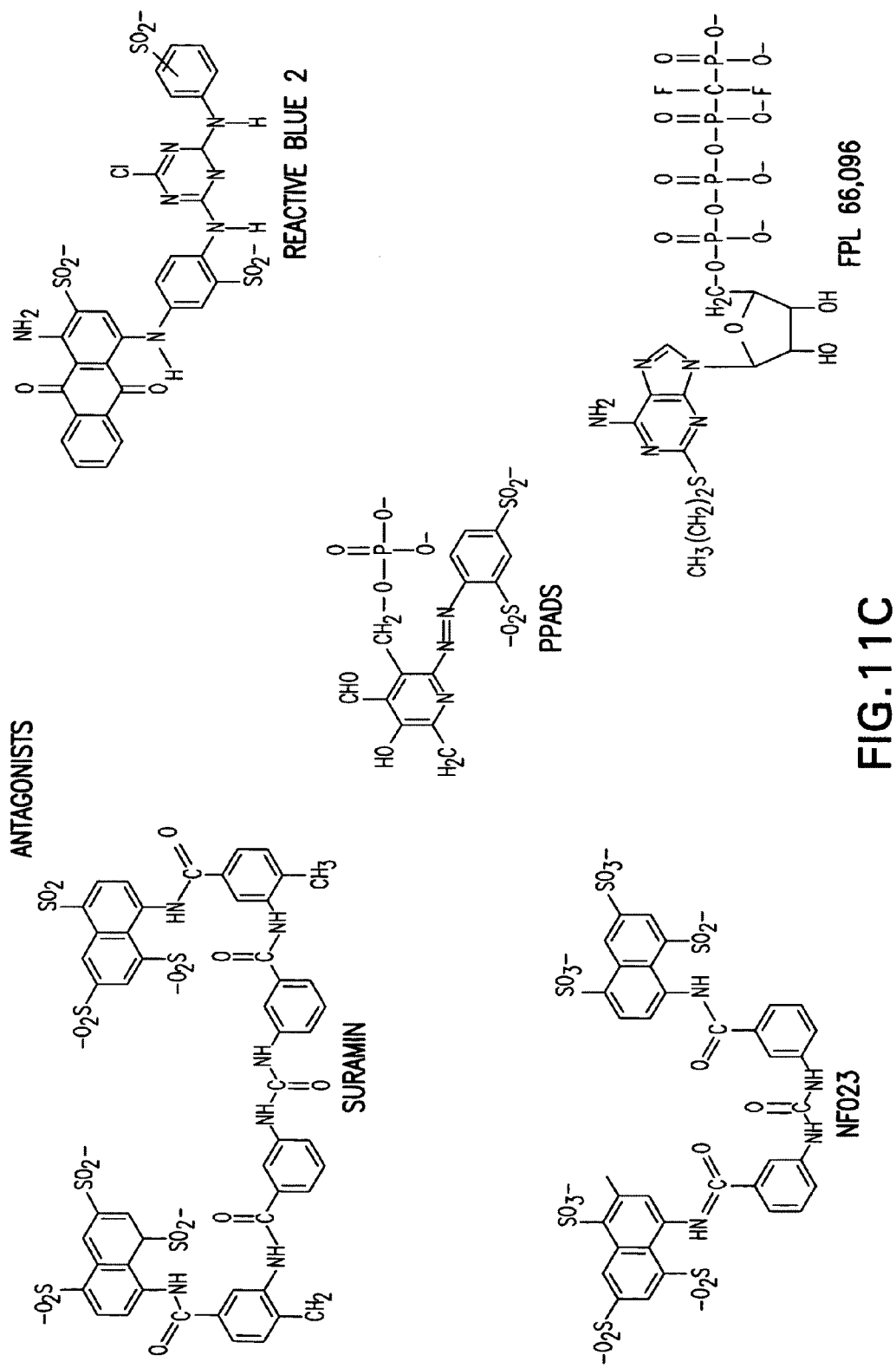

FIG. 11 shows the chemical structure of some key agonists and antagonists at P2 receptors. (Adapted from Windscheif, 1996).

FIG. 12 shows the results of the addition of antagonists and odor stimulants on nerve cells. Representative normalized calcium transients in response to odor in the absence (A) or presence (B) of P2 receptor antagonists (100 uM suramin 25 uM PPADS) from individual mouse ORNs in fluo-4-AM-loaded OE slices. Filled triangles correspond to the time of loop injection of the odors. Slices were pretreated for 3 min with Ringer's solution or P2 receptor antagonists (open columns). C, Average peak calcium transient amplitudes are shown (means+SEM), as are the predicted peak amplitudes (filled circles) for the second application (n=30 ORNs from seven slices for control and n=22 ORNs from 12 slices for P2 receptor antagonists). The asterisk indicates a significant increase in [Ca2+]i in the observed compared with predicted (p<0.024, paired Student's t test). D, Representative traces depicting basal fluorescence levels when bath is switched at 10 sec (open column) from Ringer's solution to either P2 receptor antagonists (solid lines) or Ringer's solution (dotted lines). The fluorometric signals shown are expressed as relative fluorescence change, $\Box$F/F (F−F0)/F, where F0 is calculated from the linear rate of decay during the first 15 sec of the recording (F0=mX +b). Thus, values of 0 represent no change in fluorescence and calcium levels, negative values represent decreases in calcium, and positive values represent increases in basal calcium levels.

Figure 13A:
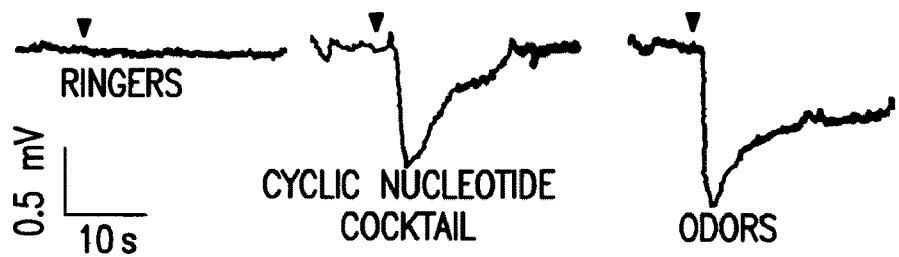

FIG. 13 shows ATP suppresses cyclic nucleotide-induced electrical responses in olfactory epithelium. (A) shows representative EOG responses from OE slices attributable to Ringer's solution, odor, and a cyclic nucleotide mixture (100 μM IBMX, 50 μM CPT-cAMP, and 50 μM 8-Br-cGMP). Filled triangles correspond to the time of loop injection of the test solutions. (B) shows representative on-cell current-clamp recording from an ORN in an OE slice. Various test solutions were superfused onto the slice for 30 seconds, indicated by the shaded region. The cell was allowed to recover for 7 minutes after each test application. Note that the coapplication of ATP (10 μM) and the mixture suppressed the evoked membrane potential changes. (C) shows the electrical activity from each ORN was integrated from baseline, normalized to the initial cyclic nucleotide mixture response, and averaged (means+SEM). *p<0.05, Newman-Keuls post hoc test. N=3 from three slices, also indicated in each column.

VI. DETAILED DESCRIPTION

The present compositions and methods can be understood more readily by reference to the following detailed description and the Examples included therein and to the Figures and their previous and following description.

Before the present compounds, compositions, articles, devices, and/or methods are disclosed and described, it is to be understood that the compositions and methods are not limited to specific synthetic methods, specific recombinant biotechnology methods unless otherwise specified, or to particular reagents unless otherwise specified, as such can, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art, which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

"Coapplication" is defined as the application of one or more substances simultaneously, such as in the same formulation or consecutively, within a time frame such that each substance is active during a point when the other substance or substances are active.

The terms "higher," "increases," "elevates," or "elevation" refer to increases above basal levels, e.g., as compared to a control. The terms "low," "lower," "reduces," or "reduction" refer to decreases below basal levels, e.g., as compared to a control. For example, basal levels are normal its vivo levels prior to, or in the absence of, or addition of an agent such as an agonist or antagonist.

The term "test compound" is defined as any compound to be tested for its ability to interact with a purinergic receptor, e.g., an epithelial $Ca^{2+}$ entry channel agonist or antagonist. Also, "test components" include, for example, drugs, molecules, and compounds that come from combinatorial libraries where thousands of such ligands are screened by drug class.

The terms "control levels" or "control cells" are defined as the standard by which a change is measured, for example, the controls are not subjected to the experiment, but are instead subjected to a defined set of parameters, or the controls are based on pre- or post-treatment levels.

Throughout this application, various publications are referenced. The disclosures of these publications in their entireties are hereby incorporated by reference. The references disclosed are also individually and specifically incorporated by reference herein for the material contained in them that is discussed in the sentence in which the reference is relied upon.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular ATP analog is disclosed and discussed and a number of modifications that can be made to a number of molecules including the ATP analog are discussed, specifically contemplated is each and every combination and permutation of the ATP analog and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E; and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions, such as enhancing or reducing odor sensitivity. Disclosed herein are certain structural requirements for performing the disclosed functions, and it is understood that there are a variety of structures which can perform the same function which are related to the disclosed structures, and that these structures will ultimately achieve the same result, for example stimulation or inhibition of smell.

B. Compositions and Methods

Purinergic nucleotides are important neuromodulators of auditory and visual systems. Disclosed herein is the existence and activity of purinergic receptors in mammalian olfactory epithelium, such as mouse or human, determined through immunohistochemistry, electrophysiology and calcium imaging. P2X and P2Y receptors, such as P2Y2, P2X1 and P2X4 immunoreactivity (-IR) was present on the dendrites, soma and axons of olfactory marker protein⁺ (OMP) ORNs, and in the olfactory nerve, glomular and mitral cell layers of the olfactory bulb. In addition, P2Y2-IR was observed in the sustentacular cell layer of the epithelium. Application of ATP (10 µM) onto perforated patched mouse ORNs evoked inward currents with two distinct latent periods, indicating involvement of both rapidly activating ligand-gated P2X receptors and G-protein coupled P2Y receptors, which should have a slow onset of activation. Application of ATP (10 µM) evoked a rapid transient increase in intracellular calcium ($[Ca^{2+}]_i$). In the absence of external $Ca^{2+}$, ATP-evoked larger calcium transients than responses in the presence of $Ca^{2+}$ indicating that at least part of the signal results from release from intracellular $Ca^{2+}$ stores implicating P2Y receptor contribution to ATP-mediated $Ca^{2+}$ transients. An olfactory epithelial (OE) slice preparation and confocal imaging was used to measure changes in $[Ca^{2+}]_i$ in fluo4 acetoxymethyl ester (AM) loaded OE slices in response to odor and purinergic nucleotide application. Use of selective purinergic receptor agonists demonstrated that P2X and P2Y receptor agonists evoke increases in $[Ca^{2+}]_i$ in ORNs with equal frequency and that P2Y but not P2X receptor agonists evoke calcium transients in sustentacular cells. $[Ca^{2+}]_i$ levels were measured in response to odor, ATP, or odor+ATP. In most cells, ATP reduced the summed odor-induced changes in $Ca^{2+}$ however, some cells exhibited an increase in evoked $[Ca^{2+}]_i$ increase, indicating an increased effect. Collectively, the data indicates that P2X and P2Y receptor subtypes are expressed in the olfactory epithelium and that P2X and P2Y agonists and antagonists modulation of odor responses, such as the agonist ATP, can be dependent on the subtype(s) of purinergic receptors expressed.

Disclosed herein is direct evidence that ATP and ATP analogs modulate odor responses in olfactory receptor neurons. ATP released in the olfactory epithelium following noxious stimuli provides a physiological source for a neuromodulatory substance independent of efferent innervation. Peripheral ATP-mediated odor suppression is a mechanism for reduced olfactory sensitivity during exposure to olfactotoxins. Methods for modulating the sensitivity to smell of a subject are disclosed.

1. P2X and P2Y Purinergic Receptors

P2X receptors form $Ca^{2+}$-permeable nonselective cation channels that allow $Ca^{2+}$ influx from the extracellular fluid. Most of the 8 functional P2Y receptors identified to date act via G-protein coupling to activate phospholipase C, leading to production of inositol triphosphates and mobilization of $Ca^{2+}$ from internal stores (Dubyak and el-Moatassim, 1993); however, a few P2Y receptors couple to adenylate cyclase (Ralevic and Burnstock, 1998). All of the components of both transduction pathways have been identified in ORNs (Schild and Restrepo, 1998).

Although purines are odorants for aquatic vertebrates (Kang and Caprio, 1995) and invertebrates (Carr, W. E., et al., Environ. Health Perspect. 71, 31-46 (1987)), disclosed herein, extracellular purinergic nucleotides and their receptors in mammalian, such as human, olfactory epithelium exist. Disclosed herein, RT-PCR and immunohistochemistry and physiological studies, show that sustentacular support cells express P2Y receptors and that ORNs express both P2X and P2Y receptors. Regionally localized purinergic receptors are consistent with extracellular ATP having multiple roles in the peripheral olfactory system. Furthermore, it is shown herein that ATP differentially modulates the odor responsiveness of ORNs. This indicates that the complement of P2X and/or P2Y receptor subtypes expressed in the ORN can determine whether the odor response is enhanced or inhibited in the presence of ATP.

There are two main families of purine receptors, adenosine or P1 receptors, and P2 receptors, recognizing primarily ATP, ADP, UTP, and UDP (Table 1). Adenosine/P1 receptors couple to G proteins and have been further subdivided, based on molecular, biochemical, and pharmacological evidence into four subtypes, $A_1$, $A_{2A}$, $A_{2B}$, and $A_3$. In contrast, P2 receptors divide into two families of ligand-gated ion channels and G protein-coupled receptors termed P2X and P2Y receptors, respectively. For example, Table 1 sets forth seven mammalian P2X receptors ($P2X_{1-7}$) and five mammalian P2Y receptors ($P2Y_1$, $P2Y_2$, $P2Y_4$, $P2Y_6$, $P2Y_{11}$) which have been cloned and characterized.

TABLE 1

Families of receptors for purines and pyrimidines
(Modified from Ralevic V, Burnstock G. Pharmacol
Rev 1998 Sep; 50(3): 413-92.)

|  | Adenosine/ P1 receptors | P2 receptors | |
| --- | --- | --- | --- |
| Natural ligands | Adenosine | ATP, ADP, UTP, UDP, Adenine dinucleotides | |
| Subgroup | — | P2X | P2Y |
| Type | G protein-coupled | Ion channel Non-selective pore | G protein-coupled |
| Subtypes | $A_1$, $A_{2A}$, $A_{2B}$, $A_3$ | $P2X_{1-7}$, $P2X_n$ | $P2Y_1$, $P2Y_2$, $P2Y_4$, $P2Y_6$, $P2Y_{11}$, $P2Y_{ADP}$ (or $P_{2T}$) Uridine nucleotide-specific |

P2X receptors are ATP-gated ion channels which mediate rapid (within 10 ms) and selective permeability to cations ($Na^+$, $Ki^+$ and $Ca^{2+}$)(Bean, 1992; Dubyak and el-Moatassim, 1993; North, 1996). They are typically found on excitable cells (smooth muscle cells, neurons, and glial cells) and mediate fast excitatory neurotransmission to ATP in both the central and peripheral nervous systems. This contrasts with the slower response (less than 100 ms) to ATP acting at metabotropic P2Y receptors, which involves coupling to G proteins and second-messenger systems. Seven functional P2X receptor proteins ($P2X_1$ to $P2X_7$) have been cloned and form homomeric ion channels with distinct pharmacological profiles when expressed in *Xenopus* oocytes (Table 2). The $P2X_7$ receptor is considered separately below, because it is functionally unique among P2X receptors in being able to act as a non-selective pore.

Functional cDNAs encoding the first two members of this family, $P2X_1$ and $P2X_2$, were isolated from vas deferens smooth muscle and PC12 pheochromocytoma cells, respectively, using an expression cloning strategy in *Xenopus* oocytes (Brake et al 1994, Valera et al 1994). In each case, expression of a single cDNA clone in oocytes or transfected mammalian cells is sufficient to direct the synthesis of functional, presumably homomeric ATP-gated ion channel complexes on the surface of these cells. $P2X_1$ and $P2X_2$ receptors are clearly related at the level of primary amino acid sequence and predicted secondary structure. Four additional members of this channel family have now been cloned using PCR-based screening strategies (Bo et al 1995, Chen et al 1995, Lewis et al 1995, Buell et al 1996, Collo et al 1996, Seguela et al 1996). All six subtypes share approximately 40% sequence identity distributed fairly evenly over their length, which ranges from 379 to 472 residues (FIG. 7).

TABLE 2

Cloned P2X receptors and typical activity profiles

| Receptor | Acession number | cDNA library source | Agonist activity | References |
| --- | --- | --- | --- | --- |
| $P2X_1$ | X83688 | Human urinary bladder | ATP > α,β-meATP | Evans et al., 1994; Valera et al., 1995; Longhurst et al., 1996 |
| (399 amino acids (aa)) | X80477 | Rat vas deferens | 2MeSATP > ATP > α,β-meATP | Valera et al., 1994 |
|  | X84896 | Mouse urinary bladder |  | Valera et al., 1996 |
| $P2X_2$ (472 aa) | U14414 | Rat PC12 cells | 2MeSATP > ATP; α,β-meATP inactive | Brake et al., 1994 |
| $P2X_{2(b)}{}^a$ (401 aa) | Y09910 | Rat cerebellum | 2MeSATP = ATP = α,β-meATP | Brändle et al., 1997; Simon et al., 1997 |

TABLE 2-continued

Cloned P2X receptors and typical activity profiles

| Receptor | Acession number | cDNA library source | Agonist activity | References |
|---|---|---|---|---|
| P2X$_3$ (397 aa) | Y07684 | Human heart, spinal cord | 2MeSATP > ATP > α,β-meATP | Garcia-Guzman et al., 1997b |
| | X90651 | Rat dorsal root ganglion cells | 2MeSATP > ATP > α,β-meATP > UTP | Chen et al., 1995a |
| | X91167 | Rat dorsal root ganglion cells | ATP > 2MeSATP > α,β-meATP | Lewis et al., 1995 |
| P2X$_4$ (388 aa) | Y07684 | Human brain | ATP >> 2MeSATP ≧ CTP > α,β-meATP | Garcia-Guzman et al., 1997a |
| | X93565 | Rat brain | ATP >> 2MeSATP ≧ CTP > α,β-meATP | Soto et al., 1996a |
| | U32497 | Rat brain | ATP > 2MeSATP >> α,β-meATP | Séguéla et al., 1996 |
| | X91200 | Rat hippocampus | ATP > 2MeSATP >> α,β-meATP | Bo et al., 1995 |
| | X87763 | Rat superior cervical ganglion | ATP; α,β-meATP inactive | Buell et al., 1996b |
| | U47031 | Rat pancreatic islet | ATP, ADP, 2MeSATP >> α,β-meATP | Wang et al., 1996 |
| P2X$_5$ (417 aa) | X92069 | Rat ganglia | ATP > 2MeSATP > ADP α,β-meATP inactive | Collo et al., 1996 |
| (455 aa) | X97328 | Rat heart | ATP > 2MeSATP > ADP | Garcia-Guzman et al., 1996 |
| P2X$_6$ | X92070 | Rat superior cervical ganglion | ATP > 2MeSATP > ADP; α,β-meATP inactive | Collo et al., 1996 |
| (379 aa) | X97376 | Rat brain | | Soto et al., 1996b |
| P2X$_7$ (595 aa) | | Mouse macrophage | BzATP > ATP > UTP ATP > UTP > BzATP | Nuttle et al., 1993 |
| | X95882 | Rat macrophage and brain | BzATP > ATP > 2MeSATP > ADP; UTP inactive | Surprenant et al., 1996 |
| | | Human monocytes | BzATP > ATP | Rassendren et al., 1997 |

$^a$Splice variant, also termed P2X$_{2-2}$.
All references are herein incorporated by reference at least for material related to a P2X or P2Y receptor.
Modified from Ralevic V, Burnstock G. Pharmacol Rev 1998 Sep; 50(3): 413-92.

Based on the amino acid sequences of cloned P2X receptor subunits, structural features of P2X receptors have been predicted. The P2X proteins that have been cloned are receptor subunits, not actual receptors since a single 2 transmembrane subunit alone cannot form an ion channel. The proteins have 379 to 472 amino acids and are believed to insert into the cell membrane to form a pore comprising two hydrophobic transmembrane domains (M1 and M2), with much of the protein occurring extracellularly as an intervening hydrophilic loop (FIG. 8). It is presumed that both amino- and carboxyl-termini are located on the intracellular side of the membrane. Based on genetic studies in C. elegans, the M2 domain of these channels forms an amphipathic α-helix whose hydrophilic face lines the pore (Hong & Driscoll 1994). Interestingly, helical wheel plots of M2 domains from each of the cloned P2X subunits show that they have similar potential to form amphipathic α-helices, despite the limited sequence homology in this region. In addition, some P2X subunits contain a region, that resembles the H5 pore loop domain of potassium channels, and it is possible that this segment (just amino-terminal to M2), also contributes to the pore of ATP-gated channels. However, there is considerable variability in the H5 domain consensus sequence, and its location relative to M2, among the six cloned P2X receptor subtypes. The overall structure of the receptor most closely resembles that of amiloride-sensitive epithelial Na$^+$ channels. The putative extracellular loop of cloned receptors P2X$_1$ to P2X$_7$ has 10 conserved cysteine residues, 14 conserved glycine residues and 2 to 6 potential N-linked glycosylation sites. It is believed that disulfide bridges may form the structural constraints needed to couple the ATP-binding site to the ion pore. Most of the conserved regions are in the extracellular loop, with the transmembrane domains being less well-conserved. As for other ligand-gated receptors, P2X receptors are believed to form a heterologous complex in biological tissues. Although their subunit stoichiometry is unknown, SDS polyacrylamide gel electrophoresis estimates of the relative molecular mass of the recombinant P2X$_1$ and P2X$_3$ receptors determined under non-denaturing conditions (Nicke et al., 1998) suggest a combination of three subunits (or multiples of three subunits).

Both cloned P2X$_7$ and endogenous P2X$_7$-like receptors are unique in that, under physiological conditions they are selectively permeable to small cations only, but in the presence of low divalent cation levels and ATP, the P2X$_7$ channel can convert to a pore, permeable to small molecules as well as ions. The P2X$_7$ receptor and its endogenous counterpart is structurally similar to other P2X receptors, except for the fact that it has a significantly longer intracellular C-terminal (240 amino acids) than other P2X receptors, of which at least the last 177 amino acids are crucial for the induction of the non-selective pore (Surprenant et al., 1996). Brief activation of the recombinant P2X$_7$ receptor and its endogenous counterpart causes rapid membrane depolarization and cation influx and is a reversible process. However, sustained activation causes an increase in permeability by allowing bidirectional transport of a variety of ions including Na$^+$, K$^+$, and Ca$^{2+}$ and small molecules with a molecular weight of less than or equal to 900 daltons, except in lymphocytes where the limit is 200-300 daltons. This effect is associated with cytotoxicity. Although cation function of the receptor is retained in a truncated P2X$_7$ receptor lacking the last 177 residues, the increased permeability is lost suggesting involvement of the cytoplasmic C terminus. The disclosed results indicate that the P2X$_7$ receptor is not typically present in mammalian olfactory epithelium.

P2Y receptors are purine and pyrimidine nucleotide receptors that are coupled to G proteins. Most P2Y receptors act via G protein coupling to activate PLC leading to the formation of IP$_3$ and mobilization of intracellular Ca$^{2+}$. Coupling to adenylate cyclase by some P2Y receptors has also been described. The response time of P2Y receptors is longer than that of the rapid responses mediated by P2X receptors because it involves 5 second-messenger systems and/or ionic conductances mediated by G protein coupling. Five mammalian P2Y receptors ($P2Y_1$, $P2Y_2$, $P2Y_4$, $P2Y_6$, $P2Y_{11}$) have been cloned, and functionally characterized and show distinct pharmacological profiles (Table 3).

charged amino acids in transmembrane regions 6 and 7 to neutral amino acids causes a 100- to 850-fold decrease in the potency of ATP and UTP, which suggests a role for these amino acids in binding purines and pyrimidines (Erb et al., 1995). In contrast, in the human P2Y, receptor, the most important residues for ATP binding are in transmembrane regions 3 and 7 on the exofacial side of the receptor (Jiang et al., 1997).

TABLE 3

Cloned P2Y receptors

| Receptor | Acession number | cDNA library source | Agonist activity | References |
|---|---|---|---|---|
| $P2Y_1$ (362 amino acids (aa)) | | Human brain | 2MeSATP > ATP >> UTP | Schachter et al., 1996 |
| | S81950 | Human prostate and ovary | 2MeSATP > ATP = ADP | Janssens et al., 1996 |
| | Z49205 | Human placenta | | Léon et al., 1995, 1997 |
| | U42030 | Human HEL cells | | Ayyanathan et al., 1996 |
| | X87628 | Bovine endothelium | 2MeSATP = ADP > ATP >> UTP | Henderson et al., 1995 |
| | U22830 | Rat insulinoma cells | 2MeSATP > 2Cl-ATP > ATP ($\alpha,\beta$-meATP inactive) | Tokuyama et al., 1995 |
| | | Rat ileal myocytes | 2MeSATP = 2ClATP > ADP > ATP (UTP inactive) | Pacaud et al., 1996 |
| | U22829 | Mouse insulinoma cells | | Tokuyama et al., 1995 |
| | U09842 | Turkey brain | 2MeSATP > ADP > ATP; (UTP inactive) | Filtz et al., 1994 |
| | X73268 | Chick brain | 2MeSATP > ATP > ADP; (UTP inactive) | Webb et al., 1993b |
| $P2Y_2$ (373 aa) | U07225 | Human CF/T43 epithelial cells | ATP = UTP >> 2MeSATP | Parr et al., 1995 |
| | | Human bone | | Bowler et al., 1995 |
| | | Rat microvascular coronary EC | | Gödecke et al., 1996 |
| | U09402 | Rat alveolar type II cells | ATP = UTP | Rice et al., 1995 |
| | L46865 | Rat pituitary | ATP = UTP > ADP = UDP > GTP | Chen et al., 1996b |
| | U56839 | Wistar Kyoto rat[a] | | Seye et al., 1996 |
| | NM_008773 | Mouse NG108-15 neuroblastoma cells | ATP = UTP > ATPγS >> 2MeSATP | Lustig et al., 1993 |
| $P2y3$[b] (328 aa) | X98283 | Chick brain | UDP > UTP > ADP > 2MeSATP > ATP | Webb et al., 1995, 1996a |
| $P2Y_4$ (352 aa) | X91852 | Human placenta | UTP > ATP = ADP[c] | Communi et al., 1996b |
| | | Human placenta | | Stam et al., 1996 |
| | U40223 | Human chromosome X | UTP > UDP (ATP inactive) | Nguyen et al., 1996 |
| | Y14705 | Rat heart | ATP = UTP = ADP = ITP = ATPγS = 2MeSATP = $Ap_4A$ > UDP | Bogdanov et al., 1998 |
| $P2Y_6$ (379 aa) | X97058 | Human placenta and spleen | UDP > UTP > ADP > 2MeSATP >> ATP | Communi et al., 1996b |
| | NM_057124 | Rat aortic smooth muscle | UTP > ADP = 2MeSATP > ATP | Chang et al., 1995 |
| | U52464 | Activated T-cells | | Southey et al., 1996 |
| $P2Y_{11}$ (371 aa) | 371 | Human placenta | ATP > 2MeSATP >>> ADP; (UTP, UDP inactive) | Communi et al., 1997 |

[a]Tissue not specified.
[b]p2y3 may be the chick homologue of the mammalian $P2Y_6$ receptor.
[c]The reported activity of UDP at the $P2Y_4$ receptor has been shown to be caused by UTP present as a contaminant.
Each of the references herein is incorporated by reference at least for material related to P2Y receptors
Modified from Ralevic V, Burnstock G. Pharmacol Rev 1998 Sep; 50(3): 413-92.

P2Y receptors are 308 to 377 amino acid proteins with a mass of 41 to 53 kDa after glycosylation. The tertiary structure of P2Y receptors is similar to that of other seven transmembrane domain G protein-coupled receptors (FIG. 9). A model of the P2Y receptor, based on the primary sequence of the P2Y, receptor and using the structural homolog rhodopsin as a G protein-coupled receptor template, has identified positively charged amino acid residues in transmembrane regions 3, 6, and 7 that may be involved in ligand binding by electrostatic interactions with the phosphates of ATP (Van Rhee et al., 1995)(FIG. 10). Several of these amino acids are conserved in other G protein-coupled receptors. Site-directed mutagenesis of the $P2Y_2$ receptor to convert positively 2. ATP and ATP Analog Activity on Purinergic Receptors Extracellular ATP plays an important role in cellular signaling and acts as a cotransmitter or neuromodulator in sensory systems (Thorne and Housley, 1996). In the olfactory system, ATP can be released from synaptic vesicles in trigeminal afferents that innervate the olfactory epithelium and detect noxious chemicals (Finger et al., 1990; Getchell and Getchell, 1992), or via plasma membrane nucleotide transport proteins (Roman et al., 1997). Furthermore, ischemic, stressed, and injured cells release ATP in large amounts. A recent toxicology study (Kilgour et al., 2000) showed that when the olfactory epithelium was damaged by noxious fumes $[ATP]_i$ significantly decreased, whereas stimulation that did not damage the olfactory epithelium did not affect $[ATP]_i$. In addition to toxic chemicals, prolonged exposure to concentrated odors, such as peppermint, will damage olfactory receptor neurons (ORNs) and induce expression of stress indicators (heat shock proteins) in sustentacular support cells (Carr et al., 2001). Therefore, both trigeminal and odorous stimulation provide sources for extracellular ATP in olfactory epithelium.

Once released, ATP can have autocrine or paracrine effects. Very low concentrations of ATP activate the two subtypes (P2X and P2Y) of purinergic receptors (0.1-10 µM)(Ralevic and Burnstock, 1998; Schwiebert and Kishore, 2001). Through either of these receptor subtypes, ATP is able to stimulate an increase in $[Ca^{2+}]_i$ (Illes et al., 2000; Koshimizu et al., 2000; Ralevic and Burnstock, 1998).

P2 receptors have broad natural ligand specificity, recognizing ATP, ADP, UTP, UDP, and the diadenosine polyphosphates (Table 1). The chemical structures of some principal P2 receptor agonists and antagonists are illustrated in FIG. 11. For example, P2X selective agonists are the stable ATP analogs α,β-meATP and β,γ-meATP, which if effective, strongly imply actions at P2X receptors (typically at $P2X_1$ and $P2X_3$ subtypes) and are generally inactive at P2Y receptors. Also useful are ADP, adenosine 5'-O-(2-thiodiphosphate)(ADPβS,) and UTP, as these are agonists at some P2Y receptors, but are weak or inactive at P2X receptors.

TABLE 4

Exemplary P2 receptor signal transduction mechanisms, agonists, and antagonists

| Family | P2X | P2Y |
|---|---|---|
| Receptor type | Ion channel: Nonselective pore[a] | G protein-coupled: $G_{q/11}$, $G_i$[b] |
| Signaling pathway | Not applicable | PLC, AC[c] K+ channels[d], $PLC_{PC}$,[e] $PLA_2$,[f] PLD[f], PKC, MAPK[g] |
| Effectors | $Ca^{2+} \gg Na^+ > K^+$ | ↑$IP_3$, ↑$Ca^{2+}$, ↑DAG ↓cAMP[c], $Ca^{2+}$, Cl, K+ currents[h] |
| Nonselective Agonists | ATP[i], ATPγS, 2MeSATP, $Ap_4A$[j] | ATP[i], ATPγS, 2MeSATP, $Ap_4A$[j] |
| P2X/P2Y-selective Agonists | α,β-meATP[l], β,γ-meATP[l], BzATP[a] | ADP[c], UTP[m], UTPγS[j], UDP[n], 2Cl-ADP[c], 2MeSADP[c], ADPβS[c], ADPβF[c] |
| Nonselective Antagonists | Suramin, PPADS, Iso-PPADS, P5P, Reactive blue 2, Reactive Red, Trypan Blue, Evans Blue, DIDS | Suramin, PPADS, Iso-PPADS, P5P, Reactive blue 2, Reactive Red, Trypan Blue, Evans Blue, DIDS |
| P2X/P2Y-selective Antagonists | NF023, NF279, KN-62[a] | ARL 67085[o], FPL 66096[o], A3P5PS[k], MRS 2179[k], 2-hexylthio-ATP[p], 2-cyclohexylthio-ATP[p] |

[a]$P2X_7$ and endogenous $P2X_7$-like receptor.
[b]$P2Y_1$ and endogenous $P2Y_1$-like receptors acting through PLC couple to $G_{q/11}$ proteins; $P2Y_1$ and endogenous $P2Y_1$-like receptors acting through adenylate cyclase couple to $G_i$ proteins; $P2Y_2$ and endogenous $P2Y_2$-like receptors, $P2Y_4$ and $P2Y_{ADP}$ receptors couple to $G_{q/11}$ and $G_i$ proteins; p2y3 and $P2Y_6$ receptors couple to $G_{q/11}$ proteins.
[c]$P2Y_1$ and endogenous $P2Y_1$-like receptors and $P2Y_{ADP}$ receptors.
[d]Some endogenous $P2Y_1$-like receptors activate K+ channels via interactions with their G protein subunits.
[e]$P2Y_1$ and endogenous $P2Y_1$-like receptor signaling; possibly downstream of PKC.
[f]$P2Y_1$ and $P2Y_2$ receptors and their endogenous counterparts; signaling possibly downstream of PKC.
[g]$P2Y_1$ and $P2Y_2$ receptors and their endogenous counterparts; signaling downstream of PKC.
[h]Secondary to activation of PLC, although activation of K+ currents by some endogenous $P2Y_1$-like receptors is via direct interactions with G protein subunits.
[i]$P2Y_1$ and $P2Y_2$ receptors and their endogenous counterparts; ATP is an antagonist at $P2Y_{ADP}$ receptors.
[j]$P2Y_2$ and endogenous $P2Y_2$-like receptors.
[k]$P2Y_1$ and endogenous $P2Y_1$-like receptors.
[l]$P2X_1$, $P2X_3$ and heteromeric $P2X_2P2X_3$ receptors.
[m]$P2Y_2$ and endogenous $P2Y_2$-like receptors and $P2Y_4$ receptors.
[n]$P2Y_6$ receptor.
[o]$P2Y_{ADP}$.
[p]$P2Y_1$ and endogenous $P2Y_1$-like receptors coupled to AC.

Abbreviations:
AC, adenylate cyclase;
ADPβF, adenosine 5'-O-(2-fluoro)-diphosphate;
ADPβS, adenosine 5'-O-(2-thio-diphosphate);
cAMP, adenosine 3',5-cyclic monophosphate;
A3P5PS, adenosine 3'-phosphate 5'-phosphosulfate;
ARL 67085,6-N,N-diethyl-D-β,γ-dibromomethylene ATP;
ATPγS, adenosine 5'-O-(3-thiotriphosphate);
BzATP, 3'-O-(4-benzoyl)benzoyl ATP;
DAG, diacylglycerol;
DIDS, 4,4'-diisothio-cyanatostilbene-2,2'-disulfonate;
FPL 66096, 2-propylthio-D-β,γ-difluoromethylene ATP;
$IP_3$, inositol 1,4,5-trisphosphate;
KN-62, 1-[N,O-bis(5-isoquinolinesulfonyl)-N-methyl-L-tyrosyl]-4-phenylpiperazine;
Iso-PPADS, pyridoxal phosphate-6-azophenyl-2',5'-disulfonic acid;
MAPK, mitogen-activated protein kinase;
α,β-meATP, α,β-methylene ATP;
β,γ-meATP, β,γ-methylene ATP;
2MeSADP, 2-methylthio ADP;
2MeSATP, 2-methylthio ATP;
MRS 2179, $N^6$-methyl modification of 2'-deoxyadenosine 3',5'-bisphosphate;

TABLE 4-continued

Exemplary P2 receptor signal transduction mechanisms, agonists, and antagonists

| Family | P2X | P2Y |
|---|---|---|

NF023, symmetrical 3'-urea of 8-(benzamido)naphthalene-1,3,5-trisulfonic acid;
NF279, 8,8'-(carbonylbis(imino-4,1-phenylenecarbonylimino-4,1-phenylenecarbonylimino))bis(1,3,5-naphthalenetrisulfonic acid);
P5P, pyridoxal-5-phosphate;
$PLC_{PC}$, phosphatidylcholine-specific phospholipase C;
PKC, protein kinase C;
$PLA_2$, phospholipase $A_2$;
PLC, phospholipase C;
PLD, phospholipase D;
PPADS, pyridoxal phosphate-6-azophenyl-2',4'-disulfonic acid;
suramin, 8-(3-benzamido-4-methylbenzamido)-naphthalene-1,3,5-trisulfonic acid;
UTPγS, uridine 5'-O-(3-thiotriphosphate).
Modified from Ralevic V, Burnstock G. Pharmacol Rev 1998 Sep; 50(3): 413-92.

3. Inhibiting Olfactory Response

As discussed herein if in an odor-ATP or analog assay, the calcium transient evoked by co-application is less than the sum of the calcium transients evoked by the individual components then there is an inhibiting effect on the olfactory response. Of the cells that responded to odor, 62% (21/26 cells) exhibited a significant decrease in the summed $[Ca^{2+}]_i$ increase. The mean suppression of all cells was 57%±5% (paired t-test, p=0.01, n=26). Thus, ATP reduced the expected combined effect of the ATP and the odor, and thus will act as an odor suppressant. Typically, activation of P2Y receptors reduced sensitivity to odors. For example, the P2Y selective agonists UTP and ADP-PS suppressed the co-application evoked calcium transient indicating they can act as odor suppressants. As discussed in the Examples, similar experiments were performed with P2X and P2Y selective agonists giving similar results.

Disclosed are compositions and methods for inhibiting the odor response of an ORN. Inhibition of the response can be determined by performing the transient calcium flux assays as discussed herein. Typically these assays can be performed in the presence or absence of the odor. Thus, compositions which inhibit the ORN response can be compositions which in a calcium transient flux assay, the presence of the composition and the odor together, produces a transient calcium flux that is less than the sum of the odor induced flux alone and the composition induced flux alone. For example, if the amount of calcium flux in the presence of a composition and an odor is A, and the amount of the calcium flux in the presence of the composition alone is B and the amount of the calcium flux in the presence of the odor alone is C then if A<B+C, the composition can be said to inhibit the ORN response and the composition can inhibit a smell response. Disclosed are compositions wherein the combined effect of the composition and odor (A) is less than or equal to 95%, 90%, 85%, 80%, 75%, 70%, 65%, 60%, 55%, 50%, 45%, 40%, 35%, 30%, 25%, 20%, 15%, 10%, 5%, or 1% of the summed effect (B+C). It is understood that these numbers can be averages, with variances, and that these types of statistics can be employed, as discussed herein, to determine if the combined effect is less than the summed effect.

It is also understood that when the combined effect A, is less than the summed effect (B+C) that this can be expressed as a ratio of A/(B+C) and that ratios less than 1 indicate compositions that inhibit the ORN effect. For example, disclosed are compositions that have a ratio of less than or equal to 0.01, 0.03, 0.05, 0.07, 0.08, 0.09, 0.1, 0.2, 0.3, 0.4, 0.5, 0.52, 0.55, 0.6, 0.64, 0.65, 0.69, 0.7, 0.72, 0.75, 0.80, 0.83, 0.85, 0.87 0.90, 0.92, 0.95, 0.97, or 0.99. The ratio can be expressed in terms of a range of these individual ratios, such as 0.72 to 0.92, for example, or 0.52 to 0.64, or 0.69 to 0.83.

Thus, when an ORN is expressing the P2Y receptor and a P2Y selective agonist or a non-selective purinergic agonist is applied, odor response is suppressed. Likewise, when an ORN is expressing a P2X receptor and a P2X selective agonist is applied, the odor response is typically suppressed. Also, when both P2X and P2Y receptors are present on an ORN, and either a P2Y selective agonist, a P2X selective agonist, or a nonselective agonist is applied, the odor response is suppressed. Combinations of selective and non-selective agonists can be applied, and P2X and P2Y receptors can be suppressed depending on the combination of agonists in the mixture.

Disclosed are P2X selective agonists and P2Y selective agonists. Disclosed are P2X directed agonists and P2Y directed agonists. In certain embodiments, a P2X directed agonist is any agonist that has a greater effect on a P2X receptor than on a P2Y receptor. Likewise, in certain embodiments, a P2Y directed agonist is any agonist that has a greater effect on a P2Y receptor than on a P2X receptor. In other embodiments, P2X agonists and P2Y agonists can be determined by comparing the activity to known selective agonists, such as those discussed herein. It is understood that the level of activity of each selective agonist discussed herein, is disclosed. Also disclosed are P2 agonists that interact with any P2 receptor. It is understood that many P2X and P2Y agonists can be both a selective agonist as well as a directed agonist. For example, UTP can be a selective and a directed P2Y agonist.

Just as P2X and P2Y agonists inhibit ORN response to odor stimulants, so too, antagonists of P2X and P2Y receptors can lead to an enhancement of the smell response. P2X antagonists, such as those disclosed in Table 4, for example, act at P2X receptors and P2Y antagonists, such as those disclosed in Table 4, for example, act at P2Y receptors, and thus can be stimulators of odor responsiveness. It is understood that the assays, measurements, and functional limitations, as discussed, herein for agonists are applicable for antagonists as well. Thus, for example, antagonists can be assayed in a calcium flux assay, but an antagonist would be considered a composition (B) that does not evoke a response in the calcium flux assay alone, i.e., B=0. However, when a composition (B) is co-applied with an odor (C), the combined odor and composition effect (A), would be greater than the effect of odor alone (C), or composition alone (B) and thus, A>(B+C) or since B=0, A>C.

Typically, antagonists have an opposite effect on a receptor than an agonist, and application of the disclosed methods and limitations can be thus applied to antagonists, as they were for agonists.

Disclosed are P2X selective antagonists and P2Y selective antagonists. Disclosed are P2X directed antagonists and P2Y directed antagonists. In certain embodiments, a P2X directed antagonist is any antagonist that has a greater effect on a P2X receptor than on a P2Y receptor. Likewise, in certain embodiments, a P2Y directed antagonist is any antagonist that has a greater effect on a P2Y receptor than on a P2X receptor. In other embodiments, P2X antagonist and P2Y antagonist can be determined by comparing the activity to known selective antagonists, such as those discussed herein. It is understood that the level of activity of each selective antagonist discussed herein, is disclosed. Also disclosed are P2 antagonists that interact with any P2 receptor. It is understood that many P2X and P2Y antagonists can be both a selective antagonist as well as a directed antagonists.

Disclosed herein are methods of modulating odor sensitivity in a subject, comprising administering a composition to the subject, wherein the composition is an antagonist of a P2X or P2Y purinergic receptor. The antagonist can increase the odor sensitivity of the subject, which can be desirable to those with olfactory impairments. Increasing odor sensitivity is also desirable in conjunction with a pleasant smell. The antagonist can reduce basal $Ca^{2+}$ levels in olfactory receptor neurons which will make the neurons more excitable during subsequent odor stimulation thereby increasing the odor sensitivity of the subject. The antagonist can increase the ratio of observed coapplication-evoked calcium transient compared to the individual odor peak amplitudes in a cell activation assay, as discussed above.

C. Compositinons

1. ATP and ATP Analogs

The structure of ATP is shown in Formula 1.

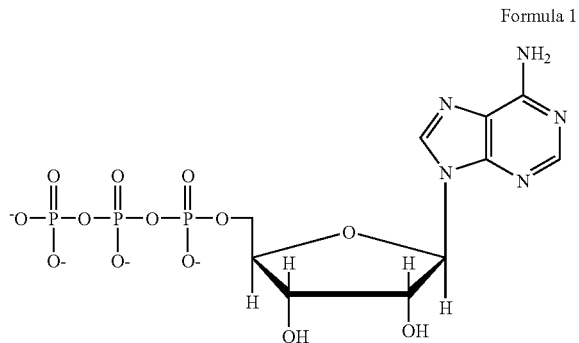

Formula 1

There are many analogs of ATP that can be made. For example, analogs can be made at the base moiety, the sugar moiety, and the phosphate moiety, as discussed herein. The base moiety can be considered as adenin-9-yl (A). Many modifications can take place at this moiety. The sugar moiety of a nucleotide is typically a ribose or a deoxyribose. The phosphate moiety of a nucleotide is typically pentavalent phosphate. A non-limiting example of a nucleotide would be 3'-AMP (3'-adenosine monophosphate), ADP, and ATP.

ATP analogs can have modifications to the base moiety which would include natural and synthetic modifications of A, such as hypoxanthin-9-yl (I), and 2-aminoadenin-9-yl, 2-aminoadenine, xanthine, 6-methyl and other alkyl derivatives of adenine, 2-propyl and other alkyl derivatives of adenine, 8-halo, 8-amino, 8-thiol, 8-thioalkyl, 8-hydroxyl and other 8-substituted adenines, 7-methyladenine, 8-azaadenine, 7-deazaadenine and 3-deazaadenine, and O-6 substituted adenines, including 2-aminopropyladenine.

ATP analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. 2' sugar modifications also include but are not limited to $-O[(CH_2)_nO]_mCH_3$, $-O(CH_2)_nOCH_3$, $-O(CH_2)_nNH_2$, $-O(CH_2).CH_3$, $-O(CH_2)_n-ONH_2$, and $-O(CH_2)_nON[(CH_2)_nCH_3)]_2$, where n and m are from 1 to about 10.

ATP analogs can have other modifications at the 2' position and include but are not limited to: C, to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, and polyalkylamino. Modified sugars would also include those that contain modifications at the bridging ring oxygen, such as $CH_2$ and S. Nucleotide sugar analogs can also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

ATP analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates.

It is understood that nucleotide analogs need only contain a single modification, but can also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Disclosed are uses for non-selective, P2X selective and P2Y selective ATP analogs. Furthermore, there are ATP selective agonists and ATP selective antagonists. For example, non-selective purinergic receptor agonists are ATP, ATPγS, and AMP (Table 4). For example, P2Y-'selective' agonists are UTP, ADP, and MeS-ADP (Table 4). In addition, an example of a P2X-'selective' agonist is βγ-methylene ATP (Table 4). Suramin and pyridoxalphosphate-6-azophenyl-2',4'-disulfonic acid (PPADS) are examples of non-specific antagonists.

2. General Composition Information a) Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

For example, SEQ ID NO:1 represents a version of a P2X receptor. All fragments of the P2X receptor, as well as the other proteins, such as receptors discussed herein, are considered disclosed.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Scienice 244:48-52, 1989, Jaeger et al. Proc. Natl. cad. Sci. USA 86:7706-7710, 1989, Jaeger et al. Methods Enzymol. 183:281-306, (1989) which are herein incorporated by reference for at least material related to nucleic acid alignment. It is understood that any of the methods typically can be used and that in certain instances the results of these various methods can differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80'percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

b) Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization can involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $K_d$, or where only one of the nucleic acid molecules is 10 fold or 100 fold or 1000 fold or where one or both nucleic acid molecules are above their $K_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those indicated by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions can provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

c) Nucleic Acids

There are a variety of molecules disclosed herein that are nucleic acid based, including for example the nucleic acids that encode, for example the purinergic receptors, as well as various functional nucleic acids. The disclosed nucleic acids are made up of, for example, nucleotides, nucleotide analogs, or nucleotide substitutes. Non-limiting examples of these and other molecules are discussed herein. It is understood that for example, when a vector is expressed in a cell that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

(1) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

A nucleotide analog is a nucleotide, which contains some type of modification to the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

(2) Nucleotide Analogs and Related Molecules

A nucleotide analog is a nucleotide, which contains some type of modification to the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$, alkyl or $C_2$ to $C_{10}$ alkenyl and alkynyl. 2' sugar modifications also include but are not limited to —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON [(CH$_2$)$_n$CH$_3$)]$_2$, where n and m are from 1 to about 10.

Other modifications at the 2' position include but are not limited to: C, to $C_{10}$ lower alkyl, substituted lower allyl, alkaryl, aralkyl, O-alkaryl or O-aralkyl, SH, SCH$_3$, OCN, Cl, Br, CN, CF, OCF$_3$, SOCH$_3$, SO$_2$CH$_3$, ONO$_2$, NO$_2$, N$_3$, NH$_2$, heterocyloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications can also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs can also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but can also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones, formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine)(PNA). U.S. Pat. Nos. 5,539,082; 5,714,331; and 5,719,262 teach how to make and use PNA molecules, each of which is herein incorporated by reference. (See also Nielsen et al., Science, 1991, 254, 1497-1500).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Ianoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937. Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

(3) Sequences

There are a variety of sequences related to the purinergic receptors having the following Genbank Accession Numbers and these sequences and others are herein incorporated by reference in their entireties as well as for individual subsequences contained therein.

There are many sequences of the PX2 receptor, some of which can be found for example herein and others which can be found at Genbank all of which are herein incorporated by reference. It is understood that the description related to this sequence is applicable to any sequence related to purinergic receptors, for example, unless specifically indicated otherwise. Those of skill in the art understand how to resolve sequence discrepancies and differences and to adjust the compositions and methods relating to a particular sequence to other related sequences. Primers and/or probes can be designed for any of the purinergic receptor sequences given the information disclosed herein and known in the art.

(4) Primers and Probes

Disclosed are compositions including primers and probes, which are capable of interacting with the purinergic receptors as disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with a purinergic receptor nucleic acid or region of the purinergic receptor nucleic acid or they hybridize with the complement of the purinergic receptor nucleic acid or complement of a region of the purinergic receptor nucleic acid.

d) Delivery of the Compositions to Cells

(1) Nucleic Acid Delivery

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

In the methods described herein, which include the administration and uptake of exogenous DNA into the cells of a subject (i.e., gene transduction or transfection), the disclosed nucleic acids can be in the form of naked DNA or RNA, or the nucleic acids can be in a vector for delivering the nucleic acids to the cells, whereby the encoding DNA or DNA or fragment is under the transcriptional regulation of a promoter, as would be well understood by one of ordinary skill in the art as well as enhancers. The vector can be a commercially available preparation, such as an adenovirus vector (Quantum Biotechnologies, Inc. (Laval, Quebec, Canada).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). The disclosed compositions and methods can be used in conjunction with any of these or other commonly used gene transfer methods.

As one example, if the antibody-encoding nucleic acid or some other nucleic acid encoding a puringergic receptor interactions is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six-month intervals (or other appropriate time intervals, as determined by the skilled practitioner) for an indefinite period and/or until the efficacy of the treatment has been established.

Parenteral administration of the nucleic acid or vector, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

(2) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed compositions or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer* 60:275-281, (1989); Bagshawe, et al., *Br. J. Cancer;* 58:700-703, (1988); Senter, et al., *Bioconjugate Chem.* 4:3-9, (1993); Battelli, et al., *Cancer Immunol. Immunother.*, 35:421-425, (1992); Pietersz and McKenzie, *Immunolog. Reviews.* 129: 57-80, (1992); and Roffler, et al., *Biochem. Pharmacol*, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in viva. The following references are examples of the use of this technology to target specific proteins to tumor tissue (Hughes et al., *Cancer Research*, 49:6214-6220, (1989); and Litzinger and Huang, *Biochimica et Biophysica Acta* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, *DNA and Cell Biology* 10:6, 399-409 (1991)).

(3) In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

e) Expression Systems

The nucleic acids that are delivered to cells typically contain expression-controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

(1) Viral Promoters and Enhancers

Preferred promoters controlling transcription from vectors in mammalian host cells can be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature*, 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3:1108 (1983)) to the transcription unit. Furthermore, enhancers can be within an intron (Baneiji, J. L. et al., *Cell* 33:729 (1983)) as well as within the coding sequence itself (Osborne, T. F., et al., *Mol. Cell Bio.* 4:1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer can be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer regions can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA.

The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

(2) Markers

The vectors can include nucleic acid sequence encoding a marker product. This marker product is used to determine if the gene has been delivered to the cell and once delivered is being expressed. Preferred marker genes are the E. coli lacZ gene, which encodes β-galactosidase, and green fluorescent protein.

In some embodiments the marker can be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1:327 (1982)), mycophenolic acid, (Mulligan, R. C. and Berg, P. *Science* 209:1422 (1980)) or hygromycin, (Sugden, B. et al., *Mol. Cell. Biol.* 5:410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

1) Peptides

(1) Protein Variants

As discussed herein there are numerous variants of the purinergic receptor proteins and that are known and herein contemplated. In addition, to the known functional purinergic receptor species variants there are derivatives of the purinergic receptor proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site-specific mutagenesis of nucleotides in the DNA encoding the protein, thereby producing DNA encoding the variant, and thereafter expressing the DNA in recombinant cell culture.

Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues.

Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 5 and 6 and are referred to as conservative substitutions.

TABLE 5

| Amino Acid Abbreviations | |
|---|---|
| Amino Acid | Abbreviations |
| Alanine | AlaA |
| Allosoleucine | AiIe |
| Arginine | ArgR |
| Asparagines | AsnN |
| Aspartic acid | AspD |
| Cysteine | CysC |
| Glutamic acid | GluE |
| Glutamine | GlnQ |
| Glycine | GlyG |
| Histidine | HisH |
| Isolelucine | IleI |

TABLE 5-continued

Amino Acid Abbreviations

| Amino Acid | Abbreviations |
| --- | --- |
| Leucine | Leu L |
| Lysine | Lys K |
| Phenylalanine | Phe F |
| Proline | Pro P |
| Pyroglutamic acid | Glu |
| Serine | Ser S |
| Threonine | Thr T |
| Tyrosine | Tyr Y |
| Tryptophan | Trp W |
| Valine | Val V |

TABLE 6

Original Residue Exemplary Conservative Substitutions, others are known in the art.

| | |
| --- | --- |
| Ala | ser |
| Arg | lys, gln |
| Asn | gln; his |
| Asp | glu |
| Cys | ser |
| Gln | asn, lys |
| Glu | asp |
| Gly | ala |
| His | asn; gln |
| Ile | leu; val |
| Leu | ile; val |
| Lys | arg; gln; |
| Met | Leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 6, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also can be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T.E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO:1 sets forth a particular sequence of a P2X receptor. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence cannot be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein in the particular organism from which that protein arises is also known and herein disclosed and described.

g) Pharmaceutical Carriers/Delivery of Pharmaceutical Products

As described herein, the compositions, such as the ATP and ATP analogs, can also be administered in vivo in a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions can be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the composition. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews* 129:57-80, (1992); and Roffler, et al., *Biochem Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in viva. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, *DNA and Cell Biology* 10:6, 399-409 (1991)).

(1) Pharmaceutically Acceptable Carriers

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface-active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration include powders or granules, suspensions or solutions in water or non-aqueous media, capsules, sachets, or tablets. Thickeners, flavorings, diluents, emulsifiers, dispersing aids or binders can be desirable.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

(2) Therapeutic Uses

Effective dosages and schedules for administering the compositions can be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations hourly or daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the ATP or ATP analogs used alone might range from about 1 µg/kg to up to 100 mg/kg of body weight or more per day, depending on the factors mentioned above. For example, based on the similarities of $EC_{50}$ concentrations for P2 receptors across many species an effective dose to modulate smell in a human would be similar to our mouse model, i.e., 10-200 µm.

Following administration of a disclosed composition, such as an ATP analog, for the modulation of smell, the efficacy of the therapeutic composition can be assessed in various ways well known to the skilled practitioner. For instance, one of ordinary skill in the art will understand that the compositions disclosed herein are efficacious in modulating, such as enhancing or reducing the sensation of smell in a subject, by observing that the composition reduces or enhances the sensation of smell to a particular or general odor stimulant. Smell sensation can be measured by methods that are known in the art, for example, and in vitro methods using an ORN calcium imaging assay as discussed herein, can also be used.

The compositions that modulate smell disclosed herein can be administered prophylactically to patients or subjects who are at risk for being exposed to severe or damaging odor stimulation or who have a desire to have either an increased or decreased sensitivity to an odor. For example, elderly people can increase sensitivity to odor to compensate for loss during aging. Conversely, those on chemotherapy drugs may need decreased odor sensitivity to reduce nausea.

Other molecules that modulate odor sensitivity, but do not have a particular pharmaceutical function can be used for tracking changes within ORNs.

h) Computer Readable Mediums

It is understood that the disclosed nucleic acids and proteins and compositions can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences and ATP or ATP analogs on computer readable mediums, such as, commercially available floppy disks, tapes, chips, hard drives, compact disks, and videodisks, or other computer readable mediums. Also disclosed are the binary code representations of the disclosed sequences and ATP or ATP analogs. Those of skill in the art understand what computer readable mediums. Thus, computer readable mediums on which the nucleic acids or protein sequences are recorded, stored, or saved i) Chips and Micro Arrays Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein. Disclosed are chips where at least one address is the composition, such as an ATP analog, disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

j) Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include an ATP analog in a formulation for delivery to an ORN. For example, disclosed is a kit for modulating odor sensitivity comprising ATP in a formulation for delivery to an ORN.

D. Methods of Making the Compositions

The compositions disclosed herein and the compositions necessary to perform the disclosed methods can be made using any method known to those of skill in the art for that particular reagent or compound unless otherwise specifically noted.

1. ATP Analog Generation

The disclosed ATP analogs can be made using a variety of synthetic procedures. Often the analogs can be purchased. For example, the following analogs can be purchased from Sigma Inc., 2-(Methylthio)adenosine 5'-triphosphate, 2-Chloroadenosine 5' triphosphate, 2',5'-Dideoxyadenosine 3'-triphosphate, 2'-3'-O-(4-Benzoylbenzoyl)adenosine 5'-triphosphate, 2'-Monophosphoadenosine 5'-diphosphoribose, ATP-Ribose, 8-Bromoadenosine 5'-triphosphate, Adenosine 5'-triphosphate P3-[1-(2-nitrophenyl)ethyl ester] (Caged ATP'NPE caged ATP), Adenosine 5'-triphosphate, Adenosine 5'-($\beta$,$\gamma$-imido)triphosphate, Adenosine 5'-[$\gamma$-thio] triphosphate, Adenosine 5'-triphosphate g-(1-[2-nitrophenyl] ethyl) ester (Caged ATP), 125229-58-5 minimum 95%, and 2',3'-O-(2,4,6-Trinitrophenyl)adenosine 5'-triphosphate. It is understood that these compositions and others come as salts, such as lithium, or sodium salts, as well as, for example, triethylammonium salts, and that they can also be formulated in appropriate pharmaceutical salts.

2. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

E. Methods of Using the Compositions

1. Methods of Using the Compositions as Research Tools

The disclosed compositions can be used in a variety of ways as research tools. For example, the disclosed compositions, such as ATP and analogs, can be used to study the signal transduction pathways related to olfactory signaling.

The disclosed compositions can be used as discussed herein as either reagents in micro arrays or as reagents to probe or analyze existing microarrays. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

a) Screening Assays

Provided are methods of screening for an agonist or an antagonist of purinergic receptor of the olfactory system, comprising contacting a purinergic receptor with a test compound; detecting intracellular calcium levels; and screening for a change in calcium levels as compared to a control level, a change indicating the compound is an agonist or an antagonist of the olfactory system.

Screening optionally takes place in multi-well plates. Multi-well plates are standard in the art and come in a variety of sizes and shapes. For example, the multi-well plate can be 24, 48, or 96 well plates. Such screening assays can be automated or further modified for high throughput analysis. For high throughput screening, each well can include numerous test components. If a positive reaction is detected in a well, the screening is repeated with one of the test compounds contained in a single well.

An "elevation in calcium" is defined as an increase in calcium levels greater than 1 nM above basal levels. The change in calcium levels can be between 5 nM and 10 nM, for example. The elevation in calcium can also be greater than 100 nM above basal levels. A "transient reduction in calcium" is defined as decrease in calcium levels greater than 1 nM below basal levels. The reduction in calcium can also be greater than 100 nM below basal levels.

The time defined as "transient" means not permanent. Thus, transient can be less than 10 seconds, less than 30 seconds, less than 1 minute, less than 5 minutes, less than 10 minutes, or less than 20 minutes, for example.

The term "sustained" means that the effect continues for a period of time. For example, sustained can be greater than 1 minute, greater than 5 minutes, greater than 10 minutes, greater than an hour, greater than 24 hours, or greater than 1 year.

Also disclosed is a method of screening for an agonist or an antagonist of a purinergic receptor of the olfactory system, comprising contacting a first purinergic receptor expressing cell with a set of test compounds; detecting calcium levels in the first purinergic receptor cell; and selecting each compound in the set that contacted the first purinergic receptor cell, wherein the first purinergic receptor cell showed a transient change in calcium as compared to a control level, indicating the compound is an agonist or an antagonist of a purinergic receptor of the olfactory system. The method can further comprise the steps of contacting a second purinergic receptor cell with one test compound selected above, and detecting calcium levels in the second purinergic receptor cell, wherein a transient change in calcium as compared to a control level indicates the compound is an agonist or an antagonist of a purinergic receptor of the olfactory system.

Also disclosed is a method of screening for an agonist or an antagonist of a purinergic receptor of the olfactory system, comprising contacting a test compound with a cell that expresses a heterologous nucleic acid that encodes a purinergic receptor; and detecting calcium levels in the cell; a transient change in calcium as compared to a control level, indicating an agonist or an antagonist of a purinergic receptor of the olfactory system.

Also contemplated are agents identified by the screening methods described herein, as well as methods of making those agents. An example of a method of making an agent includes identifying the agent using the methods provided herein, and manufacturing the agent or manufacturing the agent in a pharmaceutically acceptable carrier.

Preferably, the cell is a cell that lacks the receptor prior to introduction of the heterologous nucleic acid. The cell can be transiently transfected with the heterologous nucleic acid or a stable cell line containing the expressed receptor can be made using standard techniques in the art. By "heterologous nucleic acid" is meant that any heterologous or exogenous nucleic acid can be inserted into a vector for transfer into a cell, tissue or organism. The nucleic acid can encode a polypeptide or protein or an antisense RNA, for example. The nucleic acid can be functionally linked to a promoter. By "functionally linked" is meant such that the promoter can promote expression of the heterologous nucleic acid, as is known in the art, such as appropriate orientation of the promoter relative to the heterologous nucleic acid. Furthermore, the heterologous nucleic acid preferably has all appropriate sequences for expression of the nucleic acid, as known in the art, to functionally encode, i.e., allow the nucleic acid to be expressed. The nucleic acid can include, for example, expression control sequences, such as an enhancer, and necessary information processing sites, such as ribosome binding sites, RNA splice sites, polyadenylation sites, and transcriptional terminator sequences.

Calcium levels and changes in calcium levels can be detected using a calcium indicator such as the cell-permeable methyl ester form of Fura-2, which is Fura-2/AM. In another example, a fluorescence plate reader is used that detects a single wavelength, such as $Ca^{2+}$ indicator dyes Fluo 3, Fluo 4 AM, Quin 2, Indo-1 and Indo-4.

Optionally, the compound being screened can augment the effects of other compounds such as ATP, for example. In this case, the compound being screened can be tested in the presence of another compound that stimulates the purinergic receptor. For example, the purinergic receptor expressing cell can be in a solution containing an effective amount of ATP. An "effective amount of ATP" is defined as about 300 nM to about 1 mM of ATP.

F. EXAMPLES

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Figure 1D:
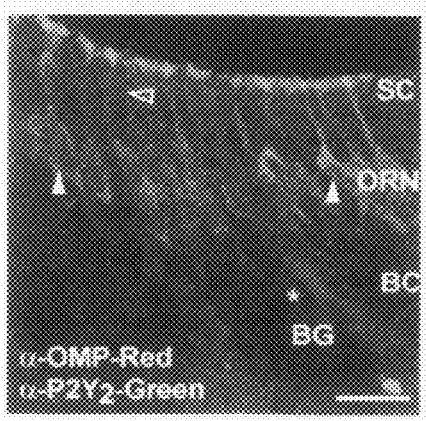
Figure 1E:
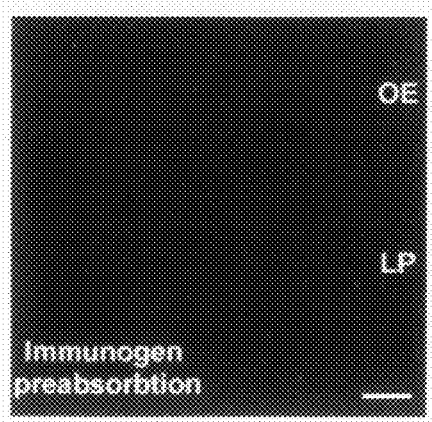

ATP Differentially Modulates Odor Responsiveness through Purinergic Receptor Activation: Activation of Purinergic Receptor Subtypes Differentially Modulates Odor Sensitivity a) Results (1) Localization of Purinergic Receptors in the Peripheral Olfactory System Using RT-PCR and immunohistochemical methods ionotropic $P2X_2$ and G-protein-coupled $P2Y_2$ receptor expression were found in both olfactory epithelium and olfactory bulb. RT-PCR analysis revealed mRNA expression for the $P2Y_2$ receptor and two isoforms of the $P2X_2$ receptor; $P2X_{2-1}$ (Brake, A. J., et al., Nature 371, 519-523 (1994)) and $P2X_{2-2}$ (Brandle et al., 1997)(FIG. 1A). To identify the cell type and subcellular distribution of purinergic receptors in olfactory epithelium and olfactory bulb, antibodies against $P2X_1$, $P2X_2$, $P2X_4$ and $P2Y_2$ receptors, and olfactory marker protein (OMP), which is found in mature olfactory receptor neurons (ORNs) were used. OMP-positive ORNs showed punctate immunoreactivity (IR) to $P2X_1$ and $P2X_4$ antibodies on cell somas and axons (FIGS. 1B, C) and $P2Y_2$-IR on the dendrites, somas and axons (FIG. 1D). Both P2X- and P2Y-IR was absent from dendritic knobs and cilia of ORNs. OMP-negative ORNs and basal cells (olfactory stem cells) showed P2X- and P2Y-IR. Sustentacular cells and Bowman's glands showed only P2Y2-IR (FIG. 1D). In the olfactory bulb, there was $P2X_1$, $P2X_2$, $P2X_4$ and $P2Y_2$ receptor IR in the olfactory nerve layer, the glomerular layer and the mitral cell layer. There was no $P2X_2$-IR in the olfactory neuroepithelium; however, there was punctate $P2X_2$-IR on blood vessels just below the basal cells. Thus, the underlying blood vessels are the likely source of $P2X_2$ mRNA identified by the RT-PCR studies of the olfactory epithelium. Preabsorption of the primary antibody with peptide antigen (FIG. 1E) or omission of the primary antibody blocked the purinergic receptor staining. Identification of regionally localized purinergic receptors in mammalian olfactory epithelium is consistent with extracellular ATP playing multiple roles in the peripheral olfactory system.

(2) Purinergic Receptors are Functional in Cultured Olfactory Receptor Neurons

Figure 2A:
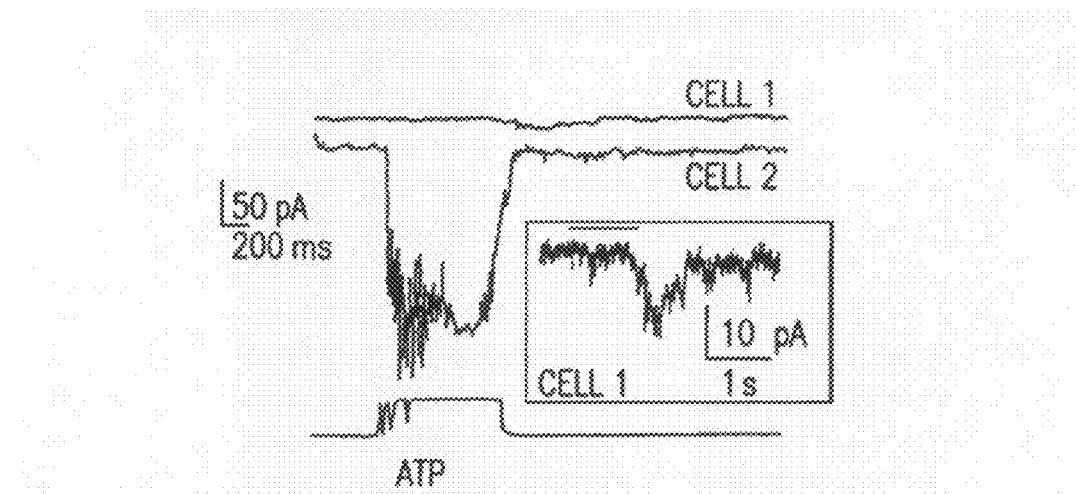

The physiological activation of purinergic receptors in cultured mouse ORNs (Vargas and Lucero, 1999a) were examined using both electrophysiology (Danaceau and Lucero, 1998)(FIG. 2A), and calcium imaging (FIG. 2B-E). ATP (10 μM) evoked inward currents in 39% (27/69 ORNs) of the perforated-patched mouse ORNs during brief (1-10 s) applications (FIG. 2A). Some cells exhibited a distinct, long latent period consistent with slowly activating G-protein coupled P2Y receptors (cell 1, FIG. 2A inset)(13/27 cells; latency=1140±236 ms; $I_{max}$=−29±8 pA). Rapid activation of inward current that closely followed the ATP stimulus profile with little or no desensitization was also observed, indicating involvement of non-desensitizing ionotropic P2X receptors [P2X4 and/or $P2X_7$] (Ralevic and Burnstock, 1998)(FIG. 2A, cell 2) (14/27 cells; latency=81±15 ms, $I_{max}$=−235±74 pA). These electrophysiological results support the immunohistochemical evidence of expression of both purinergic receptor subtypes in ORNs.

Figure 2B:
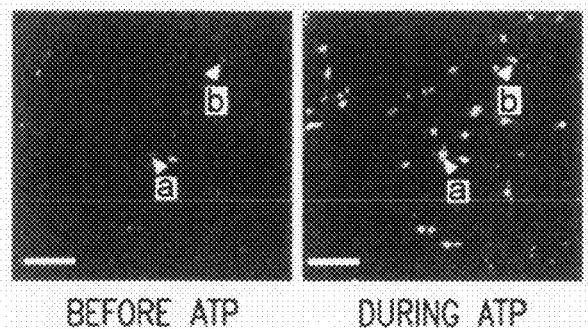
Figure 2C:
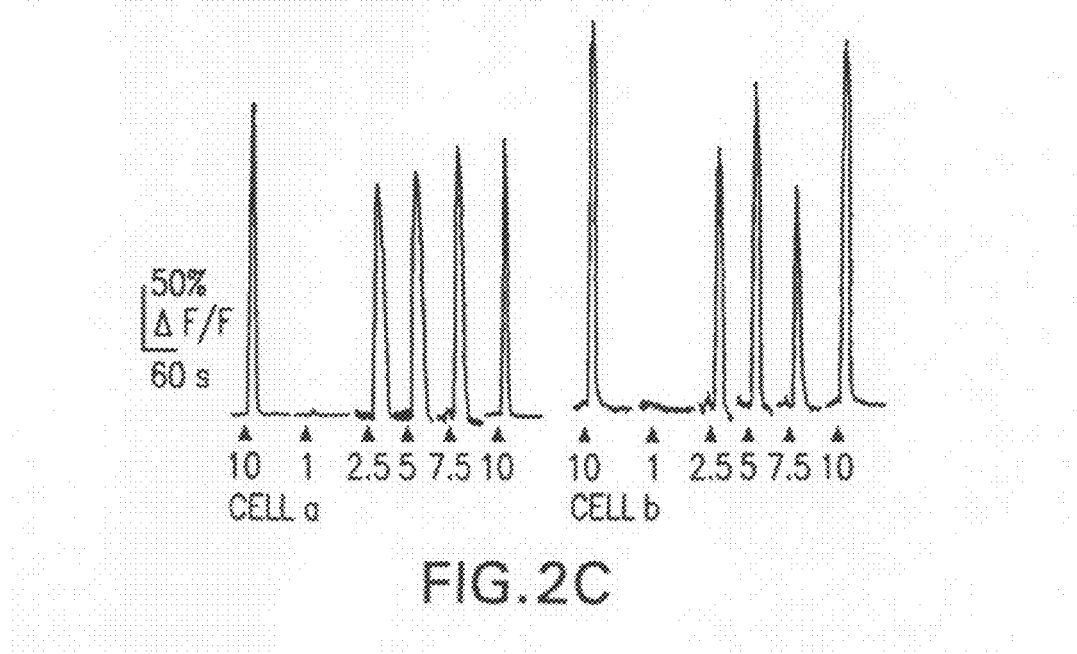
Figure 2D:
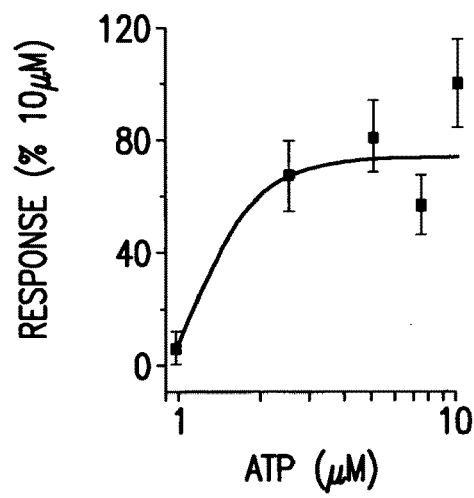
Figure 2E:
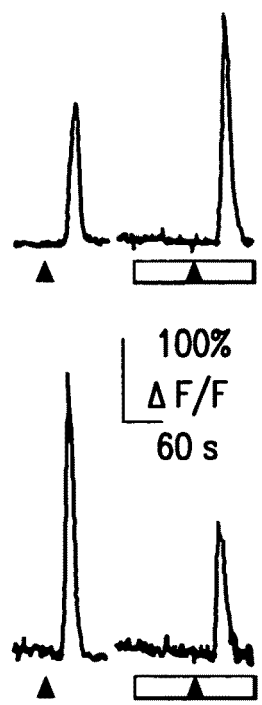

Extracellularly applied ATP evoked a rapid transient increase in $[Ca^{2+}]_i$ (FIGS. 2B, C; 76/84 ORNs). On average, ATP (10 μM) induced a 151±12% A fluorescence (F)/F increase in $[Ca^{2+}]_i$ (n=76; range 13-398%). Averaged dose-response relations for ATP-induced $[Ca^{2+}]_i$ increases in cultured mouse ORNs gave half-maximally effective concentrations ($EC_{50}$) of 1.6 μM (n=58), comparable to previous reports for brain P2X receptors (FIG. 2D)(North and Barnard, 1997; North and Surprenant, 2000; Ralevic and Burnstock, 1998). In the absence of external $Ca^{2+}$, the ATP-induced rise in $[Ca^{2+}]_i$ was 31±11% larger than calcium transients in the presence of $Ca^{2+}$, although in a few ORNs (3/19), the ATP-evoked increases were smaller, but never absent, in $Ca^{2+}$-free solution (FIG. 2E). The increase in fluorescence intensity in the absence of $Ca^{2+}$ indicates that (1) part of the signal results from release from intracellular $Ca^{2+}$ stores, implicating P2Y receptor activation, and (2) $Ca^{2+}$ can reduce the concentration of free ATP or modulate the purinergic receptor (Honore et al., 1989; North and Surprenant, 2000). Thus, electrophysiology and $Ca^{2+}$ imaging show that purinergic receptors are functional in primary cultures of mouse ORNs.

(3) Confocal Imaging of Olfactory Epithelium Slices

To study the effects of ATP on odor responses, acutely prepared slices of mouse olfactory epithelium were used.

Confocal imaging of fluo-4 AM-loaded olfactory epithelium slices allows simultaneous recording from identified structures within the olfactory epithelium, i.e., both ORNs and sustentacular cells. Reproducible odor-evoked calcium transients were obtained when imaging ORNs >100 µM below the surface of the slice (FIGS. 3A1-A5). Odor-evoked calcium transients rapidly activated and returned to basal levels within 125.7±11.1 s (FIG. 3A, n=11 ORNs). Superfusion of ATP (10 µM) onto this slice evoked calcium transients from all 11 ORNs previously identified by their response to odors, although the responses to ATP (FIGS. B1-B4) are less obvious than the odor responses (FIG. 3B2). The difference in robustness can be due to poor access to the ATP stimulus: odorant receptors are on the cilia of the ORNs, which extend beyond the outer edge of the olfactory epithelium, whereas purinergic receptors are located deeper within the olfactory epithelium. ATP also evoked calcium transients from sustentacular cells, identified by their location, morphology, and lack of response to odor (FIG. 3B3). The latency of activation for the ATP-evoked calcium transient was shorter in the ORN (FIG. 3B2, solid up arrowhead) than in sustentacular cells (FIG. 3B3, open down arrowhead). Collectively, this was consistent with ORNs expressing the faster P2X receptors, and the sustentacular cells expressing the slower G-protein coupled P2Y receptors.

To further test whether functional purinergic receptor subtypes are differentially expressed in olfactory epithelium cell types, purinergic receptor agonists were used. As there are no completely specific purinergic receptor agonists (Ralevic and Burnstock, 1998), the selectivity was determined as discussed herein. The P2X 'selective' agonist βγ-methylene ATP was superfused onto the slice (FIG. 3C). Only the ORNs, and not the sustentacular cells, responded to βγ-methylene ATP with an increase in $[Ca^{2+}]_i$ (FIG. 3C5). The P2Y 'selective' agonist UTP evoked calcium transients in both ORNs and sustentacular cells (FIG. 3D). However, compared to the non-selective agonist ATP, the peak amplitudes were smaller in the ORNs and the latency of activation in the ORNs was longer and equivalent to the latency of activation in the sustentacular cells (compare FIGS. 3D2,5 to B2,5). These data indicated that the ORN expressed P2X and, to a lesser extent, P2Y receptors, and that the sustentacular cells expressed only P2Y receptors. It further confirms the immunohistochemical and electrophysiological evidence for differential expression of purinergic receptors in mammalian olfactory epithelium.

A variety of non-selective purinergic receptor agonists (ATP, ATPγS, AMP), P2Y-'selective' agonists (UTP, ADP, MeS-ADP), P2X-'selective' agonists (βγ-methylene ATP) (FIGS. 4A, B), and an adenosine receptor 'selective' agonist (adenosine) were superfused onto olfactory epithelial slices and the change in $[Ca^{2+}]_i$ was measured. Adenosine- or AMP-evoked calcium transients were never observed. ORNs responded with approximately equal frequency to P2Y and P2X receptor agonists whereas sustentacular cells responded primarily to P2Y receptor agonists. The general non-specific purinergic receptor antagonists Suramin and pyridoxalphosphate-6-azophenyl-2',4'-disulfonic acid (PPADS) were used to further confirm that purinergic-evoked calcium transients were mediated via purinergic receptors. In ORNs previously shown to respond to both ATP and UTP, Suramin (100 µM) reversibly blocked both ATP- and UTP-evoked calcium transients by 88±2 and 72±6% (n=9). PPADS (25 µm) also reversibly blocked the ATP- and UTP-evoked calcium transients by 87±5 and 92±3% (n=5). Purinergic receptor antagonists also reversibly blocked purinergic nucleotide-evoked calcium transients in sustentacular cells. Suramin blocked ATP- and UTP-evoked $Ca^{2+}$ transients by 90±1 and 89±1% (n=37) and PPADS blocked the transients by 82±2 and 76±2%, respectively (n=30). Collectively, the data show that the ATP-evoked calcium transients were mediated by P2X and P2Y receptors.

(4) ATP Modulates Odor Responses

Calcium is an important intracellular messenger during odor transduction affecting signal amplification (Lowe and Gold, 1993) and adaptation (Zufall et al., 1991). The data indicate that purinergic nucleotides evoke robust increases in intracellular calcium. Odors were sequentially superfused, ATP and the combination of odors and ATP onto olfactory epithelium slice preparation. It was found that ATP could (1) have no effect, (2) cause suppression (FIG. 5A), where the calcium transient evoked by co-application is less than the sum of the calcium transients evoked by the individual components, or (3) cause enhancement (FIG. 5B), in which the calcium transient due to co-application is larger than the sum of the individual components.

The increases in $Ca^{2+}$ elicited from co-application of ATP and odor from two cells (FIGS. 5A, B) have been expressed as a proportion of the sum of the individual responses (FIG. 5C). Of the cells that responded to odor, 62% exhibited a significant decrease in the summed $[Ca^{2+}]_i$ increase (mean suppression=57±5%; paired t-test, p=0.01, n=26). The observed decrease due to co-application was not the result of run-down because post-co-application responses both to ATP and to odors were +10% of pre-co-application (FIG. 5A). Of the odor-responsive ORNs, only two exhibited a >20% increase in evoked $[Ca^{2+}]_i$ increase (mean enhancement=157±34%), indicating a combined effect. Thus, ATP significantly reduced odor-induced calcium responses in the majority of ORNs.

(5) Activation Of Purinergic Receptor Subtypes Modulates Odor Sensitivity

Figure 6A:
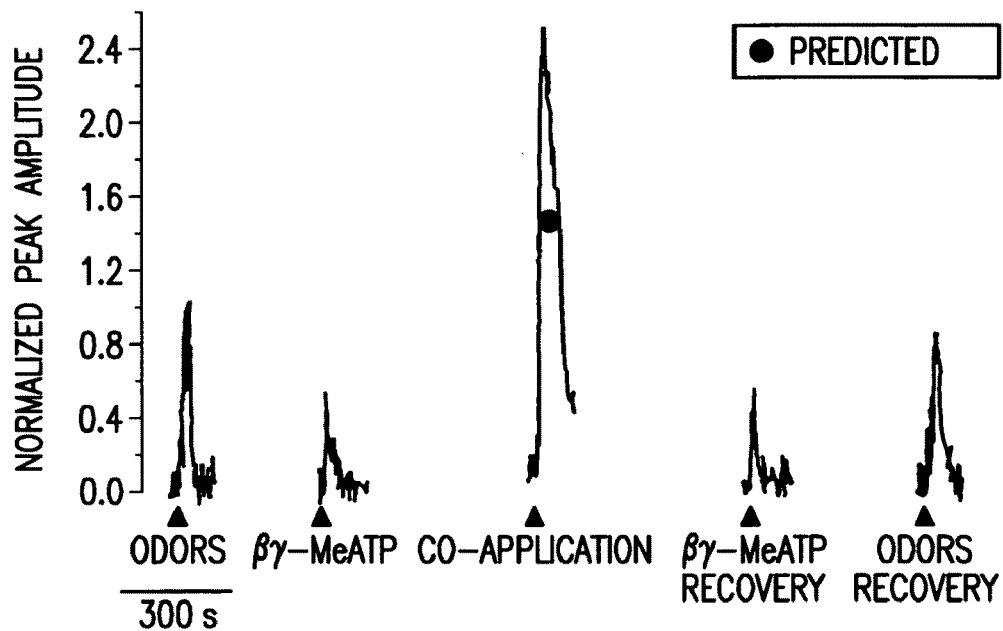
Figure 6B:
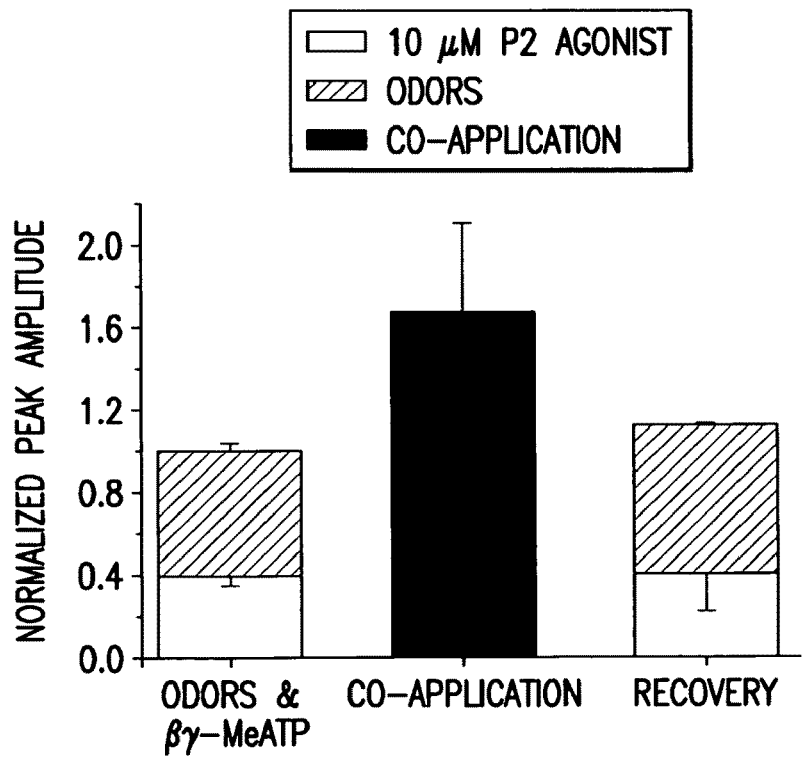
Figure 6C:
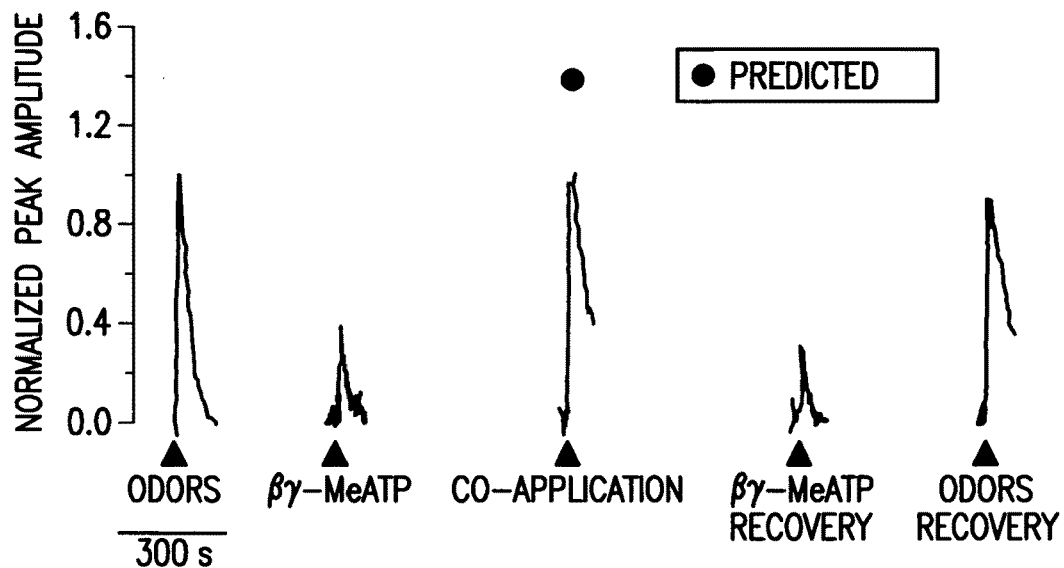
Figure 6D:
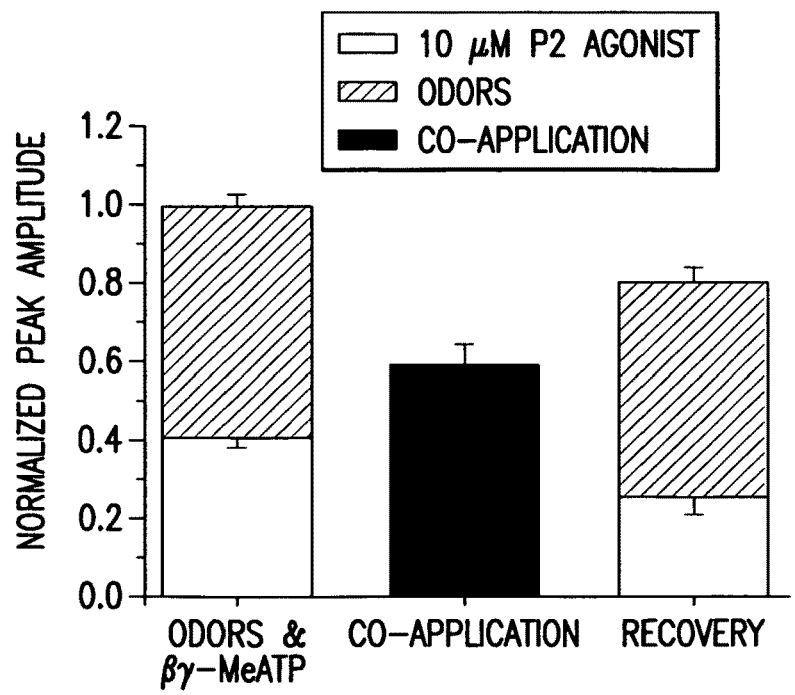
Figure 6E:
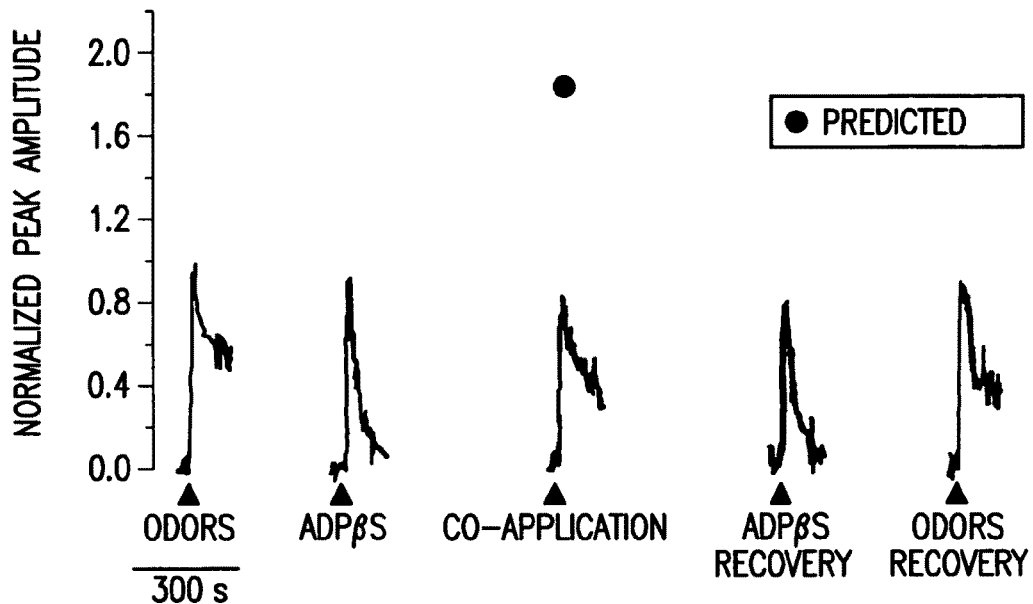
Figure 6F:
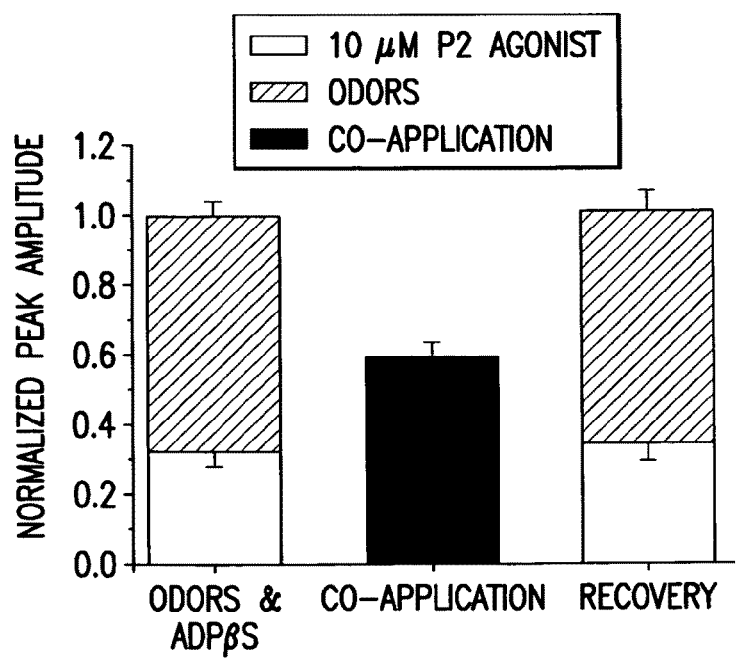

The observation of both suppressive and combined responses indicates that ATP can modulate odor responses via activation of different purinergic receptor subtypes. This hypothesis was tested by sequentially superfusing odors, various selective purinergic receptor agonists and the combination of odors and purinergic receptor agonists onto the olfactory epithelium slice preparation. We found that co-application of the P2X agonist βγ-methylene ATP (10 µM) and odor (1) enhanced the calcium transient amplitude by 168±44% (2/16 cells; FIGS. 6A-B), (2) had no effect on amplitude (15±1%; 2/16 cells; data not shown), or (3) suppressed the amplitude of $Ca^{2+}$ transient by 42±5% (2/16 cells; FIGS. 6C-D). Overall, there is a statistically significant 25±11% reduction in the average amplitude of the $Ca^{2+}$ transient by co-application of odors and βγ-methylene ATP (16/16 cells; p<0.04, paired Student's t-test), even when including the 2 cells that did not show a significant change and the 2 cells that had an enhanced response. In contrast, co-application of the P2Y agonist ADPβS (100 µM) and odor suppressed the $Ca^{2+}$ transient amplitude by 41±4% (15/15 cells; p<0.001, paired Student's t-test; FIGS. 6E-F). Thus, the P2Y agonist ADPβS reduced the odor responsiveness of ORNs in all cells tested. In contrast, βγ-methylene ATP, like ATP, enhanced the odor responsiveness due to the activation of P2X receptors in a few cells. However, in the majority of ORNs, the P2X specific agonist significantly reduced odor-induced $Ca^{2+}$ transients.

Disclosed herein, purinergic receptor subtypes are differentially expressed in ORNs and sustentacular cells, and ORNs express multiple purinergic receptor subtypes. In other cell types, expression of more than one type of purinergic receptor allows for regulation of multiple effectors and modification of agonist-evoked responses, and provides a mechanism for rapid and local fine tuning at the cellular level (Ralevic and Burnstock, 1998). Disclosed immunohistochemical studies showed a notable absence of purinergic receptors in the dendritic knobs and cilia, the site of odor transduction, whereas both P2X and P2Y receptors are located on cell somas and other regions. This indicates that purinergic receptor activation is unlikely to affect initial odor-induced receptor potentials, but can shape the final integrated output of the cell. Extracellular purine nucleotides have been reported to exert multiple trophic actions in the central nervous system (Neary et al., 1996). Because the olfactory neuroepithelium is constantly exposed to airborne pollutants and microbes, it continuously regenerates; different populations of neurons are in various stages of development, including birth, maturation, and programmed cell death or apoptosis (Graziadei and Monti-Graziadei, 1978). Thus, ATP released by acutely injured cells could act as an early signal of cell and tissue damage, and, due to the mitogenic and growth-promoting effects of purinergic receptor activation, stimulate regeneration. Growth promotion can be mediated by P2Y receptors, which, like other growth factor receptors, induce a cascade of intracellular events that trigger cell proliferation (Neary et al., 1996).

A longstanding dogma, that odor sensitivity is not modulated at the level of the olfactory epithelium, is based on anatomical studies showing absence of efferent synapses on ORNs (Getchell, 1986; Graziadei, 1971). A recent study showing release of ATP in the olfactory epithelium following noxious stimuli (Kilgour et al., 2000) provides a physiological source for a neuromodulatory substance that does not require efferent innervation.

b) Experimental Procedures (1) RT-PCR

Total RNA was isolated from rat olfactory epithelium using Trizol (GIBCO BRL). Polyadenylated mRNA was selected using a cellulose oligo(dT) matrix (QuickPrep® Micro mRNA purification kit, Amersham Pharmacia Biotech). First-strand cDNA was prepared from 40 ng mRNA using SuperScript™ II RNase H-RT according to GIBCO BRL procedures. A control reaction omitting the reverse transcriptase was included to confirm absence of genomic contamination. First strand cDNA was amplified using Platinum®Taq DNA polymerase (Gibco BRL). Primers for detection of $P2X_2$ transcripts were 756-775 sense and 1537-1558 antisense oligonucleotides (accession #U14414)(Brake et al., 1994), primers for $P2Y_2$ transcripts were 1288-1307 sense and 1931-1950 antisense oligonucleotides (accession #U09402), primers for β-actin transcripts (Lopez-Candales et al., 1995) were 1038-1067 sense and 1875-1905 antisense oligonucleotides and primers for neuron specific enolase were 348-368 sense and 1101-1123 antisense oligonucleotides (accession #M11931). All the primer pairs (100 μM) were used with a 30-cycle profile performed as follows: 94° C. denaturation (2 min), 96° C. denaturation (45 s), 60° C. annealing (1 min) and 72° C. extension (1.5 min). PCR products were separated and visualized using ethidium bromide-stained agarose gels (1%). A semi-nested PCR protocol was used for detection of the $P2X_2$ receptor transcript. PCR products were excised from the gel and reamplified for 28 cycles using the same antisense primer and a sense primer corresponding to position 1059-1078. PCR products were sequenced at the University of Utah Sequencing Center.

(2) Immunohistochemistry

All animal procedures were approved by the University of Utah Institutional Animal Care and Use Commnittee, and all applicable guidelines from the National Institutes of Health Guide for Care and Use of Laboratory Animals were followed. Olfactory epithelium from post-natal day 4 mice was dissected and post-fixed for 2 hours and then cryoprotected, oriented in Tissue Tek OCT and quickly frozen. Cryostat sections (14 μm) were permeabilized with 0.3% triton X-100 in PBS, blocked with 10% normal donkey serum. Double-labeling was performed by simultaneously incubating slices in goat anti-OMP (1:10K; generous gift from F. Margolis) and either rabbit anti-$P2X_1$, $P2X_2$, $P2X_4$, $P2Y_2$ (all 1:100; Alomone Labs, Jerusalem, Israel), or $P2X_2$ (3 mg/ml; Oncogene Research Products, Boston, Mass.) overnight followed by a 30 min. incubation in TRITC-conjugated donkey anti-goat immunoglobin secondary antibody plus FITC-conjugated donkey anti-rabbit immunoglobin secondary antibody (1:100)(both from Jackson ImmunoResearch Labs, West Grove, Pa.). For pre-absorption controls, P2 antibodies were incubated with a saturating amount of peptide immunogen (10×) for 1-2 hours and visualized as above.

(3) Olfactory Epithelium Slices and Primary Cultures

To prepare olfactory epithelium slices, neonatal mice (postnatal day 0-6) were quickly decapitated, and the skin and lower jaw were removed. Tissue was mounted in ice cold Ringers onto a vibratome-cutting block and 300 μm slices were made. Primary cultures of mouse ORNs were made using the same protocol and culture conditions as described for rat olfactory receptor neurons (Vargas and Lucero, 1999a). Briefly, tissue was placed in divalent cation-free Ringers containing 10 mg/ml bovine serum albumin, 1 mg/ml deoxyribonuclease II and 44 U/ml dispase, incubated at 37° C. for 45 min. The tissue was washed, triturated, and filtered through a 53 mm mesh and 200 ml cells were plated onto concanavalin A-coated coverslips and allowed to settle for 20 min. An additional 1.5 ml of culture medium was added (DMEM supplemented with 100 mM ascorbic acid, 1X insulin-transferrin-seleniumX (GIBCO BRL), 2 mM glutamine, 100 U/ml penicillin G and 100 mg/ml streptomycin).

(4) Electrophysiology

The nystatin perforated-patch technique (Horn and Marty, 1988) was used to examine cells under voltage-clamp. Electrodes (2-5 MΩ) were filled with TMA-oxide internal solution (in mM: 62.5 TMA oxide, 62.5 $KH_2PO_4$, 15 KCl, 5 $MgCl_2$, 11 EGTA, 10 HEPES, 1 glutathione, 5 TEA, 0.03% pluronic acid F-127, 0.3% DMSO, 150 mg/ml nystatin, pH 7.2, 330 mOsm).

Electro-olfactogram and on-cell recordings: Slices of P0-P6 mouse OE were prepared as described above and mounted in a perfusion chamber with a bath flow of 3 min/min. Test chemicals were introduced using a rotary injection valve (Rheodyne, Cotati, Calif.). The electro-olfactogram (EOG) recording electrode (3 M NaCl in 1% agar; tip diameter, 5-10 um) was positioned along the dorsal portion of the nasal septum. The differential electrode (identical to the recording electrode) was positioned over skull cartilage and an $Ag^2/AgCl_2$ ground electrode was connected to the bath solution via a 3 M KCl agar bridge. Responses to test agents were amplified (5000× gain) and filtered (2 kHz) by a low-noise differential DC amplifier. Data was digitized (100 Hz) using Axoscope 8.0 software (Axon Instruments).

For the noninvasive on-cell recordings (Chiu et al., 1997), the same electronics were used as described for nystatin-patch experiments. The recording electrode (5-8 M_resistance) contained Ringer's solution. Test solutions were selected using a rotary valve and delivered for 30 sec using gravity flow. The time course of solution delivery was determined by placing an electrode in a slice and switching from Ringer's solution to distilled water. There was a 3 sec delay to initial electrical response, which peaked at 10 sec. The shaded region in FIG. 8 shows the 30 sec window of when the valve was switched on and off. During a recording, the electrode was lowered into the dorsal septal region of the slice and a seal (0.5-1 Gohms) was made in voltage-clamp before switching to currentclamp with zero applied current. Only cells with a stable baseline were used. There was a 7 min wash between each test application. Experiments were conducted on 65 cells in 42 slices obtained from 14 P0-P6 mice from three litters. Only three cells survived long enough to complete the recovery portion of the >27 min protocol.

(5) Confocal Calcium Imaging $[Ca^{2+}]_i$ was determined using confocal imaging of fluo-4 AM (18 µM; Molecular Probes) loaded cells and slices. Cells or slices were placed in a laminar flow chamber (Warner Instruments) and perfused continuously with Ringers solution at a flow rate of 1.5-2.0 ml/min. Ringers contained (mM): 140 NaCl, 5 KCl, 1 $MgCl_2$, 2 $CaCl_2$, 10 HEPES, 10 glucose, 500 probenicid and 400 nM tetrodotoxin. Test solutions were applied using bath exchange and a small volume loop injector (200 µl). A Zeiss LSM 510 confocal laser scanning system was used for data collection and analysis. Time series experiments were performed collecting 1400×700 pixel images at 0.2-0.4 Hz. The fluorometric signals obtained are expressed as relative fluorescence change, $\Delta F/F = (F - F0)/F_0$, where $F_0$ is the basal fluorescence level. Increases in F greater than 10% above baseline noise were considered responses.

2. Example 2

Purinergic Receptor Antagonists Potentiate Odor Sensitivity

Figure 12A:
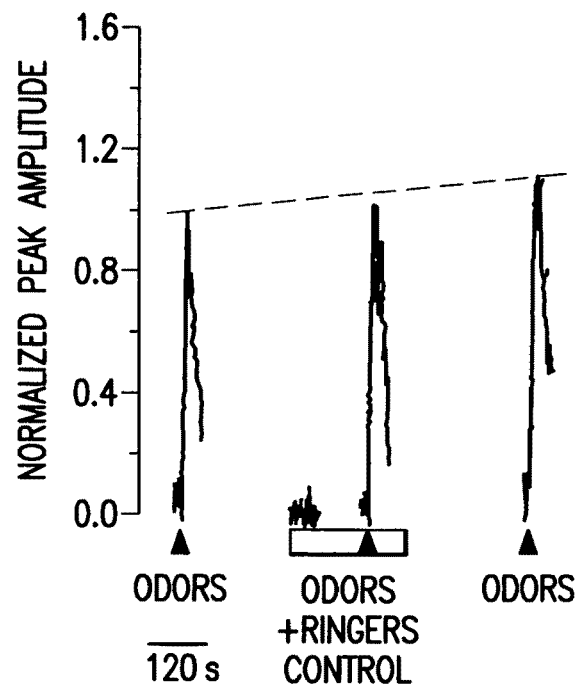
Figure 12B:
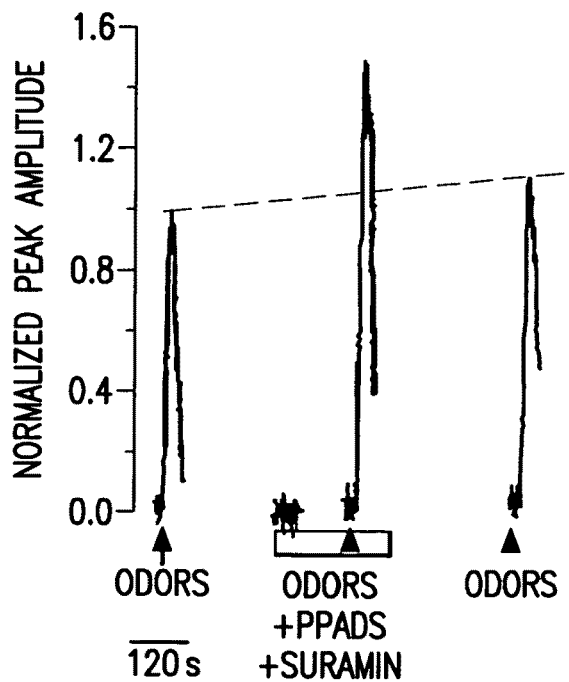
Figure 12C:
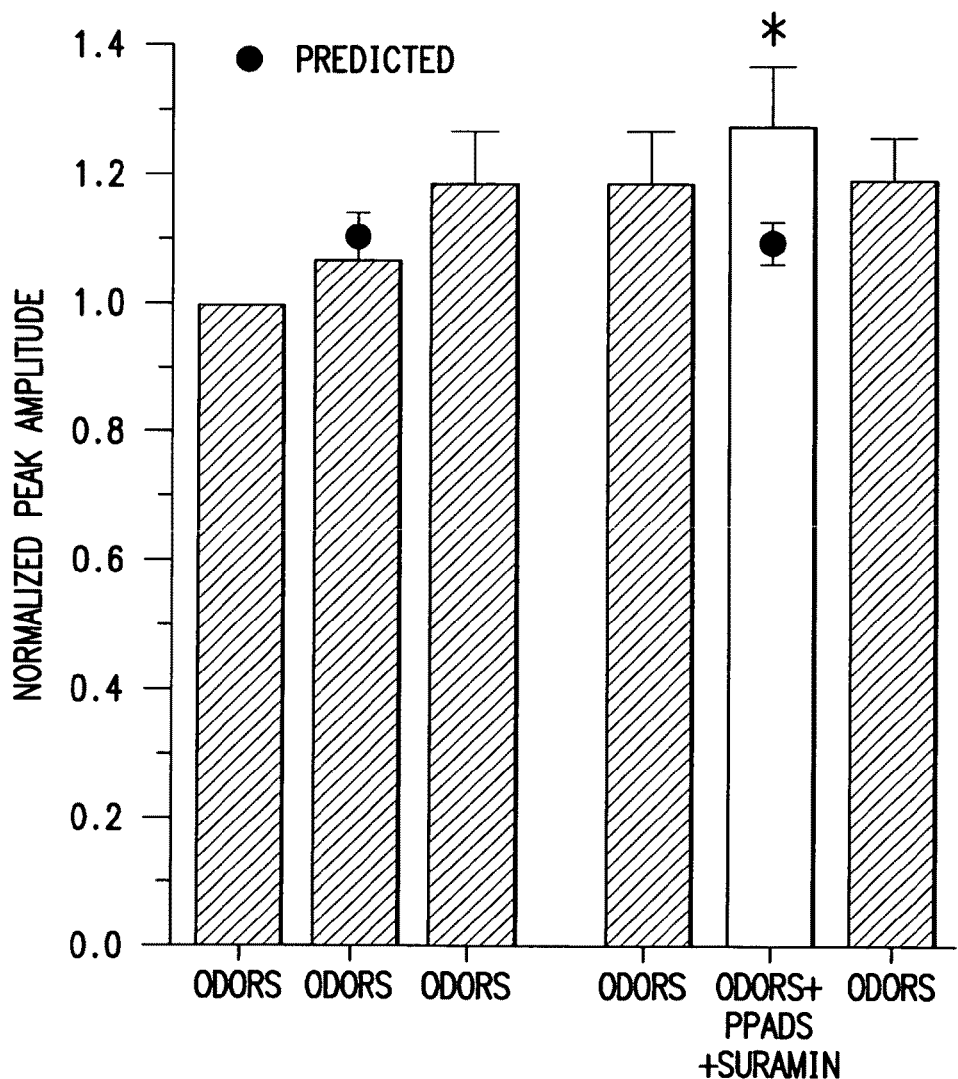
Figure 12D:
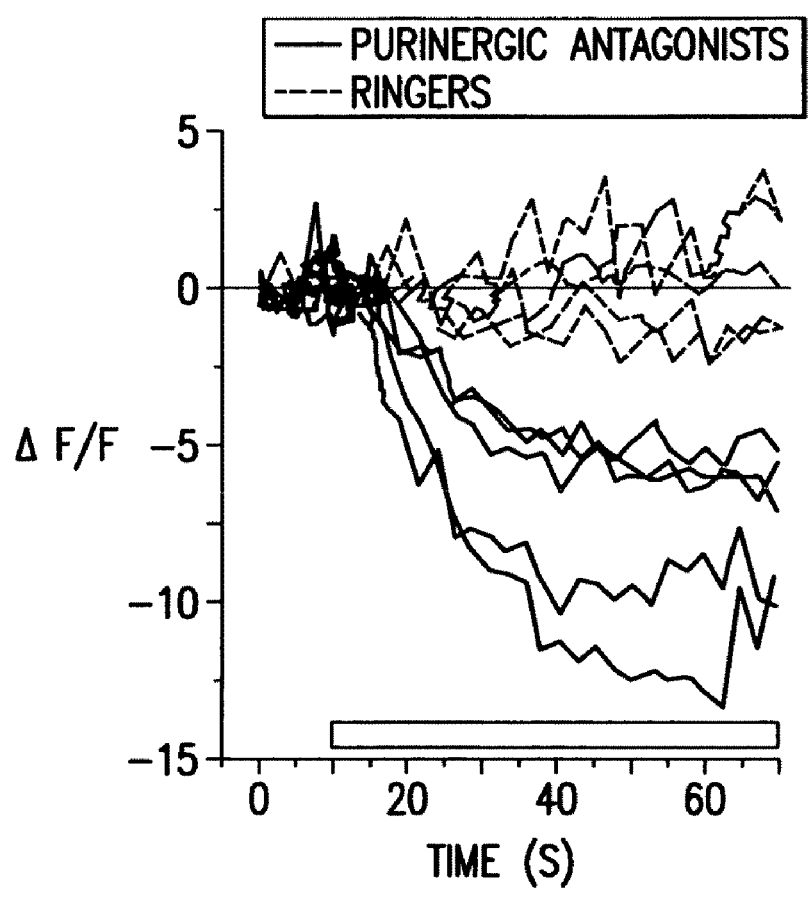

If the predominate role of endogenous ATP is to reduce odor sensitivity then addition of purinergic receptor antagonists should potentiate odor responses. Control experiments in which we applied odors at 5-8 min intervals revealed a small linear increase in the peak amplitude of the odor-induced $Ca^{2+}$ transient (FIGS. 12A & C). A linear regression between the first and last odor application was performed and the predicted amplitude of the middle response was calculated. Based on linear regressions, the actual amplitude of the middle odor application was not significantly different from the predicted amplitude, both in the single cell shown in FIG. 12A and in the average of 30 cells in FIG. 12C (n=30; −3±4% difference; paired Student's t-test, p=0.47). In contrast, when the middle odor application was preceded by and concomitant with perfusion of purinergic receptor antagonists (100 µM suramin+25 µM PPADS), a significant increase in the $Ca^{2+}$ transient amplitude such that the mean observed response was 14±5% larger than the predicted (n=22; paired Student's t-test, p=0.024). The differences between predicted and observed were statistically different when the control group was compared to the purinergic receptor agonist-treated group (independent Students t-test, p=0.012). Application of purinergic receptor antagonists alone did not evoke calcium transients (FIG. 12B second trace). The elevated odor-evoked calcium transients would be expected if basal extracellular ATP were habitually reducing ORN sensitivity. Thus, the data shows that both endogenous and exogenous ATP reduces the amplitude of odor-evoked calcium transients through purinergic receptors, suggesting that ATP modulates ORN sensitivity.

3. Example 3

ATP Reduces Cyclic Nucleotide-Induced Electrical Responses

Figure 13B:
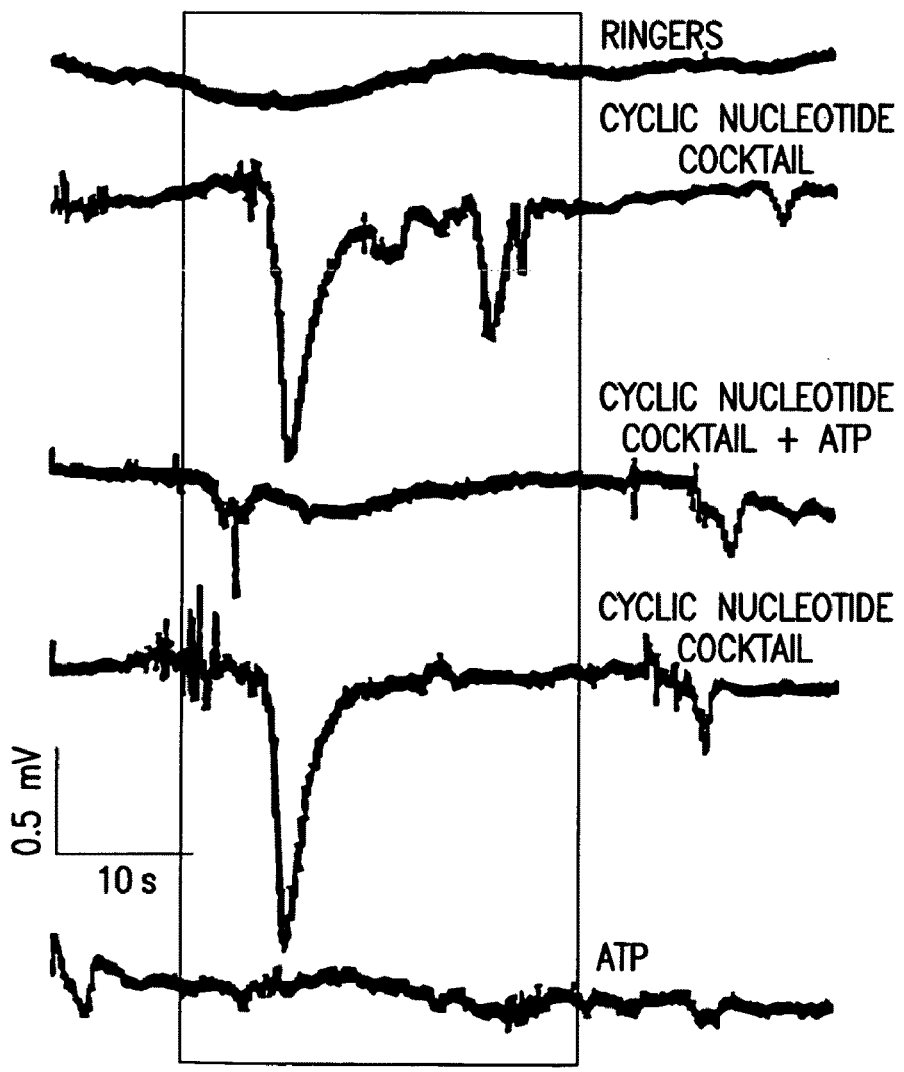
Figure 13C:
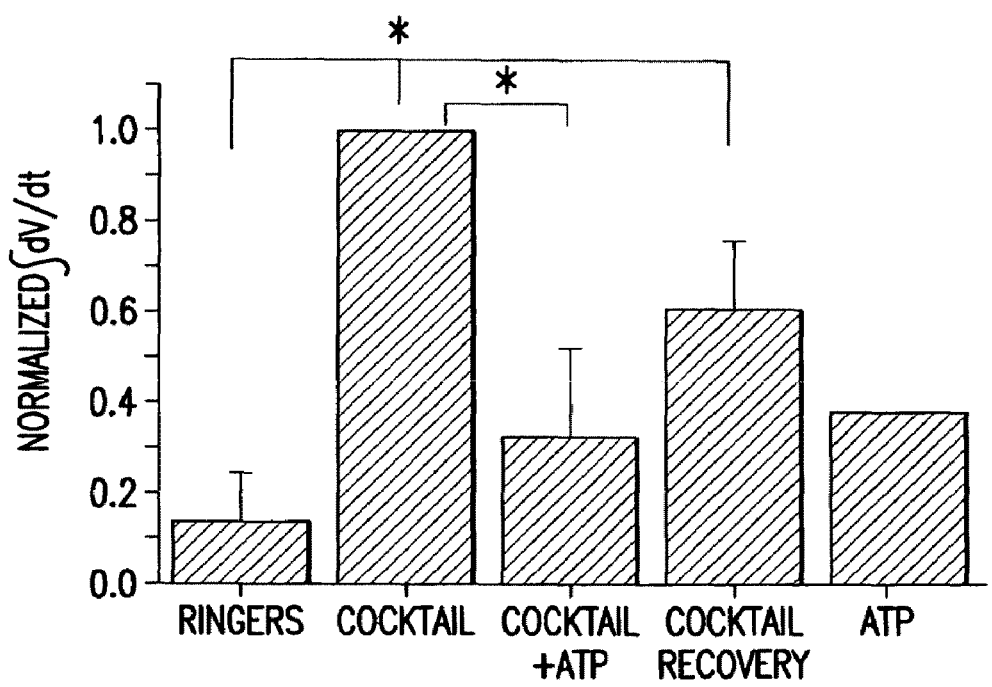

Odor activation of G-protein-coupled receptors results in increased cAMP production, opening of cyclic nucleotide-gated channels, influx of $Ca^{2+}$ and $Na^+$, depolarization of the membrane, and activation of voltage- and $Ca^{2+}$-gated ion channels (Schild and Restrepo, 1998). Based on calcium imaging data, purinergics can reduce the odor-evoked electrical activity of ORNs. Recording odor-evoked membrane responses from single ORNs has a low probability of success because each ORN expresses only one or a few odorant receptors (Buck and Axel, 1991). Thus, a mixture of cyclic nucleotide modulators were used to record membrane responses: IBMX (100 µM), a phosphodiesterase inhibitor that prevents the breakdown of cAMP, CPT-cAMP (50 M), and 8-Br-cGMP (50 µM), both membrane-permeant analogs of cAMP and cGMP, respectively. This cyclic nucleotide mixture was tested initially to verify that it evoked membrane potential changes in the OE slice preparation. The EOG measures field potential changes across the OE after stimulation. Similar EOG responses were obtained from both odor (10 µM) and the cyclic nucleotide mixture (FIG. 13A), validating the replacement of odor with the mixture in subsequent recordings. Next on-cell current-clamp recordings of ORNs were performed from neonatal mouse slices. The cyclic nucleotide mixture, the mixture+ATP, a second application of the mixture, and ATP was sequentially superfused onto a slice preparation and membrane potential changes were measured (FIG. 13B). The coapplication of ATP and the cyclic nucleotide mixture suppressed the cyclic nucleotide-induced electrical responses. The membrane response from each ORN was integrated from baseline and normalized to the initial cyclic nucleotide mixture response. The presence of ATP reduced the electrical activity of the ORN by 67±2% (FIG. 13C)(n=3 cells; p<0.01, Newman-Keuls post hoc test). These data show that ATP modulates odor sensitivity in mammalian olfactory neurons.

G. Sequences

1. SEQ ID NO:1 The Following is the Sequence for *H. sapiens* mRNA for ATP Receptor P2X1 (Accession Number X83688). Other Sequences have been Published for P2X1 Receptors from Rat Vas Deferens (Accession Number X80477) and Mouse Urinary Bladder (Accession Number X84896).

```
  1  gaattcggct gatcccgcgg caggtgctag caggagctgg
     cagcatgggc tccccagggg
 61  ctacgacagg ctgggggctt ctggattata agacggagaa
     gtatgtgatg accaggaact
121  ggcgggtggg cgccctgcag aggctgctgc agtttgggat
     cgtggtctat gtggtagggt
```

-continued

```
 181  gggctctcct cgccaaaaaa ggctaccagg agcgggacct
      ggaaccccag tttttccatca 241  tcaccaaact caaaggggtt tccgtcactc agatcaagga
      gcttggaaac cggctgtggg 301  atgtggccga cttcgtgaag ccacctcagg gagagaacgt
      gttcttcttg gtgaccaact 361  tccttgtgac gccagcccaa gttcagggca gatgcccaga
      gcacccgtcc gtcccactgg
```

-continued

```
 421  ctaactgctg ggtcgacgaa gactgccccg aaggggaggg
      aggcacacac agccacggtg 481  taaaaacagg ccagtgtgtg gtgttcaatg ggacccacag
      gacctgtgag atctggagtt 541  ggtgcccagt ggagagtggc gttgtgccct cgaggcccct
      gctggcccag gcccagaact 601  tcacactgtt catcaaaaac acagtcacct tcagcaagtt
      caacttctct aagtccaatg 661  ccttggagac ctgggacccc acctatttta agcactgccg
      ctatgaacca caattcagcc 721  cctactgtcc cgtgttccgc attggggacc tcgtggccaa
      ggctggaggg accttcgagg 781  acctggcgtt gctgggtggc tctgtaggca tcagagttca
      ctgggattgt gacctggaca 841  ccggggactc tggctgctgg cctcactact ccttccagct
      gcaggagaag agctacaact 901  tcaggacagc cactcactgg tgggagcaac cgggtgtgga
      ggcccgcacc ctgctcaagc 961  tctatggaat ccgcttcgac atcctcgtca ccgggcaggc
      agggaagttc gggctcatcc 1021  ccacggccgt cacactgggc accggggcag cttggctggg
      cgtggtcacc ttttctgtg 1081  acctgctact gctgtatgtg gatagagaag cccatttcta
      ctggaggaca aagtatgagg 1141  aggccaaggc cccgaaagca accgccaact ctgtgtggag
      ggagctggcc tttgcatccc 1201  aagcccgact ggccgagtgc ctcagacgga gctcagcacc
      tgcacccacg gccactgctg
```

-continued

```
1261  ctgggagtca gacacagaca ccaggatggc cctgtccaag
      ttctgacacc cacttgccaa 1321  cccattccgg gagcctgtag ccgtttccct gctggttgag
      aagagagagg ggctgggcaa 1381  ggaaggaccc ctgccctgcc gagcgaaagc aaggatgagg
      caacagcaat gaaagaagat 1441  caagccgaat tc
```

2. SEQ ID NO:2 the Following is the Sequence for *H. sapiens Protein for ATP Receptor P2X1* (Accession Number X83688).

```
MARRFQEELAAFLFEYDTPRMVLVRNKKVGVIFRLIQLVVLVYV

IGWVFLYEKGYQTSSGLISSVSVKLKGLAVTQLPGLGPQVWDVADYVFPAGGDNSFVV

MTNFIVTPKQTQGYCAEHPEGGICKEDSGCTPGKAKRKAQGIRTGKCVAFNDTVKTCE

IFGWCPVEVDDDIPRPALLREAENFTLFIKNSISFPRFKVNRRNLVEEVNAAHMKTCL

FHKTLHPLCPVFQLGYVVQESGQNFSTLAEKGGVVGITIDWHCDLDWHVRHCPPIYEF

HGLYEEKNLSPGFNFRFARHFVENGTNYRHLFKVFGIRFDILVDGKAGKFDIIPTMTT

IGSGIGIFGVATVLCDLLLLHILPKRHYYKQKKFKYAEDMGPGAAERDLAATSSTLGL

QENMRTS
```

3. SEQ ID NO:3 The Following Sequence for the P2X2 Receptor is Derived from Rat PC12 Cells (Accession Number U14414). Other Sequences have been Published for P2X2 Receptors from Rat Cerebellum (Accession Number Y09910)

```
   1  gaattcggct gatcccgcgg caggtgctag caggagctgg
      cagcatgggc tccccagggg 61  ctacgacagg ctgggggctt ctggattata agacggagaa
      gtatgtgatg accaggaact 121  ggcgggtggg cgcccgcag aggctgctgc agtttgggat
      cgtggtctat gtggtagggt 181  gggctctcct cgccaaaaaa ggctaccagg agcgggacct
      ggaaccccag tttttccatca 241  tcaccaaact caaaggggtt tccgtcactc agatcaagga
      gcttggaaac cggctgtggg 301  atgtggccga cttcgtgaag ccacctcagg gagagaacgt
      gttcttcttg gtgaccaact 361  tccttgtgac gccagcccaa gttcagggca gatgcccaga
      gcacccgtcc gtcccactgg 421  ctaactgctg ggtcgacgaa gactgccccg aaggggaggg
      aggcacacac agccacggtg 481  taaaaacagg ccagtgtgtg gtgttcaatg ggacccacag
      gacctgtgag atctggagtt 541  ggtgcccagt ggagagtggc gttgtgccct cgaggcccct
      gctggcccag gcccagaact 601  tcacactgtt catcaaaaac acagtcacct tcagcaagtt
      caacttctct aagtccaatg 661  ccttggagac ctgggacccc acctatttta agcactgccg
      ctatgaacca caattcagcc
```

```
 721  cctactgtcc cgtgttccgc attggggacc tcgtggccaa
      ggctggaggg accttcgagg 781  acctggcgtt gctgggtggc tctgtaggca tcagagttca
      ctgggattgt gacctggaca 841  ccggggactc tggctgctgg cctcactact ccttccagct
      gcaggagaag agctacaact 901  tcaggacagc cactcactgg tgggagcaac cgggtgtgga
      ggcccgcacc ctgctcaagc 961  tctatggaat ccgcttcgac atcctcgtca ccgggcaggc
      agggaagttc gggctcatcc 1021  ccacggccgt cacactgggc accggggcag cttggctggg
      cgtggtcacc tttttctgtg 1081  acctgctact gctgtatgtg gatagagaag cccatttcta
      ctggaggaca aagtatgagg 1141  aggccaaggc cccgaaagca accgccaact ctgtgtggag
      ggagctggcc tttgcatccc 1201  aagcccgact ggccgagtgc ctcagacgga gctcagcacc
      tgcacccacg gccactgctg 1261  ctgggagtca gacacagaca ccaggatggc cctgtccaag
      ttctgacacc cacttgccaa 1321  cccattccgg gagcctgtag ccgtttccct gctggttgag
      aagagagagg ggctgggcaa 1381  ggaaggaccc ctgccctgcc gagcgaaagc aaggatgagg
      caacagcaat gaaagaagat 1441  caagccgaat tc
```

4. SEQ ID NO:4 The Following Sequence for the P2X2 Receptor is Derived from Rat PC12 Cells (Accession Number U14414) Protein Sequence.

MVRRLARGCWSAFWDYETPKVIVVRNRRLGFVHRMVQLLILLYF

VWYVFIVQKSYQDSETGPESSIITKVKGITMSEDKVWDVEEYVKPPEGGSVVSIITRI

EVTPSQTLGTCPESMRVHSSTCHSDDDCIAGQLDMQGNGIRTGHCVPYYHGDSKTCEV

SAWCPVEDGTSDNHFLGKMAPNFTILIKNSIHYPKFKFSKGNIASQKSDYLKHCTFDQ

DSDPYCPIFRLGFIVEKAGENFTELAHKGGVIGVIINWNCDLDLSESECNPKYSFRRL

DPKYDPASSGYNFRFAKYYKINGTTTTRTLIKAYGIRIDVIVHGQAGKFSLIPTIINL

ATALTSIGVGSFLCDWILLTFMNKNKLYSHKKFDKVRTPKHPSSRWPVTLALVLGQIP

PPPSHYSQDQPPSPPSGEGPTLGEGAELPLAVQSPRPCSISALTEQVVDTLGQHMGQR

PPVPEPSQQDSTSTDPKGLAQL

5. SEQ ID NO:5 The Following Sequence for the P2X3 Receptor is Derived from *H. sapiens* (Accession Number Y07683). Other Sequences have been Published for P2X3 Receptors from Rat Dorsal Root Ganglion (Accession Number X91167 and X90651).

```
   1  gaattcggct gatcccgcgg caggtgctag caggagctgg
      cagcatgggc tccccagggg 61  ctacgacagg ctgggggctt ctggattata agacggagaa
      gtatgtgatg accaggaact 121  ggcgggtggg cgccctgcag aggctgctgc agtttgggat
      cgtggtctat gtggtagggt 181  gggctctcct cgccaaaaaa ggctaccagg agcgggacct
      ggaaccccag ttttccatca 241  tcaccaaact caaaggggtt tccgtcactc agatcaagga
      gcttggaaac cggctgtggg 301  atgtggccga cttcgtgaag ccacctcagg gagagaacgt
      gttcttcttg gtgaccaact 361  tccttgtgac gccagcccaa gttcagggca gatgcccaga
      gcacccgtcc gtcccactgg 421  ctaactgctg ggtcgacgaa gactgccccg aaggggaggg
      aggcacacac agccacggtg 481  taaaaacagg ccagtgtgtg gtgttcaatg ggacccacag
      gacctgtgag atctggagtt 541  ggtgcccagt ggagagtggc gttgtgccct cgaggcccct
      gctggcccag gcccagaact 601  tcacactgtt catcaaaaac acagtcacct tcagcaagtt
      caacttctct aagtccaatg 661  ccttggagac ctgggacccc acctatttta agcactgccg
      ctatgaacca caattcagcc 721  cctactgtcc cgtgttccgc attggggacc tcgtggccaa
      ggctggaggg accttcgagg 781  acctggcgtt gctgggtggc tctgtaggca tcagagttca
      ctgggattgt gacctggaca 841  ccggggactc tggctgctgg cctcactact ccttccagct
      gcaggagaag agctacaact 901  tcaggacagc cactcactgg tgggagcaac cgggtgtgga
      ggcccgcacc ctgctcaagc 961  tctatggaat ccgcttcgac atcctcgtca ccgggcaggc
      agggaagttc gggctcatcc 1021  ccacggccgt cacactgggc accggggcag cttggctggg
      cgtggtcacc tttttctgtg 1081  acctgctact gctgtatgtg gatagagaag cccatttcta
      ctggaggaca aagtatgagg 1141  aggccaaggc cccgaaagca accgccaact ctgtgtggag
      ggagctggcc tttgcatccc
```

6. SEQ ID NO:6 The Following Sequence for the P2X3 Receptor is Derived from *H. sapiens* (Accession Number Y07683) Protein Sequence.

```
MNCISDFFTYETTKSVVVKSWTIGIINRVVQLLIISYFVGWVFL

HEKAYQVRDTAIESSVVTKVKGSGLYANRVMDVSDYVTPPQGTSVFVIITKMIVTENQ

MQGFCPESEEKYRCVSDSQCGPEPLPGGGILTGRCVNYSSVLRTCEIQGWCPTEVDTV

ETPIMMEAENFTIFIKNSIRFPLFNFEKGNLLPNLTARDMKTCRFHPDKDPFCPILRV

GDVVKFAGQDFAKLARTGGVLGIKIGWVCDLDKAWDQCIPKYSFTRLDSVSEKSSVSP

GYNFRFAKYYKMENGSEYRTLLKAFGIRFDVLVYGNAGKFNIIPTIISSVAAFTSVGV

GTVLCDIILLNFLKGADQYKAKKFEEVNETTLKIAALTNPVYPSDQTTAEKQSTDSGA

FSIGH
```

7. SEQ ID NO:7 The Following Sequence for the P2X4 Receptor is Derived from *H. sapiens* (Accession Number Y07684). Other Sequences have been Published for P2X4 Receptors from Rat Brain (Accession Number X93565, U32497, X91200 and X87763) and Rat Pancreatic Islet (Accession Number U47031).

```
   1 gaattcggct gatcccgcgg caggtgctag caggagctgg
     cagcatgggc tccccagggg 61 ctacgacagg ctggggctt ctggattata agacggagaa
     gtatgtgatg accaggaact 121 ggcgggtggg cgccctgcag aggctgctgc agtttgggat
     cgtggtctat gtggtagggt 181 gggctctcct cgccaaaaaa ggctaccagg agcgggacct
     ggaaccccag tttttccatca 241 tcaccaaact caaaggggtt tccgtcactc agatcaagga
     gcttggaaac cggctgtggg 301 atgtggccga cttcgtgaag ccacctcagg gagagaacgt
     gttcttcttg gtgaccaact 361 tccttgtgac gccagcccaa gttcagggca gatgcccaga
     gcacccgtcc gtcccactgg 421 ctaactgctg ggtcgacgaa gactgccccg aaggggaggg
     aggcacacac agccacggtg 481 taaaaacagg ccagtgtgtg gtgttcaatg ggacccacag
     gacctgtgag atctggagtt 541 ggtgccagt ggagagtggc gttgtgccct cgaggcccct
     gctggcccag gcccagaact 601 tcacactgtt catcaaaaac acagtcacct tcagcaagtt
     caacttctct aagtccaatg 661 ccttggagac ctgggacccc acctatttta agcactgccg
     ctatgaacca caattcagcc 721 cctactgtcc cgtgttccgc attgggacc tcgtggccaa
     ggctggaggg accttcgagg 781 acctggcgtt gctgggtggc tctgtaggca tcagagttca
     ctgggattgt gacctggaca 841 ccggggactc tggctgctgg cctcactact ccttccagct
     gcaggagaag agctacaact 901 tcaggacagc cactcactgg tgggagcaac cgggtgtgga
     ggcccgcacc ctgctcaagc 961 tctatggaat ccgcttcgac atcctcgtca ccgggcaggc
     agggaagttc gggctcatcc 1021 ccacggccgt cacactgggc accggggcag cttggctggg
     cgtggtcacc tttttctgtg 1081 acctgctact gctgtatgtg gatagagaag cccatttcta
     ctggaggaca aagtatgagg 1141 aggccaaggc cccgaaagca accgccaact ctgtgtggag
     ggagctggcc tttgcatccc 1201 aagcccgact ggccgagtgc ctcagacgga gctcagcacc
     tgcacccacg gccactgctg 1261 ctgggagtca gacacagaca ccaggatggc cctgtccaag
     ttctgacacc cacttgccaa 1321 cccattccgg gagcctgtag ccgtttccct gctggttgag
     aagagagagg ggctgggcaa 1381 ggaaggaccc ctgccctgcc gagcgaaagc aaggatgagg
     caacagcaat gaaagaagat 1441 caagccgaat tc
```

8. SEQ ID NO:8 The Following Sequence for the P2X4 Receptor is Derived from *H. sapiens* (Accession Number Y07684) Protein Sequence.

MAGCCSALAAFLFEYDTPRIVLIRSRKVGLMNRAVQLLILAYVI
GWVFVWEKGYQETDSVVSSVTTKVKGVAVTNTSKLGFRIWDVADYVIPAQEENSLFVM
TNVILTMNQTQGLCPEIPDATTVCKSDASCTAGSAGTHSNGVSTGRCVAFNGSVKTCE
VAAWCPVEDDTHVPQPAFLKAAENFTLLVKNNIWYPKFNFSKRNILPNITTTYLKSCI
YDAKTDPFCPIFRLGKIVENAGHSPQDMAVEGGIMGIQVNWDCNLDRAASLCLPRYSF
RRLDTRDVEHNVSPGYNFRFAKYYRDLAGNEQRTLIKAYGIRFDIIVFGKAGKFDIIP
TMINIGSGLALLGMATVLCDIIVLYCMKKRLYYREKKYKYVEDYEQGLASELDQ

9. SEQ ID NO:9 The Following Sequence for the P2X5 Receptor is Derived from *H. sapiens* (Accession Number AF016709). Other Sequences have been Published for P2X5 Receptors from Rat Brain (Accession Number X92069) and Rat Heart (Accession Number X97328).

```
   1 ggcacgaggg tccgcaagcc cggctgagag cgcgccatgg
     ggcaggcggg ctgcaagggg
  61 ctctgcctgt cgctgttcga ctacaagacc gagaagtatg
     tcatcgccaa gaacaagaag
 121 gtgggcctgc tgtaccggct gctgcaggcc tccatcctgg
     cgtacctggt cgtatgggtg
 181 ttcctgataa agaagggtta ccaagacgtc gacacctccc
     tgcagagtgc tgtcatcacc
 241 aaagtcaagg gcgtggcctt caccaacacc tcggatcttg
     ggcagcggat ctgggatgtc
 301 gccgactacg tcattccagc ccagggagag aacgtctttt
     ttgtggtcac caacctgatt
 361 gtgaccccca accagcggca gaacgtctgt gctgagaatg
     aaggcattcc tgatggcgcg
 421 tgctccaagg acagcgactg ccacgctggg gaagcggtta
     cagctggaaa cggagtgaag
 481 accggccgct gcctgcggag agggaacttg gccaggggca
     cctgtgagat cttttgcctgg
 541 tgcccgttgg agacaagctc caggccggag gagccattcc
     tgaaggaggc cgaagacttc
 601 accattttca taaagaacca catccgtttc cccaaattca
     acttctccaa aaacaatgtg
 661 atggacgtca aggacagatc tttcctgaaa tcatgccact
     ttggccccaa gaaccactac
 721 tgccccatct tccgactggg ctccatcgtc cgctgggccg
     ggagcgactt ccaggatata
 781 gccctgcgag gtggcgtgat aggaattaat attgaatgga
     actgtgatct tgataaagct
 841 gcctctgagt gccaccctca ctattctttt agccgtctgg
     acaataaact ttcaaagtct
 901 gtctcctccg ggtacaactt cagatttgcc agatattacc
     gagacgcagc cggggtggag
 961 ttccgcaccc tgatgaaagc ctacgggatc cgctttgacg
     tgatggtgaa cggcaagggt
1021 gctttcttct gcgacctggt actcatctac ctcatcaaaa
     agagagagtt ttaccgtgac
1081 aagaagtacg aggaagtgag gggcctagaa gacagttccc
     aggaggccga ggacgaggca
1141 tcggggctgg ggctatctga gcagctcaca tctgggccag
     ggctgctggg gatgccggag
1201 cagcaggagc tgcaggagcc acccgaggcg aagcgtggaa
     gcagcagtca gaaggggaac
1261 ggatctgtgt gcccacagct cctggagccc cacaggagca
     cgtgaattgc ctctgcttac
1321 gttcaggccc tgtcctaaac ccagccgtct agcacccagt
     gatcccatgc ctttgggaat
1381 cccaggatgc tgcccaacgg gaaatttgta cattgggtgc
     tatcaatgcc acatcacagg
1441 gaccagccat cacagagcaa agtgacctcc acgtctgatg
     ctggggtcat caggacggac
1501 ccatcatggc tgtcttttg ccccacccc tgccgtcagt
     tcttcctttc tccgtggctg
1561 gcttcccgca ctagggaacg ggttgtaaat ggggaacatg
     acttccttcc ggagtccttg
1621 agcacctcag ctaaggaccg cagtgccctg tagagttcct
     agattacctc actgggaata
1681 gcattgtgcg tgtccggaaa agggctccat ttggttccag
     cccactcccc tctgcaagtg
1741 ccacagcttc cctcagagca tactctccag tggatccaag
     tactctctct cctaaagaca
1801 ccaccttcct gccagctgtt tgcccttagg ccagtacaca
     gaattaaagt gggggagatg
1861 gcagacgctt tctgggacct gcccaagata tgtattctct
     gacactgtta tttggtcata
1921 aaacaataaa tggtgtcaat ttcaaaaaaa aaaaaaaaa
     aaaaaaaaaa aaaaaaa
```

10. SEQ ID NO:10 The Following Sequence for the P2X5 Receptor is Derived from *H. sapiens* (Accession Number AF016709) Protein Sequence.

MGQAGCKGLCLSLFDYKTEKYVIAKNKKVGLLYRLLQASILAYL
VVWVFLIKKGYQDVDTSLQSAVITKVKGVAFTNTSDLGQRIWDVADYVIPAQGENVFF
VVTNLIVTPNQRQNVCAENEGIPDGACSKDSDCHAGEAVTAGNGVKTGRCLRRGNLAR
GTCEIFAWCPLETSSRPEEPFLKEAEDFTIFIKNHIRFPKFNFSKNNVMDVKDRSFLK
SCHFGPKNHYCPIFRLGSIVRWAGSDFQDIALRGGVIGINIEWNCDLDKAASECHPHY
SFSRLDNKLSKSVSSGYNFRFARYYRDAAGVEFRTLMKAYGIRFDVMVNGKGAFFCDL
VLIYLIKKREFYRDKKYEEVRGLEDSSQEAEDEASGLGLSEQLTSGPGLLGMPEQQEL
QEPPEAKRGSSSQKGNGSVCPQLLEPHRST

11. SEQ ID NO:11. The Following Sequence for the P2X6 Receptor is Derived from *H. Sapiens* (Accession Number AF065385). Other Sequences have been Published for P2X6 Receptors from Rat Brain (Accession Numbers X92070 and X97376).

```
  1 gaattcggct gatcccgcgg caggtgctag caggagctgg
    cagcatgggc tccccagggg
 61 ctacgacagg ctgggggctt ctggattata agacggagaa
    gtatgtgatg accaggaact
121 ggcgggtggg cgccctgcag aggctgctgc agtttgggat
    cgtggtctat gtggtagggt
181 gggctctcct cgccaaaaaa ggctaccagg agcgggacct
    ggaacccag ttttccatca
241 tcaccaaact caagggggtt tccgtcactc agatcaagga
    gcttggaaac cggctgtggg
301 atgtggccga cttcgtgaag ccacctcagg gagagaacgt
    gttcttcttg gtgaccaact
361 tccttgtgac gccagcccaa gttcagggca gatgcccaga
    gcacccgtcc gtcccactgg
421 ctaactgctg ggtcgacgaa gactgccccg aagggagggg
    aggcacacac agccacggtg
481 taaaaacagg ccagtgtgtg gtgttcaatg gacccacag
    gacctgtgag atctggagtt
541 ggtgcccagt ggagagtggc gttgtgccct cgaggcccct
    gctggcccag gcccagaact
601 tcacactgtt catcaaaaac acagtcacct tcagcaagtt
    caacttctct aagtccaatg
661 ccttggagac ctgggacccc acctatttta agcactgccg
    ctatgaacca caattcagcc
721 cctactgtcc cgtgttccgc attggggacc tcgtggccaa
    ggctggaggg accttcgagg
781 acctggcgtt gctgggtggc tctgtaggoa tcagagttca
    ctgggattgt gacctggaca
841 ccggggactc tggctgctgg cctcactact ccttccagct
    gcaggagaag agctacaact
901 tcaggacagc cactcactgg tgggagcaac cgggtgtgga
    ggcccgcacc ctgctcaagc
961 tctatggaat ccgcttcgac atcctcgtca ccgggcaggc
    agggaagttc gggctcatcc
1021 ccacggccgt cacactgggc accggggcag cttggctggg
    cgtggtcacc tttttctgtg
1081 acctgctact gctgtatgtg gatagagaag cccatttcta
    ctggaggaca aagtatgagg
1141 aggccaaggc cccgaaagca accgccaact ctgtgtggag
    ggagctggcc tttgcatccc
1201 aagcccgact ggccgagtgc ctcagacgga gctcagcacc
    tgcacccacg gccactgctg
1261 ctgggagtca gacacagaca ccaggatggc cctgtccaag
    ttctgacacc cacttgccaa
1321 cccattccgg gagcctgtag ccgtttccct gctggttgag
    aagagagagg ggctgggcaa
1381 ggaaggaccc ctgccctgcc gagcgaaagc aaggatgagg
    caacagcaat gaaagaagat
1441 caagccgaat tc
```

12. SEQ ID NO:12. The Following Sequence for the P2X6 Receptor is Derived from *H. Sapiens* (Accession Number AF065385) Protein Sequence.

MGSPGATTGWGLLDYKTEKYVMTRNWRVGALQRLLQFGIVVYVV
GWALLAKKGYQERDLEPQFSIITKLKGVSVTQIKELGNRLWDVADFVKPPQGENVFFL
VTNFLVTPAQVQGRCPEHPSVPLANCWVDEDCPEGEGGTHSHGVKTGQCVVFNGTHRT
CEIWSWCPVESGVVPSRPLLAQAQNFTLFIKNTVTFSKFNFSKSNALETWDPTYFKHC

RYEPQFSPYCPVFRIGDLVAKAGGTFEDLALLGGSVGIRVHWDCDLDTGDSGCWPHYS

FQLQEKSYNFRTATHWWEQPGVEARTLLKLYGIRFDILVTGQAGKFGLIPTAVTLGTG

AAWLGVVTFFCDLLLLYVDREAHFYWRTKYEEAKAPKATANSVWRELAFASQARLAEC

LRRSSAPAPTATAAGSQTQTPGWPCPSSDTHLPTHSGSL

13. SEQ ID NO:13 The Following Sequence for the P2X7 Receptor is Derived from *H. sapiens* Brain (Accession Number Y09561). Please Note that Other Sequences have been Published for P2X7 Receptors from Rat Brain (Accession Numbers X95882)

```
   1 aaaacgcagg gagggaggct gtcaccatgc cggcctgctg
     cagctgcagt gatgttttcc
  61 agtatgagac gaacaaagtc actcggatcc agagcatgaa
     ttatggcacc attaagtggt
 121 tcttccacgt gatcatcttt tcctacgttt gctttgctct
     ggtgagtgac aagctgtacc
 181 agcggaaaga gcctgtcatc agttctgtgc acaccaaggt
     gaaggggata gcagaggtga
 241 aagaggagat cgtggagaat ggagtgaaga agttggtgca
     cagtgtcttt gacaccgcag
 301 actacacctt ccctttgcag gggaactctt tcttcgtgat
     gacaaacttt ctcaaaacag
 361 aaggccaaga gcagcggttg tgtccgagt atcccacccg
     caggacgctc tgttcctctg
 421 accgaggttg taaaaaggga tggatggacc cgcagagcaa
     aggaattcag accggaaggt
 481 gtgtagtgca tgaagggaac cagaagacct gtgaagtctc
     tgcctggtgc cccatcgagg
 541 cagtggaaga ggccccccgg cctgctctct tgaacagtgc
     cgaaaacttc actgtgctca
 601 tcaagaacaa tatcgacttc cccggccaca actacaccac
     gagaaacatc ctgccaggtt
 661 taaacatcac ttgtaccttc cacaagactc agaatccaca
     gtgtcccatt ttccgactag
 721 gagacatctt ccgagaaaca ggcgataatt tttcagatgt
     ggcaattcag ggcggaataa
 781 tgggcattga gatctactgg gactgcaacc tagaccgttg
     gttccatcac tgccatccca
 841 aatacagttt ccgtcgcctt gacgacaaga ccaccaacgt
     gtccttgtac cctggctaca
 901 acttcagata cgccaagtac tacaaggaaa acaatgttga
     gaaacggact ctgataaaag
 961 tcttcgggat ccgttttgac atcctggttt ttggcaccgg
     aggaaaattt gacattatcc
1021 agctggttgt gtacatcggc tcaacctct cctacttcgg
     tctggccgct gtgttcatcg
1081 acttcctcat cgacacttac tccagtaact gctgtcgctc
     ccatatttat ccctggtgca
1141 agtgctgtca gccctgtgtg gtcaacgaat actactacag
     gaagaagtgc gagtccattg
1201 tggagccaaa gccgacatta aagtatgtgt cctttgtgga
     tgaatcccac attaggatgg
1261 tgaaccagca gctactaggg agaagtctgc aagatgtcaa
     gggccaagaa gtcccaagac
1321 ctgccgatgga cttcacagat ttgtccaggc tgccctggc
     cctccatgac acaccccga
1381 ttcctggaca accagaggag atacagccgc ttagaaagga
     ggcgactcct agatccaggg
1441 atagcccgt ctggtgccag tgtggaagct gcctcccatc
     tcaactccct gagagccaca
1501 ggtgcctgga ggagctgtgc tgccggaaaa agccgggggc
     ctgcatcacc acctcagagc
1561 tgttcaggaa gctggtcctg tccagacacg tcctgcagtt
     cctcctgctc taccaggagc
1621 ccttgctggc gctggatgtg gattccacca acagccggct
     gcggcactgt gcctacaggt
1681 gctacgccac ctggcgcttc ggctcccagg acatggctga
     ctttgccatc ctgcccagct
1741 gctgccgctg gaggatccgg aaagagtttc cgaagagtga
     agggcagtac agtggcttca
1801 agagtcctta ctgaagccag gcaccgtggc tcacgtctgt
     aatcccacct ttt
```

14. SEQ ID NO:14 The Following Sequence for the P2X7 Receptor is Derived from *H. sapiens* Brain (Accession Number Y09561) Protein Sequence

MPACCSCSDVFQYETNKVTRIQSMNYGTIKWFFHVIIFSYVCFA

LVSDKLYQRKEPVISSVHTKVKGIAEVKEEIVENGVKKLVHSVFDTADYTFPLQGNSF

FVMTNFLKTEGQEQRLCPEYPTRRTLCSSDRGCKKGWMDPQSKGIQTGRCVVHEGNQK

```
TCEVSAWCPIEAVEEAPRPALLNSAENFTVLIKNNIDFPGHNYTTRNILPGLNITCTF

HKTQNPQCPIFRLGDIFRETGDNFSDVAIQGGIMGIEIYWDCNLDRWFHHCHPKYSFR

RLDDKTTNVSLYPGYNFRYAKYYKENNVEKRTLIKVFGIRFDILVFGTGGKFDIIQLV

VYIGSTLSYFGLAAVFIDFLIDTYSSNCCRSHIYPWCKCCQPCVVNEYYYRKKCESIV

EPKPTLKYVSFVDESHIRMVNQQLLGRSLQDVKGQEVPRPAMDFTDLSRLPLALHDTP

PIPGQPEEIQLLRKEATPRSRDSPVWCQCGSCLPSQLPESHRCLEELCCRKKPGACIT

TSELFRKLVLSRHVLQFLLLYQEPLLALDVDSTNSRLRHCAYRCYATWRFGSQDMADF

AILPSCCRWRIRKEFPKSEGQYSFGKSPY
```

15. SEQ ID NO:15 The Following Sequence for the P2Y1 Receptor is Derived from *H. sapiens* (Accession Number S81950). Other Sequences Have Been Published for P2Y1 Receptors from Human Placenta (Accession Number Z49205), HEL Cells (Accession Number U42030), Bovine Endothelium (Accession Number X87628), Rat Cells (Accession Numbers U22830 and U22829), Turkey Brain (Accession Number U09842) and Chicken Brain (Accession Number X73268).

```
  1  ggatccagtt cgcctgctcc cttccgctcg ctggcttttc
     cgatgcttgc tgcgccctg 61  gccgccgctg ccctctcgcc gcctcctacc cctcggagcc
     gccgcctaag tcgaggagga 121  gagaatgacc gaggtgctgt ggccggctgt ccccaacggg
     acggacgctg ccttcctggc 181  cggtccgggt tcgtcctggg ggaacagcac ggtcgcctcc
     actgccgccg tctcctcgtc 241  gttcaaatgc gccttgacca agacgggctt ccagttttac
     tacctgccgg ctgtctacat 301  cttggtattc atcatcggct tcctgggcaa cagcgtggcc
     atctggatgt tcgtcttcca 361  catgaagccc tggagcggca tctccgtgta catgttcaat
     ttggctctgg ccgacttctt 421  gtacgtgctg actctgccag ccctgatctt ctactacttc
     aataaaacag actggatctt 481  cggggatgcc atgtgtaaac tgcagaggtt catctttcat
     gtgaacctct atggcagcat 541  cttgtttctg acatgcatca gtgcccaccg gtacagcggt
     gtggtgtacc ccctcaagtc 601  cctgggccgg ctcaaaaaga agaatgcgat ctgtatcagc
     gtgctggtgt ggctcattgt 661  ggtggtggcg atctccccca tcctcttcta ctcaggtacc
     ggggtccgca aaacaaaac 721  catcacctgt tacgacacca cctcagacga gtacctgcga
     agttatttca tctacagcat 781  gtgcacgacc gtggccatgt tctgtgtccc cttggtgctg
     attctgggct gttacggatt 841  aattgtgaga gctttgattt acaaagatct ggacaactct
     cctctgagga gaaaatcgat 901  ttacctggta atcattgtac tgactgtttt tgctgtgtct
     tacatcccct tccatgtgat 961  gaaaacgatg aacttgaggg cccggcttga ttttcagacc
     ccagcaatgt gtgctttcaa 1021 tgacagggtt tatgccacgt atcaggtgac aagaggtcta
     gcaagtctca acagttgtgt 1081 ggaccccatt ctctatttct tggcgggaga tactttcaga
     aggagactct cccgagccac 1141 aaggaaagct tctagaagaa gtgaggcaaa tttgcaatcc
     aagagtgaag acatgaccct 1201 caatatttta cctgagttca agcagaatgg agatacaagc
     ctgtgaaggc acaagaatct 1261 ccaaacacct ctctgttgta atatggtagg atgcttaaca
     gaatcaagta ct
```

16. SEQ ID NO:16 The Following Sequence for the P2Y1 Receptor is Derived from *H. sapiens* (Accession Number S81950).

```
MTEVLWPAVPNGTDAAFLAGPGSSWGNSTVASTAAVSSSFKCAL

TKTGFQFYYLPAVYILVFIIGFLGNSVAIWMFVFHMKPWSGISVYMFNLALADFLYVL

TLPALIFYYFNKTDWIFGDAMCKLQRFIFHVNLYGSILFLTCISAHRYSGVVYPLKSL

GRLKKKNAICISVLVWLIVVVAISPILFYSGTGVRKNKTITCYDTTSDEYLRSYFIYS
```

-continued

MCTTVAMFCVPLVLILGCYGLIVRALIYKDLDNSPLRRKSIYLVIIVLTVFAVSYIPF

HVMKTMNLRARLDFQTPAMCAFNDRVYATYQVTRGLASLNSCVDPILYFLAGDTFRRR

LSRATRKASRRSEANLQSKSEDMTLNILPEFKQNGDTSL

17. SEQ ID NO:17 The Following Sequence for the P2Y2 Receptor is Derived from *H. sapiens* Epithelial Cells (Accession Number U07225). Other Sequences have been Published for P2Y2 Receptors from Rat Alveolar Cells (Accession Number U09402), Rat Pituitary Cells (Accession Number L46865), Wistar Kyoto Rat (Accession Number U56839), and Mouse Neuroblastoma Cells (Accession Number NM-008773).

```
   1 cggcacgagg caccccgaga ggagaagcgc agcgcagtgg
     cgagaggagc cccttgtggc
  61 agcagcacta cctgcccaga aaaatgctgg aggctgggcg
     tggccccagg cctggggacc
 121 tgttttttcct gtttcccgca gagttccctg cagcccggtc
     caggtccagg cgtgtgcatt
 181 catgagtgag gaacccgtgc aggcgctgag catcctgacc
     tggagagcag gggctggtca
 241 gggcgatggc agcagacctg ggcccctgga atgacaccat
     caatggcacc tgggatgggg
 301 atgagctggg ctacaggtgc cgcttcaacg aggacttcaa
     gtacgtgctg ctgcctgtgt
 361 cctacggcgt ggtgtgcgtg cttgggctgt gtctgaacgc
     cgtggcgctc tacatcttct
 421 tgtgccgcct caagacctgg aatgcgtcca ccacatatat
     gttccacctg gctgtgtctg
 481 atgcactgta tgcggcctcc ctgccgctgc tggtctatta
     ctacgcccgc ggcgaccact
 541 ggcccttcag cacggtgctc tgcaagctgg tgcgcttcct
     cttctacacc aacctttact
 601 gcagcatcct cttcctcacc tgcatcagcg tgcaccggtg
     tctgggcgtc ttacgacctc
 661 tgcgctccct gcgctggggc cgggcccgct acgctcgccg
     ggtggccggg gccgtgtggg
 721 tgttggtgct ggcctgccag gccccccgtgc tctactttgt
     caccaccagc gcgcgcgggg
 781 gccgcgtaac ctgccacgac acctcggcac ccgagctctt
     cagccgcttc gtggcctaca
 841 gctcagtcat gctgggcctg ctcttcgcgg tgcccttttgc
     cgtcatcctt gtctgttacg
 901 tgctcatggc tcggcgactg ctaaagccag cctacgggac
     ctcgggcggc ctccctaggg
 961 ccaagcgcaa gtccgtgcgc accatcgccg tggtgctggc
     tgtcttcgcc ctctgcttcc
1021 tgccattcca cgtcacccgc acctctact actccttccg
     ctcgctggac tcagctgcc
1081 acacccttcaa cgccatcaac atggcctaca aggttacccg
     gccgctggcc agtgctaaca
```

-continued

```
1141 gttgccttga ccccgtgctc tacttcctgg ctgggcagag
     gctcgtacgc tttgcccgag
1201 atgccaagcc acccactggc cccagccctg ccaccccggc
     tcgccgcagg ctgggcctgc
1261 gcagatccga cagaactgac atgcagagga taggagatgt
     gttgggcagc agtgaggact
1321 tcaggcggac agagtccacg ccggctggta gcgagaacac
     taaggacatt cggctgtagg
1381 agcagaacac ttcagcctgt gcaggtttat attgggaagc
     tgtagaggac caggacttgt
1441 gcagacgcca cagtctcccc agatatggac catcagtgac
     tcatgctgga tgacccatg
1501 ctccgtcatt tgacagggc tcaggatatt cactctgtgg
     tccagagtca actgttccca
1561 taaccctag tcatcgtttg tgtgtataag ttggggaat
     taagtttcaa gaaaggcaag
1621 agctcaaggt caatgacacc cctggcctga ctcccatgca
     agtagctggc tgtactgcca
1681 aggtacctag gttggagtcc agcctaatca agtcaaatgg
     agaaacaggc cagagagga
1741 aggtggctta ccaagatcac ataccagagt ctggagctga
     gctacctggg gtggggcca
1801 agtcacaggt tggccagaaa accctggtaa gtaatgaggg
     ctgagtttgc acagtggtct
1861 ggaatggact gggtgccacg gtggacttag ctctgaggag
     tacccccagc ccaagagatg
1921 aacatctggg gactaatatc atagacccat ctggaggctc
     ccatgggcta ggagcagtgt
1981 gaggctgtaa cttatactaa aggttgtgtt gcctgctaaa
     aaaaa
```

18. SEQ ID NO:18 The Following Sequence for the P2Y2 Receptor is Derived from *H. sapiens* Epithelial Cells (Accession Number U07225) Protein Sequence.

MAADLGPWNDTINGTWDGDELGYRCRFNEDFKYVLLPVSYGVVC

VLGLCLNAVALYIFLCRLKTWNASTTYMFHLAVSDALYAASLPLLVYYYARGDHWPFS

TVLCKLVRFLFYTNLYCSILFLTCISVHRCLGVLRPLRSLRWGRARYARRVAGAVWVL

VLACQAPVLYFVTTSARGGRVTCHDTSAPELFSRFVAYSSVMLGLLFAVPFAVILVCY

VLMARRLLKPAYGTSGGLPRAKRKSVRTIAVVLAVFALCFLPFHVTRTLYYSFRSLDL

SCHTLNAINMAYKVTRPLASANSCLDPVLYFLAGQRLVRFARDAKPPTGPSPATPARR

RLGLRRSDRTDMQRIGDVLGSSEDFRRTESTPAGSENTKDIRL

19. SEQ ID NO:19 The Following Sequence for the P2y3 Receptor is Derived from Chick Brain (Accession Number X98283).

```
  1 ggcgcttcac ccagtaaaga gggaccatga gcatggccaa
    cttcacgggg gggaggaact
 61 cgtgcacctt ccatgaggaa ttcaagcagg tcctgctgcc
    cctggtctac tcagtggtgt
121 tcctactggg gctgccactc aatgccgttg tcattgggca
    gatctggctg gcccgcaagg
181 cgttgacccg caccaccatc tacatgctga acctggccat
    ggccgacctg ctttatgtct
241 gctccctccc tctcctcatc tacaactaca cccagaagga
    ttactggccc tttggggact
301 tcacctgcaa attcgtccgc ttccagttct acaccaacct
    gcacggcagc atcctcttcc
361 tcacctgcat cagcgtccag cgctacatgg ggatctgcca
    cccttggcc tcgtggcaca
```

```
                          -continued
421 aaaagaaggg aaagaagctg acgtggctgg tgtgtgctgc
    cgtgtggttc atcgtcatcg
481 cccagtgcct gcccaccttt gtcttcgcct ccaccggcac
    gcagaggaat cgcactgtct
541 gctatgacct gagcccccg gaccgctcca catcctactt
    cccctatggc atcacgttga
601 ccatcactgg cttcctgctg cccttcgcag ccatcctggc
    ctgctactgc agcatggccc
661 gcatcctgtg ccagaaagac gagctgattg gcttggcggt
    gcacaagaag aaggacaagg
```

```
                          -continued
721 ccgtgcgcat gatcatcatc gttgtcatcg tcttctccat
    cagcttcttc cccttccacc
781 tcaccaagac catctacctg atcgtccgct cctcagccag
    cttgccctgc cctaccctgc
841 aggcttttgc cattgcctac aagtgcacgc ggcccttttgc
    cagcatgaac agcgtcctcg
901 acccatcct cttctacttc acccagcgca gtttcgtga
    gagcacccgc tatctcctgg
961 acaagatgag ctccaagtgg cggcaagacc actgcatcag
    ctacggctcc taggtggacg
1021 aggccacctc ggtgtcaccg gggctgggca tggagcaatt
     tgggttgaag ctgcatggtg
1081 cggagatggg gatgagccca gagtgctgcg ggtgccccat
     ctctggaggt gttggagatt
1141 agattggatg gggctctggg ccc
```

20. SEQ ID NO:20 The Following Sequence for the P2y3 Receptor is Derived from Chick Brain (Accession Number X98283) Protein Sequence.

MSMANFTGGRNSCTFHEEFKQVLLPLVYSVVFLLGLPLNAVVIG

QIWLARKALTRTTIYMLNLAMADLLYVCSLPLLIYNYTQKDYWPFGDFTCKFVRFQFY

TNLHGSILFLTCISVQRYMGICHPLASWHKKKGKKLTWLVCAAVWFIVIAQCLPTFVF

ASTGTQRNRTVCYDLSPPDRSTSYFPYGITLTITGFLLPFAAILACYCSMARILCQKD

ELIGLAVHKKKDKAVRMIIVVIVFSISFFPFHLTKTIYLIVRSSASLPCPTLQAFAI

AYKCTRPFASMNSVLDPILFYFTQRKFRESTRYLLDKMSSKWRQDHCISYGS

21. SEQ ID NO:21 The Following Sequence for the P2Y4 Receptor is Derived from *H. sapiens* (Accession Number X91852). Other Sequences have been Published for P2Y4 Receptors from Human Chromosome X (Accession Number U40223), and rat heart (Accession Number Y14705).

```
  1 aagggagctt gggtaggggc caggctagcc tgagtgcacc
    cagatgcgct tctgtcagct
 61 ctccctagtg cttcaaccac tgctctccct gctctacttt
    ttttgctcca gctcagggat
121 gggggtgggc agggaaatcc tgccaccctc acttctcccc
    ttcccatctc caggggggcc
```

-continued

```
 181  atggccagta cagagtcctc cctgttgaga tccctaggcc
      tcagcccagg tcctggcagc 241  agtgaggtgg agctggactg ttggtttgat gaggatttca
      agttcatcct gctgcctgtg 301  agctatgcag ttgtctttgt gctgggcttg ggccttaacg
      ccccaaccct atggctcttc 361  atcttccgcc tccgaccctg ggatgcaacg gccacctaca
      tgttccacct ggcattgtca
```

-continued

```
 421  gacaccttgt atgtgctgtc gctgcccacc ctcatctact
      attatgcagc ccacaaccac 481  tggcccttg  gcactgagat ctgcaagttc gtccgctttc
      ttttctattg gaacctctac 541  tgcagtgtcc ttttcctcac ctgcatcagc gtgcaccgct
      acctgggcat ctgccaccca 601  cttcgggcac tacgctgggg ccgccctcgc ctcgcaggcc
      ttctctgcct ggcagttttgg 661  ttggtcgtag ccggctgcct cgtgcccaac ctgttctttg
      tcacaaccag caacaaaggg 721  accaccgtcc tgtgccatga caccactcgg cctgaagagt
      ttgaccacta tgtgcacttc 781  agctcggcgg tcatggggct gctctttggc gtgccctgcc
      tggtcactct tgttttgctat 841  ggactcatgg ctcgtcgcct gtatcagccc ttgccaggct
      ctgcacagtc gtcttctcgc 901  ctccgctctc tccgcaccat agctgtggtg ctgactgtct
      ttgctgtctg cttcgtgcct 961  ttccacatca cccgcaccat ttactacctg gccaggctgt
      tggaagctga ctgccgagta 1021  ctgaacattg tcaacgtggt ctataaagtg actcggcccc
      tggccagtgc caacagctgc 1081  ctggatcctg tgctctactt gctcactggg gacaaatatc
      gacgtcagct ccgtcagctc 1141  tgtggtggtg gcaagcccca gccccgcacg gctgcctctt
      ccctggcact agtgtccctg 1201  cctgaggata gcagctgcag gtgggcggcc accccccagg
      acagtagctg ctctactcct 1261  agggcagata gattgtaaca cgggaagccg ggaagtgaga
      gaaaagggga tgagtgcagg
```

-continued

```
1321  gcagaggtga gggaacccaa tagtgatacc tggtaaggtg
      cttcttcctc ttttccaggc 1381  tctggagaga agccctcacc ctgagggttg ccagggaggc
      agggatatc
```

22. SEQ ID NO:22 The Following Sequence for the P2Y4 Receptor is Derived from *H. sapiens* (Accession Number X91852) Protein Sequence.

MASTESSLLRSLGLSPGPGSSEVELDCWFDEDFKFILLPVSYAV

VFVLGLGLNAPTLWLFIFRLRPWDATATYMFHLALSDTLYVLSLPTLIYYYAAHNHWP

FGTEICKFVRFLFYWNLYCSVLFLTCISVHRYLGICHPLRALRWGRPRLAGLLCLAVW

LVVAGCLVPNLFFVTTSNKGTTVLCHDTTRPEEFDHYVHFSSAVMGLLFGVPCLVTLV

CYGLMARRLYQPLPGSAQSSSRLRSLRTIAVVLTVFAVCFVPFHITRTIYYLARLLEA

DCRVLNIVNVVYKVTRPLASANSCLDPVLYLLTGDKYRRQLRQLCGGGKPQPRTAASS

LALVSLPEDSSCRWAATPQDSSCSTPRADRL

23. SEQ ID NO:23 The Following Sequence for the P2Y6 Receptor is Derived from *H. sapiens* Placenta (Accession NumberX97058). Other Sequences have been Published for P2Y6 Receptors from Human Placenta (Accession Number AF007893), and Human Activated T-Cells (Accession Number U52464).

```
   1  ctcagtttcc tcatctgctg cctctccaga cttctgccag
      aacattgcac gcgacagttt 61  caggcacaga actgactggc agcaggggct gctccacgag
      tgggaatttg ctccagcact 121  tcacggactg caagcgaggc acttgctaac tcttggataa
      caagacctct gccagaagaa 181  ccatggcttt ggaaggcgga gttcaggctg aggagatggg
      tgcggtcctc agtgagcccc 241  tgcctccctg aacataggaa acccacctgg gcagccatgg
      aatgggacaa tggcacaggc 301  caggctctgg gcttgccacc caccacctgt gtctaccgcg
      agaacttcaa gcaactgctg 361  ctgccacctg tgtattcggc ggtgctggcg gctggcctgc
      cgctgaacat ctgtgtcatt 421  acccagatct gcacgtcccg ccgggccctg acccgcacgg
      ccgtgtacac cctaaacctt 481  gctctggctg acctgctata tgcctgctcc ctgcccctgc
      tcatctacaa ctatgcccaa 541  ggtgatcact ggccctttgg cgacttcgcc tgccgcctgg
      tccgcttcct cttctatgcc 601  aacctgcacg gcagcatcct cttcctcacc tgcatcagct
      tccagcgcta cctgggcatc 661  tgccaccgc  tggccccctg gcacaaacgt ggggccgcc
      gggctgcctg gctagtgtgt
```

```
 721  gtagccgtgt ggctggccgt gacaacccag tgcctgccca
      cagccatctt cgctgccaca 781  ggcatccagc gtaaccgcac tgtctgctat gacctcagcc
      cgcctgccct ggccacccac 841  tatatgccct atggcatggc tctcactgtc atcggcttcc
      tgctgccctt tgctgccctg 901  ctggcctgct actgtctcct ggcctgccgc ctgtgccgcc
      aggatggccc ggcagagcct 961  gtggcccagg agcggcgtgg caaggcggcc cgcatggccg
      tggtggtggc tgctgccttt 1021  gccatcagct tcctgccttt tcacatcacc aagacagcct
      acctggcagt gcgctcgacg 1081  ccgggcgtcc cctgcactgt attggaggcc tttgcagcgg
      cctacaaagg cacgcggccg 1141  tttgccagtg ccaacagcgt gctggacccc atcctcttct
      acttcacccg aagaagttc 1201  cgccggcgac cacatgagct cctacagaaa ctcacagcca
      aatggcagag gcagggtcgc 1261  tgagtcctcc aggtcctggg cagccttcat atttgccatt
      gtgtccgggg caccaggagc 1321  cccaccaacc ccaaaccatg cggagaatta gagttcagct
      cagctgggca tggagttaag 1381  atccctcaca ggacccagaa gctcaccaaa aactatttct
      tcagcccctt ctctggccca 1441  gaccctgtgg gcatggagat ggacagacct gggcctggct
      cttgagaggt cccagtcagc 1501  catggagagc tggggaaacc acattaaggt gctcacaaaa
      atacagtgtg acgtgtactg 1561  tcaaaaaaaa a
```

24. SEQ ID NO:22 The Following Sequence for the P2Y6 Receptor is Derived from *H. sapiens* (Accession Number X91852) Protein Sequence.

```
MEWDNGTGQALGLPPTTCVYRENFKQLLLLPPVYSAVLAAGLPLNICVITQICTSRRALTRTA

VYTLNLALADLLYACSLPLLIYNYAQGDHWPFGDFACRLVRFLFYANLHGSILFLTCISFQR

YLGICHPLAPWHKRGGRRAAWLVCVAVWLAVTTQCLPTAIFAATGIQRNRTVCYDLSPPALA

THYMPYGMALTVIGFLLPFAALLACYCLLACRLCRQDGPAEPVAQERRGKAARNAVVVAAAF

AISFLPFHITKTAYLAVRSTPGVPCTVLEAFAAAYKGTRPFASANSVLDPILFYFTQKKFRR

RPHELLQKLTAKWQRQGR
```

25. SEQ ID NO:24 The Following Sequence for the P2Y11 Receptor is Derived from Human Placenta (Accession Number AF030335). Other Sequences have been Published for P2Y11 Receptors from Human HL-60 Cells (Accession Number AJ298334).

```
   1  atggatcgag gtgccaagtc ctgccctgcc aacttcttgg
      cagctgccga cgacaaactc 61  agtgggttcc aggggggactt cctgtggccc atactggtgg
      ttgagttcct ggtggccgtg 121  gccagcaatg gcctggccct gtaccgcttc agcatccgga
      agcagcgccc atggcacccc 181  gccgtggtct tctctgtcca gctggcagtc agcgacctgc
      tctgcgctct gacgctgccc 241  ccgctggccg cctacctcta tccccccaag cactggcgct
      atggggaggc cgcgtgccgc 301  ctggagcgct tcctcttcac ctgcaacctg ctyggcagcg
      tcatcttcat cacctgcatc 361  agcctcaacc gctacctggg catcgtgcac cccttcttcg
      cccgaagcca cctgcgaccc 421  aagcacgcct gggccgtgag cgctgccggc tgggtcctgg
      ccgccctgct ggccatgccc 481  acactccagct tctcccacct gaagaggccg cagcagggg
      cgggcaactg cagcgtggcc 541  aggcccgagg cctgcatcaa gtgtctgggg acagcagacc
      acgggctggc ggcctacaga 601  gcgtatagcc tggtgctggc ggggttgggc tgcggcctgc
      cgctgctgct cacgctggca 661  gcctacggcg ccctcgggcg ggccgtgcta cgcagcccag
      gcatgactgt ggccgagaag 721  ctgcgtgtgg cagcgttggt ggccagtggt gtggccctct
      acgccagctc ctatgtgccc 781  taccacatca tgcgggtgct caacgtggat gctcggcggc
      gctggagcac ccgctgcccg 841  agctttgcag acatagccca ggccacagca gccctggagc
      tggggcccta cgtgggctac 901  caggtgatgc ggggcctcat gccctgcc ttctgtgtcc
      accctctact ctacatggcc 961  gcagtgccca gcctgggctg ctgctgccga cactgccccg
      gctacaggga cagctggaac 1021  ccagaggacg ccaagagcac tggccaagcc ctgcccctca
      atgccacagc cgcccctaaa 1081  ccgtcagagc cccagtcccg tgagctgagc caatga
```

26. The Following Sequence for the P2Y11 Receptor is Derived from Human Placenta (Accession Number AF030335) Protein Sequence.

MDRGAKSCPANFLAAADDKLSGFQGDFLWPILVVEFLVAVASNG

LALYRFSIRKQRPWHPAVVFSVQLAVSDLLCALTLPPLAAYLYPPKHWRYGEAACRLE

RFLFTCNLLGSVIFITCISLNRYLGIVHPFFARSHLRPKHAWAVSAAGWVLAALLAMP

TLSFSHLKRPQQGAGNCSVARPEACIKCLGTADHGLAAYRAYSLVLAGLGCGLPLLLT

LAAYGALGRAVLRSPGMTVAEKLRVAALVASGVALYASSYVPYHIMRVLNVDARRRWS

TRCPSFADIAQATAALELGPYVGYQVMRGLMPLAFCVHPLLYMAAVPSLGCCCRHCPG

YRDSWNPEDAKSTGQALPLNATAAPKPSEPQSRELSQ

---

What is claimed is:

1. A method of modulating odor sensitivity in a subject, comprising administering a composition by topical intranasal administration or inhalant through the nose or mouth to the subject, wherein the composition is an agonist of a P2X or P2Y purinergic receptor, and wherein the subject is a mammal.

2. The method of claim 1, wherein the agonist is a P2X selective agonist.

3. The method of claim 1, wherein the agonist is a P2Y selective agonist.

4. The method of claim 1, wherein the agonist is a non-selective agonist.

5. The method of claim 1, wherein the agonist enhances the $Ca^{2+}$ released from coapplication of an odor stimulant and the agonist.

6. The method of claim 1, wherein the agonist suppresses the $Ca^{2+}$ released from the coapplication of an odor stimulant and the agonist.

7. The method of claim 1, wherein the agonist increases the ratio of observed co-application-evoked calcium transient over the sum of individual odor and P2 agonists peak amplitudes in a cell activation assay.

8. The method of claim 1, wherein the agonist decreases the ratio of observed co-application evoked calcium transient over the sum of individual odor and P2 agonists peak amplitudes in a cell activation assay.

9. A method of modulating odor sensitivity in a subject, comprising administering a composition by topical intranasal administration or inhalant through the nose or mouth to the subject, wherein the composition is an agonist of a P2X purinergic receptor, and wherein the subject is a mammal.

10. A method of modulating odor sensitivity in a subject, comprising administering a composition by topical intranasal administration or inhalant through the nose or mouth to the subject, wherein the composition is an agonist of a P2Y purinergic receptor, and wherein the subject is a mammal.

11. A method of modulating odor sensitivity in a subject, comprising administering a composition by topical intranasal administration or inhalant through the nose or mouth to the subject, wherein the composition is an antagonist of a P2X or P2Y purinergic receptor, and wherein the subject is a mammal.

12. A method of protecting a cell from the effects of odor stimulation comprising administering a composition to the cell, wherein the composition is an antagonist or an agonist of a P2Y or a P2X purinergic receptor.

13. A method of modulating odor sensitivity in a subject, comprising inhibiting the interaction of ATP or ATP analog with a P2X or a P2Y purinergic receptor, wherein the subject is a mammal.

* * * * *